United States Patent [19]

Clark et al.

[11] Patent Number: 4,613,606
[45] Date of Patent: Sep. 23, 1986

[54] TETRAHYDROISOQUINOLINE DERIVATIVES

[75] Inventors: Robin Clark, Palo Alto; Joseph M. Muchowski, Sunnyvale; Fang-Ting Chiu, Union City; John O. Gardner, Los Altos; Jacob Berger, Los Altos Hills, all of Calif.

[73] Assignee: Syntex (U.S.A.) Inc., Palo Alto, Calif.

[21] Appl. No.: 803,464

[22] Filed: Dec. 2, 1985

[51] Int. Cl.$^4$ .................... A61K 31/47; C07D 217/20
[52] U.S. Cl. .................................. 514/307; 546/145; 549/442; 549/365; 558/410; 558/404; 558/408; 560/29; 568/586; 568/587
[58] Field of Search .................. 546/145; 514/307

[56] References Cited

U.S. PATENT DOCUMENTS 4,369,322  1/1983  Schalke et al. .................... 546/145

FOREIGN PATENT DOCUMENTS 1802804  6/1970  Fed. Rep. of Germany ...... 546/145

*Primary Examiner*—Glennon H. Hollrah
*Assistant Examiner*—James H. Turnipseed
*Attorney, Agent, or Firm*—Grant D. Green; Tom M. Moran; Alan M. Krubiner

[57] ABSTRACT

Compounds of the formula

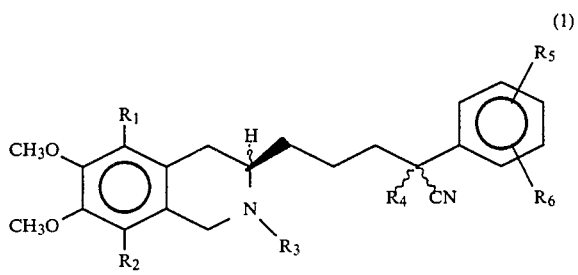

(1)

wherein
  $R_1$ and $R_2$ are each independently —H or lower alkoxy;
  $R_3$ and $R_4$ are each independently lower alkyl; and
  $R_5$ and $R_6$ are each —OCH$_3$, or together form —OCH$_2$O— or —OCH$_2$CH$_2$O— and pharmaceutically acceptable acid addition salts thereof are calcium channel blockers useful for treating cardiovascular disorders including angina, hypertension and congestive heart failure.

10 Claims, No Drawings

TETRAHYDROISOQUINOLINE DERIVATIVES

BACKGROUND OF THE INVENTION

1. Field of the Invention

This invention relates to novel 3-(4-cyano-4-phenylalkyl)tetrahydroisoquinoline derivatives and the pharmaceutically acceptable salts thereof, pharmaceutical compositions containing said derivatives or salts, and the use thereof to treat cardiovascular disorders including angina, hypertension, and congestive heart disease. This invention also relates to a novel process for preparing the compounds of the invention, and novel intermediates therefor.

2. Related Disclosure

Certain other calcium channel blocking agents are known, such as verapamil, N-[4-(3,4-dimethoxyphenyl)-4-cyano-4-(prop-2-yl)butyl]-N-(3,4-dimethoxyphenethyl)-N-methylamine, (U.S. Pat. No. 3,261,859). Although verapamil has enjoyed widespread commercial success, it is short-acting, necessitating administration three or four times per day. Also, it is cardiodepressive, and decreases cardiac conduction. It has now been found that the compounds of the invention are less cardiodepressive and longer-acting than verapamil. Compounds of the invention are orally active and decrease afterload and preload, while increasing coronary bloodflow. Compounds of the invention also increase the heart rate pressure product without increasing the heart rate. Compounds of the invention do not cause pathological prolongation of A-V conduction at effective concentrations, and do not cause orthostatic hypotension. Compounds of the invention decrease ECG ST-segment elevation in pacing-induced angina models.

DEFINITIONS

As used in the specification and appended claims, unless specified to the contrary, the following terms have the meaning indicated:

The term "lower alkyl" refers to a straight or branched chain monovalent substituent consisting solely of carbon and hydrogen, containing no unsaturation and having from one to five carbon atoms. Examples of lower alkyl groups are methyl, ethyl, n-propyl, i-propyl, n-butyl, i-butyl, s-butyl, t-butyl, n-pentyl, and 3-pentyl.

The term "lower alkoxy" refers to radicals of the form RO—, where R is lower alkyl as defined above.

The term "alkanol" refers to lower alkyl alcohols such as methanol, ethanol, propanol, isopropanol, butanol, and the like.

The term "halo" as used herein refers to chloro, bromo and iodo.

The term "aryl" refers to aromatic radicals consisting entirely of carbon and hydrogen, containing from 6 to 12 carbon atoms. Examples of aryl groups are phenyl, naphthyl, and the like.

The term "acylating agent" refers to compounds which are useful for adding a radical of the form RC(O)— (where R is lower alkyl) to a hydroxy group, e.g., for converting HO— to $CH_3COO$—. Acylating agents include acylating agents such as acetic anhydride and acetyl chloride. Other acylating agents within the scope of this definition include acyl anhydrides and acyl halides such as propanoyl chloride, butanoyl bromide, 3-methylbutanoyl chloride and the like.

The term "acyl anhydride" refers to compounds of the formula $R_aC(O)$—O—$C(O)R_b$, where $R_a$ and $R_b$ are each independently lower alkyl, which are typically produced by the condensation of two lower alkyl carboxylic acids. Exemplary acyl anhydrides are formic anhydride, acetic anhydride, formic-acetic anhydride, formic-pentanoic anhydride, and pentanoic-pentanoic anhydride.

The term "noble metal catalyst" refers to catalysts in which the active component is primarily a noble metal, such as platinum, palladium, osmium, and the like. Such catalysts are commonly used in the practice of catalytic hydrogenation, hydrogenolysis, and similar reactions.

The term "catalytic amount" refers to the amount of catalyst that must be added in order to effect catalysis, i.e., to increase the yield or rate of reaction by a significant amount. Due to the nature of catalysis, the "catalytic amount" will vary widely depending on the reaction and the catalyst used. However, given the particular catalyst and reaction, one of ordinary skill in the art will be above to determine the catalytic amount through routine experimentation.

The term "formaldehyde source" refers to formaldehyde and compounds which can be used to supply formaldehyde to a reaction mixture. For example, paraformaldehyde decomposes in solution to yield formaldehyde, and is thus a formaldehyde source within the meaning of this definition. Formalin also falls within the scope of this definition.

The term "paraformaldehyde" refers to polymerized formaldehyde, $(CH_2O)_n$. Paraformaldehyde is commerically available, and is used as a source of formaldehyde in chemical reactions.

The term "boron-based reducing agent" refers to sodium borohydride, diborane, and similar alkylboron reducing agents.

The term "metallic base" refers to metal-based bases such as sodium, NaH, Raney nickel, potassium t-butoxide, lithium aluminum hydride, $NaNH_2$, and the like.

The term "protecting group" refers to a group that is used to prevent hydroxy or carbonyl groups from reacting undesirably during the preparation of compounds of the invention. Examples of protecting groups are benzyl ethers, ketals (e.g., acetonides), and esters. Protecting groups are ideally easily applied and removed under conditions unlike the reaction conditions used in the preparations. For example, t-butyl carbonate esters are stable under the $SN_2$ reaction conditions used in preparation of compounds of formula 1, but are easily displaced using formic acid and formic-acetic anhydride.

The term "pharmaceutically acceptable salts" refers to salts of the subject compounds which possess the desired pharmacological activity and which are neither biologically nor otherwise undesirable. These salts are acid addition salts formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or
(iii) relieving the disease, i.e., causing regression of the disease.

Compounds of formula 1 are named and numbered as derivatives of isoquinoline using a modified form of IUPAC nomenclature. For example, the compound below is named 3-[4-(3,4-dimethoxyphenyl)-4-isopropyl-4-cyanobutyl]-6,7-dimethoxy-N-methyl-1,2,3,4-tetrahydroisoquinoline:

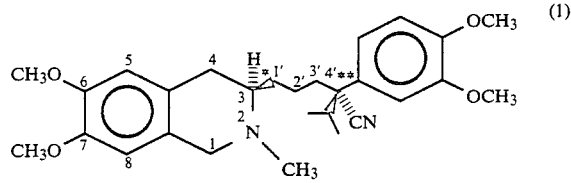

Compounds of formula 1 have two asymmetric sites, $C_3$ and $C_4$, (marked above as * and **, respectively), and thus can exist as diastereomers. Individual isomers of compounds of formula 1 are named herein using the IUPAC R-S convention, sometimes called the "sequence rule." A description of the R-S convention may be found, for example, in "Introduction to Organic Chemistry" by A. Streitwieser, Jr. and C. Heathcock, (Macmillan Pub. Co., New York, 1976), pages 110-114. Diastereomers will be indicated as (3R, 4'S), (3R, 4'R), (3S, 4'S) or (3S, 4'R) as appropriate. For example, the compound illustrated above is (3R, 4'S). Where appropriate, the optical activity of a compound may be indicated by (+), (−), or (±), referring to the direction in which a solution of the compound rotates a plane of polarized light.

SUMMARY OF THE INVENTION

One aspect of the invention is a compound of the formula

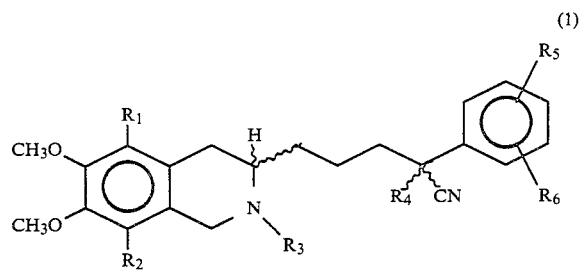

or a pharmaceutically acceptable acid addition salt thereof, wherein $R_1$ and $R_2$ are each independently —H or lower alkoxy, $R_3$ and $R_4$ are each independently lower alkyl, and $R_5$ and $R_6$ are each —OCH$_3$ or together form —OCH$_2$O— or —OCH$_2$CH$_2$O—.

Another aspect of the invention is a mixture of compounds of formula 1.

Another aspect of the invention is a pharmaceutical composition which comprises a compound of formula 1 and a pharmaceutically acceptable excipient.

Another aspect of the invention is a method for treating cardiovascular diseases susceptible to treatment by calcium channel blockade, which diseases include angina, hypertension, and congestive heart failure.

Another aspect of the invention is a novel process for preparing compounds of formula 1.

Another aspect of the invention is an intermediate of formula 11 which is useful for preparing compounds of formula 1:

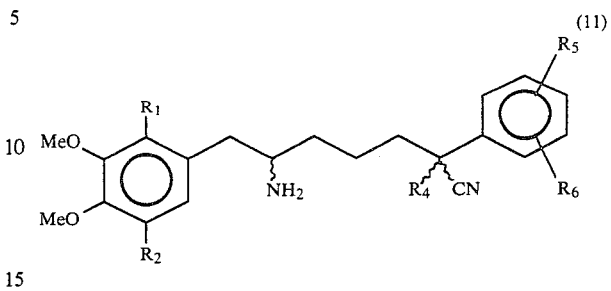

and pharmaceutically acceptable salts thereof, where $R_1$, $R_2$, $R_4$, $R_5$ and $R_6$ are as defined above.

Another aspect of the invention is an intermediate of formula 8 which is useful for preparing intermediates of formula 11:

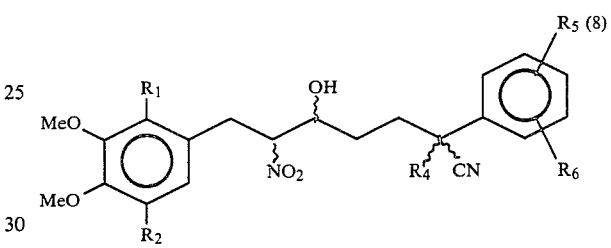

and pharmaceutically acceptable salts thereof, where $R_1$, $R_2$, $R_4$, $R_5$ and $R_6$ are as defined above.

DETAILED DESCRIPTION AND PREFERRED EMBODIMENTS

One aspect of the invention is a compound of the formula

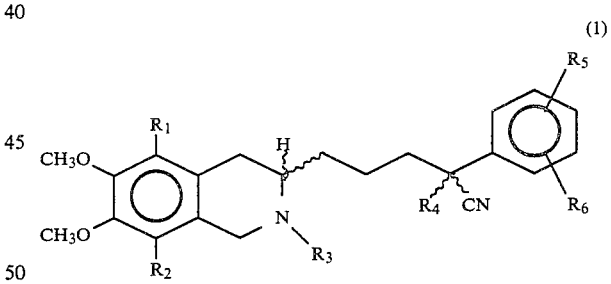

or a pharmaceutically acceptable acid addition salt thereof, wherein $R_1$ and $R_2$ are each independently —H or lower alkoxy; $R_3$ and $R_4$ are each independently lower alkyl; and $R_5$ and $R_6$ are each —OCH$_3$, or together form —OCH$_2$O— or —OCH$_2$CH$_2$O—. A preferred subgenus of the invention is the compound wherein $R_4$ is isopropyl. A preferred class is the compound wherein $R_3$ is methyl. A preferred subclass is the compound wherein $R_1$ and $R_2$ are each H, particularly where $R_5$ and $R_6$ are each —OCH$_3$. A presently preferred embodiment is the compound (3S, 4'S) 3-[4-(3,4-dimethoxyphenyl)-4-isopropyl-4-cyanobutyl]-6,7-dimethoxy-N-methyl-1,2,3,4-tetrahydroisoquinoline. Another presently preferred embodiment is the compound (3S, 4'S) 3-[4-(3,4-dimethoxyphenyl)-4-isopropyl-4-cyanobutyl]-6,7-dimethoxy-N-methyl-1,2,3,4-tetrahydroisoquinoline.HCl.

Another aspect of the invention is a mixture of compounds of formula 1. A preferred class is an approximately racemic mixture of diastereomers. A presently preferred embodiment is the mixture of the (3S, 4'S), (3S, 4'R), (3R, 4'S), and (3R, 4'R) isomers of 3-[4-(3,4-dimethoxyphenyl)-4-isopropyl-4-cyanobutyl]-6,7-dimethoxy-N-methyl-1,2,3,4-tetrahydroisoquinoline. Another presently preferred embodiment is the mixture of the (3S, 4'S), (3S, 4'R), (3R, 4'S), and (3R, 4'R) isomers of 3-[4-(3,4-dimethoxyphenyl)-4-isopropyl-4-cyanobutyl]-6,7-dimethoxy-N-methyl-1,2,3,4-tetrahydroisoquinoline·HCl. Another preferred embodiment is an approximately equimolar mixture of (3S, 4'S) and (3S, 4'S) 3-[4-(3,4-dimethoxyphenyl)-4-isopropyl-4-cyanobutyl]-6,7-dimethoxy-N-methyl-1,2,3,4-tetrahydroisoquinoline.

Another aspect of the invention is a pharmaceutical composition which comprises a compound of formula 1 and a pharmaceutically acceptable excipient.

Another aspect of the invention is a method for treating cardiovascular diseases susceptible to treatment with calcium channel blockers, which diseases include angina, hypertension, and congestive heart failure, which method comprises administering an effective amount of a compound of formula 1 to a mammal in need thereof.

Another aspect of the invention is a process for preparing compounds of formula 1, which process comprises heating at 70° to 110° C. for 1 to 24 hours a mixture of formic acid, a formaldehyde source, and a compound of formula 11:

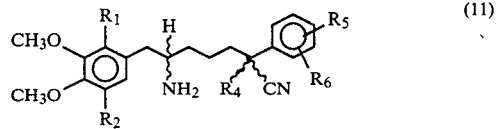

wherein $R_1$ and $R_2$ are each independently —H or lower alkoxy; $R_4$ is lower alkyl; and $R_5$ and $R_6$ are each —OCH$_3$, or together form —OCH$_2$O— or —OCH$_2$CH$_2$O—. A preferred subgenus of the invention is the process wherein $R_1$ and $R_2$ are each —H, $R_4$ is prop-2-yl, and $R_5$ and $R_6$ are each —OCH$_3$. A preferred class is the process wherein said mixture is heated at about 80° C. for 2 to 8 hours. A preferred subclass is the process wherein said compound of formula 11 is obtained by mixing in an inert solvent an acylating agent (preferably acetic anhydride), a catalytic amount of base (preferably 4-dimethylaminopyridine), and a compound of formula 8

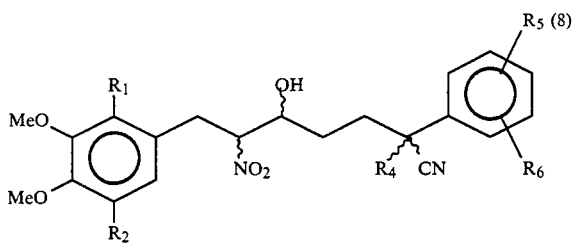

wherein $R_1$ and $R_2$ are each independently —H or lower alkoxy; $R_4$ is lower alkyl; and $R_5$ and $R_6$ are each —OCH$_3$, or together form —OCH$_2$O— or —OCH$_2$CH$_2$O—
to form a first resulting product; and then reacting a mixture of said first resulting product, a first alkanol (preferably 2-propanol), an inert solvent (preferably CH$_2$Cl$_2$), and a boron-based reducing agent (preferably NaBH$_4$) to produce a second resulting product; and heating a mixture of said second resulting product (at 30°-60° C.), ammonium formate, a noble metal catalyst (preferably 5% Pd/C), and a second alkanol (preferably methanol). A preferred species is the process wherein said compound of formula 8 is obtained by heating (at 40°-65° C.) a mixture of a third lower alkanol (preferably 2-propanol), a catalytic amount of a fluoride salt (preferably KF), a compound of formula 4, and a compound of formula 7:

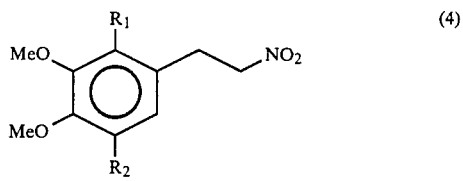

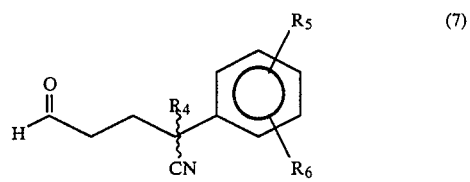

wherein $R_1$ and $R_2$ are each independently —H or lower alkoxy; $R_4$ is lower alkyl; and $R_5$ and $R_6$ are each —OCH$_3$, or together form —OCH$_2$O— or —OCH$_2$CH$_2$O—.

ADMINISTRATION AND FORMULATION

Another aspect of the present invention relates to pharmaceutical compositions useful in the treatment of cardiovascular diseases such as hypertension, congestive heart failure, angina, migraine, and vasospastic disorders, particularly in the treatment of hypertension in a mammalian subject, comprising a therapeutically effective amount of a compound of formula 1, or a pharmaceutically acceptable acid addition salt thereof, in admixture with a pharmaceutically acceptable nontoxic carrier. A therapeutically effective amount is that amount which, when administered to a mammal in need thereof, is sufficient to effect treatment, as defined above. Thus, the level of the drug in the formulation can vary from about 5 percent weight (%w) to about 95%w of the drug based on the total formulation and about 5%w to 95%w excipient. Preferably the drug is present at a level of about 10%w to about 70%w.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

Another aspect of the present invention relates to a method for treating cardiovascular diseases such as hypertension, congestive heart failure, angina, and vasospastic disorders in a mammalian subject (particularly a human) which method comprises administering a therapeutically effective amount of a compound of formula 1, or a pharmaceutically acceptable acid addition salt thereof, to a mammal in need thereof, especially a human.

In the practice of the above described method of the present invention a therapeutically effective amount of the compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 orally.

The formulation can be administered in a single unit dosage form for continuous treatment or in a single unit dosage form ad libitum when relief of symptoms is specifically required.

The Spontaneously Hypertensive Rat (SHR) assay is an accepted test for determining antihypertensive activity. See, e.g., J. Roba, et al., *Arch. Int. Pharmacodyn.*, 200, 182 (1972). The compounds of the invention exhibit antihypertensive activity in the SHR assay.

Other accepted tests for cardiovascular activity include rat aortic strip assays, ultrasonic two-dimensional echocardiography and anesthetized dog assays. See, e.g., P. Gueret, M.D., et al., *Circulation*, 62(6), 1308 (1980), and M Tripp. *American J. of Physiology*, 232(2), H173 (1977). The compounds of the invention demonstrate positive activity in these assays, also.

In view of the foregoing as well as in consideration of the degree of severity of the condition being treated, age of subject and so forth, all of which factors are routinely determinable by one skilled in the art, the effective dosage in accordance herewith can vary over a wide range. Generally, a therapeutically effective amount ranges from about 0.7 to about 7 mg/kg body weight per day and preferably, for example, for antihypertensive use, from about 0.8 to about 1.5 mg/kg body weight per day. In alternative terms, for an average 70 kg adult human subject, a therapeutically effective amount in accordance herewith would be, in preferred embodiments from about 50 mg to about 500 mg per day per subject, and preferably from about 60 mg to 100 mg per day per subject.

PREPARATION OF THE INVENTION

Compounds of the invention may be preferred by the methods illustrated in Schemes I, II, or III. Scheme I illustrates the presently preferred method of preparing compounds of formula 1. Scheme II illustrates a method for preparing optically pure diastereomers from commercially available starting materials. Scheme III illustrates an alternate method for preparing compounds of the invention.

SCHEME I

Step 1:

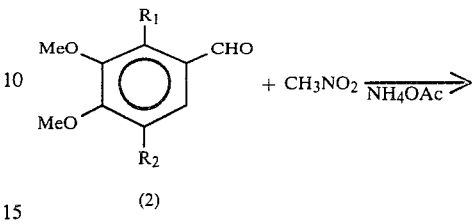

(2)

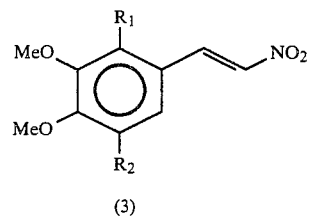

(3)

Step 2:

3 + NaBH$_4$, SiO$_2$/CH$_2$Cl$_2$ ⟶
i-PrOH

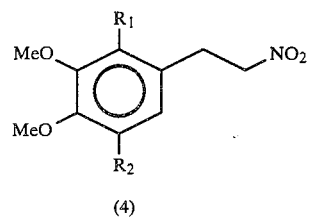

(4)

Step 3:

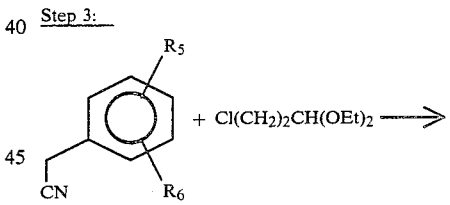

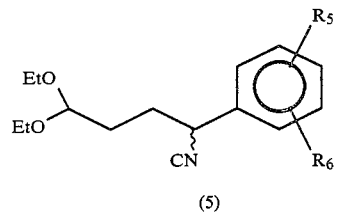

(5)

Step 4:

5 + NaH, R$_4$—X ⟶

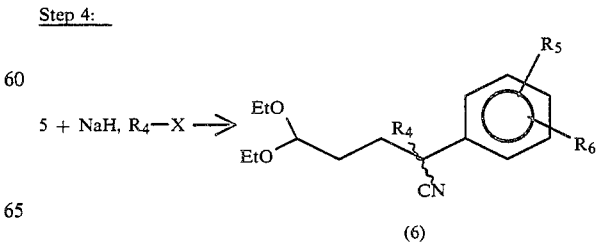

(6)

Step 5:

-continued
SCHEME I

6 + HCl ⟶

(7) [aldehyde structure with R4, CN, R5, R6]

Step 6:

4 + 7 + KF/i-PrOH ⟶

(8) [structure with OH, NO2, R1, R2, R4, CN, R5, R6]

Step 7:

8 + (RC)₂O, DMAP ⟶
(or RCOX)

$$\underset{\text{O}}{\overset{\text{O}}{\|}}$$

(9) [structure with OCR ester, NO2, R1, R2, R4, CN, R5, R6]

Step 8:

9 + NaBH₄/ROH ⟶

(10) [structure with NO2, R1, R2, R4, CN, R5, R6]

Step 9:

10 + HCO₂NH₄, 10% Pd/C ⟶

(11) [structure with NH2, R1, R2, R4, CN, R5, R6]

Step 10:

11 + (CH₂O)ₙ, HCO₂H ⟶

-continued
SCHEME I (1) [tetrahydroisoquinoline structure with MeO, MeO, R1, R2, N-Me, R4, CN, R5, R6]

SCHEME II

Step 1:

(12) [MeO, MeO-phenyl-CH2-CH(NH2)-CH2OH] + O(CO₂—t-Bu)₂ ⟶

(13) [same with NH-COO(t-Bu)]

Step 2:

13 + TsCl, DMAP ⟶

(14) [OTs derivative]

Step 3:

14 + CH₂=CH-MgBr/CuI ⟶

(15) [vinyl derivative]

Step 4:

15 + DAB ⟶

(16) [hydroxyl derivative with OH]

Step 5:

16 + MsCl, NaI ⟶

(17) [iodide derivative]

Step 6:

-continued
SCHEME II

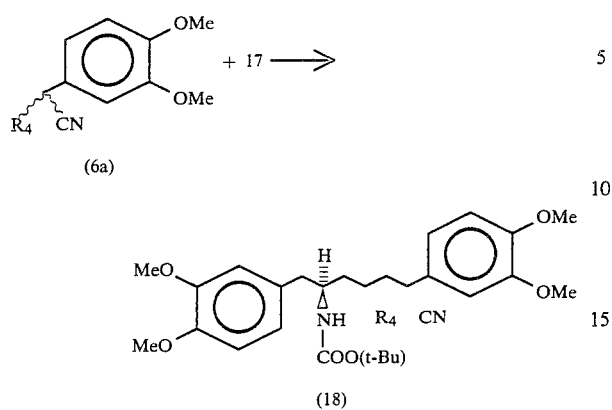

(6a)

(18)

Step 7:

18 + (1) HCO₂H
    (2) HCO₂COCH
    (3) chromatograph  ⟶

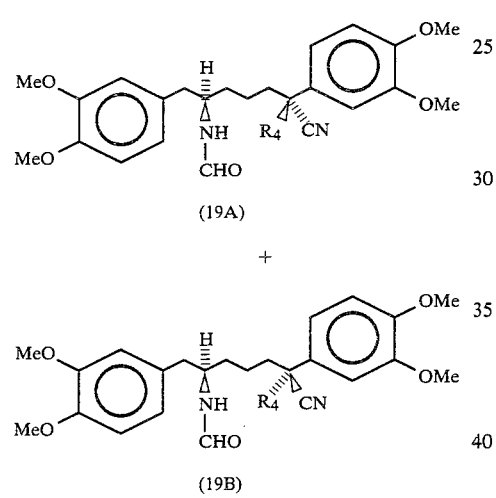

(19A)

+

(19B)

Step 8:

19A + (1) POCl₃
      (2) NaBH₄  ⟶

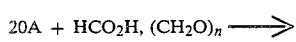

(20A)

Step 9a:

20A + HCO₂H, (CH₂O)ₙ ⟶

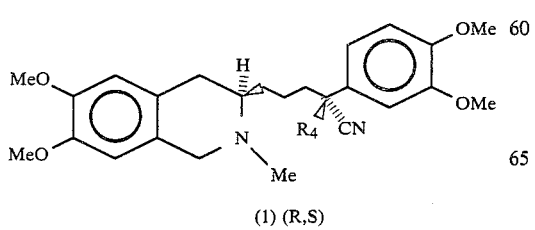

(1) (R,S)

-continued
SCHEME II

Step 9b:

20A + R₃—OTs ⟶

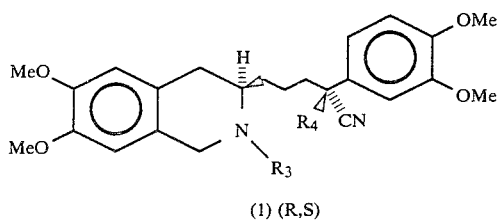

(1) (R,S)

SCHEME III

Step 1:

6a + Br⌒⌒Cl ⟶

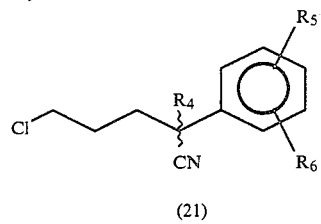

(21)

Step 2:

21 + NaI ⟶

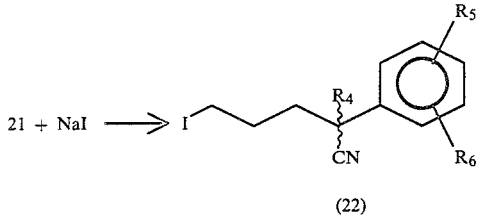

(22)

Step 3:

22 + 3-(3,4-dimethoxy-phenyl)propionic acid ⟶

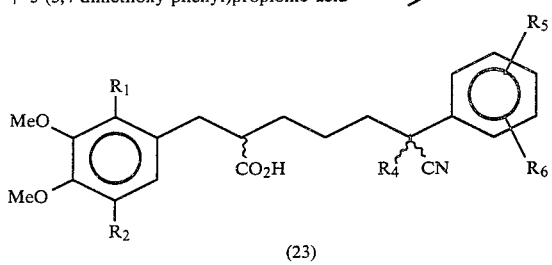

(23)

Step 4:

23 + (1) (φO)₂P(O)N₃, (2) NaBH₄ ⟶ 19

Step 5:

19 [as Scheme II, Steps 8-9] ⟶ 1

In the Schemes above, Ac refers to acetyl (CH₃CO—), LDA refers to lithium diisopropylamide, DMAP refers to 4-dimethylaminopyridine, X refers to halo, Ts refers to tosyl (p-toluenesulfonyl), DAB refers to disiamylborane, Ms refers to mesyl (methylsulfonyl), Me refers to methyl (CH₃—), Et refers to ethyl, i-Pr refers to isopropyl, t-Bu refers to tert-butyl, and φ refers to phenyl. Each R is independently lower alkyl, and R₁, $R_2$, $R_3$, $R_4$, $R_5$, and $R_6$ have the meanings described in the broadest description of the invention.

According to Scheme I, an optionally substituted dimethoxybenzaldehyde of formula 2, nitromethane and a catalytic amount of ammonium acetate (about 10 mol% per dimethoxybenzaldehyde) are heated to about 70°-100° C. for about 2-6 hours. The resulting product is precipitated from a mixture of water and isopropanol (about 7:1) to yield a nitrostyrene derivative of formula 3 (step 1). For example, 3,4-dimethoxybenzaldehyde is treated with $NH_4OAc$ and nitromethane to yield 3,4-dimethoxy-$\beta$-nitrostyrene (3). Alternatively, one can purchase 3,4-dimethoxy-$\beta$-nitrostyrene commercially.

The nitrostyrene derivative (3) is then cooled to about −10°-10° C., treated with silica gel, and reduced using 1.5-4 equivalents of a boron-based reducing agent, e.g., sodium borohydride, with 2-propanol and an inert solvent, e.g., $CH_2Cl_2$, at −10°-10° C. for 20-60 minutes to produce a nitrophenylethane derivative of formula 4 (step 2). For example, 3,4-dimethoxy-$\beta$-nitrostyrene (3) is treated with 2-propanol and $SiO_2$ in $CH_2Cl_2$ at 0°-10° C. for 20 minutes, followed by reduction with 1.5 eq $NaBH_4$ at 5° C. for 30 minutes to yield 2-(3,4-dimethoxyphenyl)nitroethane (4).

An optionally substituted phenylacetonitrile is then alkylated with an $\omega$-halopropionaldehyde acetal using a strong metallic base, in a polar, aprotic solvent. The desired phenylacetonitrile derivative is first deprotonated by adding about 1 eq of a strong metallic base, e.g., NaH, in a polar aprotic solvent at 15°-21° C. over 25-50 minutes. The resulting mixture is then stirred for 1-3 hours, and about 1 eq of 3-chloropropionaldehyde diethylacetal is added to yield a derivative of formula 5 (step 3). For example, 2-(3,4-dimethoxyphenyl)-acetonitrile in dimethyl formamide (DMF) is added to NaH at 18°-20° C. over a 30 minute period, stirred for one hour, and then treated with 3-chloropropionaldehyde diethylacetal in DMF to yield 2-(3,3-diethoxypropyl)-2-(3,4-dimethoxyphenyl)acetonitrile (5).

The resulting acetal derivative of formula 5 is then alkylated with about 1 eq of an alkylhalide using a strong metallic base and a catalytic amount of an iodide source, e.g., 2-iodopropane or NaI, in a polar aprotic solvent at about 10°-40° C. for 2-18 hours, followed by treatment with sufficient ice water to decompose excess base, to yield a dialkylated derivative of formula 6. For example, 2-(3,3-diethoxypropyl)-2-(3,4-dimethoxyphenyl)acetonitrile (5) in DMF is treated with a slight molar excess of 2-chloropropane (and 0.1-5 mol% 2-iodopropane) at 20° C., stirred for 10 minutes, then treated with 1 eq NaH in mineral oil and slowly heated to 40° C. After adding 200 mL ice water and purifying the product, 2-(3,3-diethoxypropyl)-2-(prop-2-yl)-2-(3,4-dimethoxyphenyl)acetonitrile (6) is obtained.

The resulting acetal intermediate of formula 6 is then hydrolyzed using a concentrated protic acid and a polar solvent at 30°-60° C. for 5-60 minutes (step 5). For example, 2-(3,3-diethoxypropyl)-2-(prop-2-yl)-3,4-dimethoxyphenyl)acetonitrile (6) is heated at 55° C. in THF/water (3:1) with concentrated HCl for 15 minutes to yield 1-(i-propyl)-1-(3,4-dimethoxyphenyl)-1-cyanobutanal (7).

The resulting intermediate of formula 7 is then condensed with the intermediate of formula 4 in the presence of a catalytic amount (about 0.1-5 mol%) of a fluoride salt, e.g., KF, and a base in an alcohol solvent at 40°-65° C. for 12-60 hours to produce a diaryl nitrohexanol of formula 8 (step 6). For example, 1-(prop-2-yl)-1-(3,4-dimethoxyphenyl)-1-cyanobutanal (7) is reacted with 2-(3,4-dimethoxyphenyl)nitroethane (4) in 2-propanol with a catalytic amount of KF to yield 1-(3,4-dimethoxyphenyl)-2-nitro-6-cyano-6-(prop-2-yl)-6-(3,4-dimethoxyphenyl)hexan-3-ol (8).

The resulting nitrohexanol intermediate of formula 8 is then acylated with an acylating agent, (for example acetic anhydride and a catalytic amount of dimethylaminopyridine (DMAP), or acetyl chloride) in an inert, aprotic, polar solvent for 20-120 minutes to produce a nitrohexanol acylate of formula 9 (step 7). For example, 1-(3,4-dimethoxyphenyl)-2-nitro-6-cyano-6-(prop-2-yl)-6-(3,4-dimethoxyphenyl)hexan-3-ol (8) is mixed with $Ac_2O$ and DMAP in $CH_2Cl_2$ for 40 minutes to yield O-acetyl-1-(3,4-dimethoxyphenyl)-2-nitro-6-cyano-6-(prop-2-yl)-6-(3,4-dimethoxyphenyl)hexan-3-ol (9).

The resulting nitrohexanol acetate of formula 9 is then reduced using a boron-based reducing agent, e.g., sodium borohydride, in a 2° or 3° alkanol at 25°-80° C. for 3-15 hours to produce a nitrohexane derivative of formula 10 (step 8). For example, O-acetyl-1-(3,4-dimethoxyphenyl)-2-nitro-6-cyano-6-(i-propyl)-6-(3,4-dimethoxyphenyl)hexan-3-ol (9) is heated with $NaBH_4$ in 2-propanol at reflux for 3-15 hours to yield 1-(3,4-dimethoxyphenyl)-2-nitro-6-cyano-6-(prop-2-yl)-6-(3,4-dimethoxyphenyl)hexane (10).

The intermediate of formula 10 is then reduced to an amine of formula 11, e.g., by treatment with ammonium formate in alcohol using a Pd/C catalyst at 30°-60° C. for 30 minutes to 48 hours (step 9). For example, 1-(3,4-dimethoxyphenyl)-2-nitro-6-cyano-6-(prop-2-yl)-6-(3,4-dimethoxyphenyl)hexane (10) is heated at reflux with $HCO_2NH_4$ in methanol over 5% Pd/C for about 24 hours to produce 1-(3,4-dimethoxyphenyl)-2-amino-6-cyano-6-(i-propyl)-6-(3,4-dimethoxyphenyl)hexane (11).

The intermediate of formula 11 is then cyclized and the amine methylated by reaction with a formaldehyde source, (e.g., formaldehyde, formalin, paraformaldehyde or the like) and formic acid at 70°-110° C. for 1-24 hours to yield a tetrahydroisoquinoline of formula 1 (step 10). For example, 1-(3,4-dimethoxyphenyl)-2-amino-6-cyano-6-(prop-2-yl)-6-(3,4-dimethoxyphenyl)hexane (11) is heated at 80°-100° C. with paraformaldehyde and formic acid for 2-8 hours to yield 3-[4-(3,4-dimethoxyphenyl)-4-isopropyl-4-cyanobutyl]-6,7-dimethoxy-N-methyl-1,2,3,4-tetrahydroisoquinoline (1) as a racemic mixture.

The free base of formula 1 may be converted to a pharmaceutically acceptable salt, if desired, by dissolving the base in a suitable solvent, such as an alcohol, and treating with the appropriate acid. For example, 3-[4-(3,4-dimethoxyphenyl)-4-isopropyl-4-cyanobutyl]-6,7-dimethoxy-N-methyl-1,2,3,4-tetrahydroisoquinoline (1) is dissolved in isopropanol, and HCl gas is bubbled through the solution. The solution is then saturated with ether to precipitate 3-[4-(3,4-dimethoxyphenyl)-4-isopropyl-4-cyanobutyl]-6,7-dimethoxy-N-methyl-1,2,3,4-tetrahydroisoquinoline·HCl.

In summary, compounds of formula 1 may be prepared via Scheme I by heating at 70°-110° C. for 1-24 hours a mixture of a compound of formula 11, a formaldehyde source, and formic acid.

Specific optical isomers may be prepared by the method illustrated in Scheme II. L-3,4-dimethoxyphenylalaninol (12) or another suitable phenylaminopropanol derivative is prepared as described by A. W.

Schrecker and J. L. Hartwell, *J. Am. Chem. Soc.*, 79, 3827 (1957). The amino group is then protected by reaction with di-t-butyldicarbonate to yield a carbamate derivative of formula 13 (step 1). For example, L-3,4-dimethoxyphenylalaninol (12) is heated at reflux in tetrahydrofuran (THF) for one hour with di-t-butyldicarbonate to yield 3-(3,4-dimethoxyphenyl)-L-2-(t-butoxycarbonylamino)propan-1-ol (13).

The hydroxy group is then converted to a suitable leaving group, e.g., by conversion to a tosylate (step 2). For example, 3-(3,4-dimethoxyphenyl)-L-2-(t-butoxycarbonylamino)propan-1-ol (13) is stirred at room temperature for 2 days with p-toluenesulfonyl chloride and a catalytic amount of DMAP in pyridine to yield 3-(3,4-dimethoxyphenyl)-L-2-(t-butoxycarbonylamino)-1-tosyloxypropane (14).

The tosylate of formula 14 is then treated with vinyl magnesium bromide and CuI in an inert solvent to produce the corresponding pent-1-ene derivative of formula 15 (step 3). For example, 3-(3,4-dimethoxyphenyl)-L-2-(t-butoxycarbonylamino)-1-tosyloxypropane (14) is treated with vinyl magnesium bromide and CuI in THF at −70° C. for ½ hour and allowed to warm to 0° C. to yield 5-(3,4-dimethoxyphenyl)-L-4-(t-butoxycarbonylamino)pent-1-ene (15).

The resulting pentene derivative is then converted to a pentanol derivative, e.g., by reaction with DAB in a suitable inert solvent (step 4). For example, 5-(3,4-dimethoxyphenyl)-L-4-(t-butoxycarbonylamino)-pent-1-ene (15) is added to DAB in THF at 0° C., stirred at room temperature for ½ hour, and treated with NaOH and $H_2O_2$ at room temperature for ½ hour to yield 5-(3,4-dimethoxyphenyl)-L-4-(t-butoxycarbonylamino)-pentan-1-ol (16).

The pentanol derivative is then converted to a pentyl iodide derivative of formula 17, e.g., by converting the pentanol derivative to a mesylate, followed by treatment of the mesylate with sodium iodide (step 5). For example, 5-(3,4-dimethoxyphenyl)-L-4-(t-butoxycarbonylamino)pentan-1-ol (16) is treated with $NEt_3$ and methanesulfonyl chloride in $CH_2Cl_2$ at 0° C. for 10 min. The product is separated, dissolved in acetone, and heated at reflux for ½ hour with NaI to yield 5-(3,4-dimethoxyphenyl)-L-4-(t-butoxycarbonylamino)-1-iodopentane (17).

An appropriate compound of formula 6 (see Scheme I) is treated with a strong base, e.g., LDA, in an inert solvent and is then reacted with the iodopentane derivative of formula 17 to form the aminohexane derivative of formula 18 (step 6). For example, (±)-2-(i-propyl)-2-(3,4-dimethoxyphenyl)acetonitrile (6) is deprotonated with LDA in THF at −70° C., then reacted with 5-(3,4-dimethoxyphenyl)-L-4-(t-butoxycarbonylamino)-1-iodopentane (17) to yield 1-(3,4-dimethoxyphenyl)-L-(2-t-butoxycarbonylamino)-(±)-6-cyano-6-(i-propyl)-6-(3,4-dimethoxyphenyl)hexane (18).

The resulting protected aminohexane derivative is then converted to a formylamino hexane derivative of formula 19 (step 7). For example, 1-(3,4-dimethoxyphenyl)-L-(2-t-butoxycarbonylamino)-(±)-6-cyano-6-(i-propyl)-6-(3,4-dimethoxyphenyl)hexane (18) is treated first with formic acid, then with formic-acetic anhydride to produce 1-(3,4-dimethoxyphenyl)-L-2-(formylamino)-(±)-6-cyano-6-(i-propyl)-6-(3,4-dimethoxyphenyl)hexane (19). The (+) and (−) isomers may then be separated by medium pressure chromatography using ethyl acetate as the solvent. The (−) isomer, 1-(3,4-dimethoxyphenyl)-L-2-(formylamino)-(−)-6-cyano-6-(i-propyl)-6-(3,4-dimethoxyphenyl)hexane (19A), elutes first, followed by 1-(3,4-dimethoxyphenyl)-L-2-(formylamino)-(+)-6-cyano-6-(i-propyl)-6-(3,4-dimethoxyphenyl)hexane (19B).

The formylaminohexane derivative is then cyclized to a tetrahydroisoquinoline of formula 20, e.g., by treatment with phosphorous oxychloride followed by $NaBH_4$ (step 8). For example, 1-(3,4-dimethoxyphenyl)-L-2-(formylamino)-(−)-6-cyano-6-(i-propyl)-6-(3,4-dimethoxyphenyl)hexane (19A) is treated with $POCl_3$ in $CH_3CN$, followed by reaction with $NaBH_4$ in ethanol to produce L-(−)-3-[4-(3,4-dimethoxyphenyl)-4-isopropyl-4-cyanobutyl]-6,7-dimethoxy-1,2,3,4-tetrahydroisoquinoline (20A).

The resulting isoquinoline derivative of formula 20 is then N-alkylated, e.g., using paraformaldehyde in formic acid to produce a compound of formula 1. For example, L-(−)-3-[4-(3,4-dimethoxyphenyl)-4-isopropyl-4-cyanobutyl]-6,7-dimethoxy-1,2,3,4-tetrahydroisoquinoline (20A) is reacted with paraformaldehyde in formic acid to produce L-(−)-3-[4-(3,4-dimethoxyphenyl)-4-isopropyl-4-cyanobutyl]-6,7-dimethoxy-N-methyl-1,2,3,4-tetrahydroisoquinoline (1). Alternatively, one can alkylate an intermediate of formula 19 using a strong base and an alkylating agent of the form $R_3$-L, where L is an appropriate leaving group, such as tosyl. For example, L-(−)-3-[4-(3,4-dimethoxyphenyl)-4-isopropyl-4-cyanobutyl]-6,7-dimethoxy-1,2,3,4-tetrahydroisoquinoline (20A) is reacted with LDA and propyltosylate to produce L-(−)-3-[4-(3,4-dimethoxyphenyl)-4-isopropyl-4-cyanobutyl]-6,7-dimethoxy-N-propyl-1,2,3,4-tetrahydroisoquinoline (1).

Alternatively, one may prepare compounds of the invention via the procedures of Scheme III. In the first step, a derivative of formula 6a (see Scheme II) is alkylated with a 1,3-dihalopropane using a strong base in a suitable aprotic solvent to produce a derivative of formula 21 (step 1). For example, 2-(3,4-dimethoxyphenyl)-2-isopropylacetonitrile is treated with sodium amide in toluene and 1-bromo-3-chloropropane to produce 2-(3,4-dimethoxyphenyl)-2-isopropyl-2-(3-chloropropyl)-acetonitrile (21).

The chloro derivative of formula 21 is then converted to an iodide derivative of formula 22 by treatment with an appropriate salt (step 2). For example, 2-(3,4-dimethoxyphenyl)-2-isopropyl-2-(3-chloropropyl)acetonitrile (21) is treated with NaI in acetone at reflux to yield 2-(3,4-dimethoxyphenyl)-2-isopropyl-2-(3-iodopropyl)acetonitrile (22).

The iodo derivative of formula 22 is then reacted with a 3-(3,4-dimethoxyphenyl)propionic acid derivative (optionally substituted at phenyl positions 2 and/or 5) in the presence of a strong base to produce a derivative of formula 23 (step 3). For example, 2-(3,4-dimethoxyphenyl)-2-isopropyl-2-(3-iodopropyl)acetonitrile (22) is reacted with lithium diisopropylamide, hexamethylphosphoramide, and 3-(3,4-dimethoxyphenyl)propionic acid in THF to yield 1-(3,4-dimethoxyphenyl)-6-cyano-6-(i-propyl)-6-(3,4-dimethoxyphenyl)hexan-2-oic acid (23).

The derivative of formula 23 is then converted to a formamide derivative of formula 19, e.g., by treating with diphenylphosphoryl azide and base, followed by treatment with sodium borohydride. For example, 1-(3,4-dimethoxyphenyl)-6-cyano-6-(i-propyl)-6-(3,4-dimethoxyphenyl)hexan-2-oic acid (23) is treated with triethylamine and diphenylphosphoryl azide in THF, then reacted with $NaBH_4$ in dimethoxyethane to yield 1-(3,4-dimethoxyphenyl)-2-(formylamino)-6-cyano-6-(i-propyl)-6-(3,4-dimethoxyphenyl)hexane (19). The intermediates of formula 19 may be separated into diastereomeric pairs of silica gel chromatography using ethyl acetate-hexane (4:1) as an eluent. The intermediates of formula 19 may be converted to compounds of formula 1 by the procedures of Scheme II, steps 8-9.

The free base of formula 1 may be converted to a pharmaceutically acceptable salt, if desired, by dissolving the base in a suitable solvent, such as an alcohol, and treating with the appropriate acid. For example, L-(−)-3-[4-(3,4-dimethoxyphenyl)-4-isopropyl-4-cyanobutyl]-6,7-dimethoxy-N-methyl-1,2,3,4-tetrahydroisoquinoline (1) is dissolved in isopropanol, and HCl gas is bubbled through the solution. The solution is then saturated with ether to precipitate L-(−)-3-[4-(3,4-dimethoxyphenyl)-4-isopropyl-4-cyanobutyl]-6,7-dimethoxy-N-methyl-1,2,3,4-tetrahydroisoquinoline·HCl.

The following Preparations and Examples are intended as further illustrations of the invention, and are not intended as limitations on the scope thereof.

PREPARATION 1

(Intermediates of Formula 3)

(A) A mixture of 3,4-dimethoxybenzaldehyde (2, 100 g, 0.60 mol, obtainable through Aldrich Chemical Co.), ammonium acetate (10 g, Aldrich), and nitromethane (800 mL) was heated over a steam bath for 2.5 hours. The mixture was then cooled to room temperature, mixed with isopropanol (500 mL), and slowly added to water (3.5 L) to precipitate the product, 3,4-dimethoxy-β-nitrostyrene (3, 114 g, m.p. 142°-143° C.).

(B) Similarly, proceeding as in part (A) above but substituting 3,4,5-trimethoxybenzaldehyde, 2,3,4-trimethoxybenzaldehyde, 2,3,4,5-tetramethoxybenzaldehyde, 3,4-dimethoxy-2,5-diethoxybenzaldehyde, or 3,4-dimethoxy-2,5-dipentoxybenzaldehyde for 3,4-dimethoxybenzaldehyde, the following compounds are prepared:
  3,4,5-trimethoxyphenyl-β-nitrostyrene;
  2,3,4-trimethoxyphenyl-β-nitrostyrene;
  2,3,4,5-tetramethoxyphenyl-β-nitrostyrene;
  3,4-dimethoxy-2,5-diethoxyphenyl-β-nitrostyrene; and
  3,4-dimethoxy-2,5-dipentoxyphenyl-β-nitrostyrene.

PREPARATION 2

(Intermediates of Formula 4)

(A) A mixture of 3,4-dimethoxy-β-nitrostyrene (3, 140 g, 0.67 mol) 3° C.), methylene chloride (3.2 L), and isopropanol (2.0 L) was cooled to 5° C. and treated with silica gel (1.32 Kg, 70–230 mesh, EM Reagents). After stirring at 5° C. for 20 minutes, NaBH₄ (88.6 g, 2.34 mol, Alfa Chemicals) was added over 30 minutes, followed by another 30 minutes of stirring at 5° C. The reaction was then quenched by adding 10% aqueous HCl (280 mL). The silica gel was filtered off and washed with CH₂Cl₂ (2×150 mL). The combined filtrates were washed with water (1.0 L) followed by brine (1.0 L). The organic layer was removed in vacuo to yield 2-(3,4-dimethoxyphenyl)-1-nitroethane (4, 132 g, m.p. 50°-52° C.) as a pale yellow oil which solidified on standing.

(B) Similarly, proceeding as in part (A) above but substituting the compounds prepared in Preparation 1(B) for 3,4-dimethoxy-β-nitrostyrene, the following compounds are prepared:
  2-(3,4,5-trimethoxyphenyl)-1-nitroethane;
  2-(2,3,4-trimethoxyphenyl)-1-nitroethane;
  2-(2,3,4,5-tetramethoxyphenyl)-1-nitroethane;
  2-(3,4-dimethoxy-2,5-diethoxyphenyl)-1-nitroethane; and
  2-(3,4-dimethoxy-2,5-dipentoxyphenyl)-1-nitroethane.

PREPARATION 3

(Intermediates of Formula 5)

(A) A mixture of 2-(3,4-dimethoxyphenyl)acetonitrile (5, 55 g, 0.31 mol, Aldrich) in dimethylformamide (DMF, 200 mL) in an addition funnel was added to a mixture of NaH (50% NaH in mineral oil, 15.84 g, 0.33 mol) in DMF (50 mL) over 30 minutes at 18°-20° C. After stirring for one hour, a solution of 3-chloropropanal diethylacetal (53 mL, 0.316 mol, Aldrich) in DMF (50 mL) was added and stirred for about 3 hours to produce 2-(3,4-dimethoxyphenyl)-2-(3,3-diethoxypropyl)acetonitrile (5) which was used in the next step without further treatment.

(B) Similarly, proceeding as in part (A) above but substituting 2-nitriloethylbenzo-1,4-dioxan or 2-nitriloethylbenzo-1,3-dioxole for 2-(3,4-dimethoxyphenyl)acetonitrile, the following compounds are prepared:
  2-(1,3-benzodioxol-2-yl)-2-(3,3-diethoxypropyl)acetonitrile; and
  2-(1,4-benzodioxan-2-yl)-2-(3,3-diethoxypropyl)acetonitrile.

PREPARATION 4

(Intermediates of Formula 6)

(A) To the product mixture resulting from Preparation 3(A) above was added in one portion a solution of 2-chloropropane (39.5 mL, 0.43 mol) and 2-iodopropane (0.04 mL) in DMF (50 mL). After stirring for 10 minutes, a mixture of NaH in mineral oil (50%, 15.9 g, 0.33 mol) was added, and the resulting mixture heated to 40° C. and stirred for 18 hours. The mixture was then cooled to room temperature, and ice water (200 mL) added. The mixture was extracted with hexane (500 mL) to remove the mineral oil, which was then discarded. The aqueous DMF layer was diluted with water (800 mL) and extracted with ethyl acetate (3×500 mL). The ethyl acetate extract was evaporated to yield 2-(3,4-dimethoxyphenyl)-2-(3,3-diethoxypropyl)-2-isopropylacetonitrile as an oil (97.6 g, b.p. 164°-166° C./0.2 mmHg, MS m/e 349(M+)).

(B) Similarly, proceeding as in part (A) above but substituting methylchloride, chloroethane, 2-chlorobutane, or 3-bromopentane for 2-chloropropane, the following compounds are prepared:
  2-(3,4-dimethoxyphenyl)-2-(3,3-diethoxypropyl)-2-methylacetonitrile;
  2-(3,4-dimethoxyphenyl)-2-(3,3-diethoxypropyl)-2-ethylacetonitrile;
  2-(3,4-dimethoxyphenyl)-2-(3,3-diethoxypropyl)-2-(but-2-yl)acetonitrile; and
  2-(3,4-dimethoxyphenyl)-2-(3,3-diethoxypropyl)-2-(pent-3-yl)acetonitrile.

(C) Similarly, proceeding as in parts (A-B) above but substituting the compounds prepared in Preparation 3(B) for the starting material, the following compounds are prepared:
  2-(1,3-benzodioxol-2-yl)-2-(3,3-diethoxypropyl)-2-methylacetonitrile;
  2-(1,3-benzodioxol-2-yl)-2-(3,3-diethoxypropyl)-2-ethylacetonitrile;

2-(1,3-benzodioxol-2-yl)-2-(3,3-diethoxypropyl)-2-isopropylacetonitrile;

2-(1,3-benzodioxol-2-yl)-2-(3,3-diethoxypropyl)-2-(but-2-yl)acetonitrile;

2-(1,3-benzodioxol-2-yl)-2-(3,3-diethoxypropyl)-2-(pent-3-yl)acetonitrile;

2-(1,4-benzodioxan-2-yl)-2-(3,3-diethoxypropyl)-2-methylacetonitrile;

2-(1,4-benzodioxan-2-yl)-2-(3,3-diethoxypropyl)-2-ethylacetonitrile;

2-(1,4-benzodioxan-2-yl)-2-(3,3-diethoxypropyl)-2-isopropylacetonitrile;

2-(1,4-benzodioxan-2-yl)-2-(3,3-diethoxypropyl)-2-(but-2-yl)-acetonitrile; and 2-(1,4-benzodioxan-2-yl)-2-(3,3-diethoxypropyl)-2-(pent-3-yl)acetonitrile.

PREPARATION 5

(Intermediates of Formula 7)

(A) A solution of 2-(3,4-dimethoxyphenyl)-2-(3,3-diethoxypropyl)-2-isopropylacetonitrile (97.6 g, 0.28 mol) in THF (1.4 L) and water (550 mL) was prepared at 55° C. Concentrated HCl (66 mL) was then added over 15 minutes, and the mixture stirred for an additional 30 minutes. The THF was then removed in vacuo, and the aqueous remainder extracted with $CH_2Cl_2$ (1.3 L) and water (500 mL). The organic layer was separated, washed with saturated aqueous $NaHCO_3$ (500 mL), and evaporated to yield 2-(3,4-dimethoxyphenyl)-2-(3-oxopropyl)-2-isopropylacetonitrile (7, 71.7 g, MS m/e 275 (M+)) as a thick oil.

(B) Similarly, proceeding as in part (A) above but substituting the compounds prepared in Preparation 4(B) for 2-(3,4-dimethoxyphenyl)-2-(3,3-diethoxypropyl)-2-isopropylacetonitrile, the following compounds are prepared:

2-(3-oxopropyl)-2-(3,4-dimethoxyphenyl)-2-methylacetonitrile;

2-(3-oxopropyl)-2-(3,4-dimethoxyphenyl)-2-ethylacetonitrile;

2-(3-oxopropyl)-2-(3,4-dimethoxyphenyl)-2-(but-2-yl)acetonitrile;

2-(3-oxopropyl)-2-(3,4-dimethoxyphenyl)-2-(pent-3-yl)acetonitrile;

2-(3-oxopropyl)-2-(1,3-benzodioxol-2-yl)-2-methylacetonitrile;

2-(3-oxopropyl)-2-(1,3-benzodioxol-2-yl)-2-ethylacetonitrile;

2-(3-oxopropyl)-2-(1,3-benzodioxol-2-yl)-2-isopropylacetonitrile;

2-(3-oxopropyl)-2-(1,3-benzodioxol-2-yl)-2-(but-2-yl)-acetonitrile;

2-(3-oxopropyl)-2-(1,3-benzodioxol-2-yl)-2-(pent-3-yl)acetonitrile;

2-(3-oxopropyl)-2-(1,4-benzodioxan-2-yl)-2-methylacetonitrile;

2-(3-oxopropyl)-2-(1,4-benzodioxan-2-yl)-2-ethylacetonitrile;

2-(3-oxopropyl)-2-(1,4-benzodioxan-2-yl)-2-isopropylacetonitrile;

2-(3-oxopropyl)-2-(1,4-benzodioxan-2-yl)-2-(but-2-yl)-acetonitrile; and 2-(3-oxopropyl)-2-(1,4-benzodioxan-2-yl)-2-(pent-3-yl)acetonitrile.

PREPARATION 6

(Intermediates of Formula 8)

(A) A mixture of 2-(3,4-dimethoxyphenyl)-1-nitroethane (4, 135 g, 0.64 mol), 2-(3,4-dimethoxyphenyl)-2-(3-oxopropyl)-2-isopropylacetonitrile (7, 156 g, 0.57 mol) and KF (19.3 g, anhydrous, Aldrich) in 2-propanol (2.0 L) was heated to 50°–55° C. for about 40 hours. The mixture was then cooled to room temperature and the isopropanol removed in vacuo. The residue was dissolved in $CH_2Cl_2$ (1.6 L) and filtered through Celite (50 g). The filtrate was extracted with saturated aqueous $NaHCO_3$ (2×500 mL), the organic layer evaporated, and the product recrystallized from ethyl acetate-hexane (1:1) to yield 1-(3,4-dimethoxyphenyl)-2-nitro-6-cyano-6-(i-propyl)-6-(3,4-dimethoxyphenyl)-hexan-3-ol (8, 205 g, m.p. 171°–173° C., MS m/e 486(M+)).

(B) Similarly, proceeding as in part (A) above but substituting the compounds prepared in Preparation 5(B) for 2-(3,4-dimethoxyphenyl)-2-(3-oxopropyl)-2-isopropylacetonitrile (7), the following compounds are prepared:

1-(3,4-dimethoxyphenyl)-2-nitro-6-cyano-6-(methyl)-6-(3,4-dimethoxyphenyl)hexan-3-ol;

1-(3,4-dimethoxyphenyl)-2-nitro-6-cyano-6-(ethyl)-6-(3,4-dimethoxyphenyl)hexan-3-ol;

1-(3,4-dimethoxyphenyl)-2-nitro-6-cyano-6-(but-2-yl)-6-(3,4-dimethoxyphenyl)hexan-3-ol;

1-(3,4-dimethoxyphenyl)-2-nitro-6-cyano-6-(pent-3-yl)-6-(3,4-dimethoxyphenyl)hexan-3-ol;

1-(1,3-benzodioxol-2-yl)-2-nitro-6-cyano-6-(methyl)-6-(3,4-dimethoxyphenyl)hexan-3-ol;

1-(1,3-benzodioxol-2-yl)-2-nitro-6-cyano-6-(ethyl)-6-(3,4-dimethoxyphenyl)hexan-3-ol;

1-(1,3-benzodioxol-2-yl)-2-nitro-6-cyano-6-(prop-2-yl)-6-(3,4-dimethoxyphenyl)hexan-3-ol;

1-(1,3-benzodioxol-2-yl)-2-nitro-6-cyano-6-(but-2-yl)-6-(3,4-dimethoxyphenyl)hexan-3-ol;

1-(1,3-benzodioxol-2-yl)-2-nitro-6-cyano-6-(pent-3-yl)-6-(3,4-dimethoxyphenyl)hexan-3-ol;

1-(1,4-benzodioxan-2-yl)-2-nitro-6-cyano-6-(methyl)-6-(3,4-dimethoxyphenyl)hexan-3-ol;

1-(1,4-benzodioxan-2-yl)-2-nitro-6-cyano-6-(ethyl)-6-(3,4-dimethoxyphenyl)hexan-3-ol;

1-(1,4-benzodioxan-2-yl)-2-nitro-6-cyano-6-(prop-2-yl)-6-(3,4-dimethoxyphenyl)hexan-3-ol;

1-(1,4-benzodioxan-2-yl)-2-nitro-6-cyano-6-(but-2-yl)-6-(3,4-dimethoxyphenyl)hexan-3-ol; and 1-(1,4-benzodioxan-2-yl)-2-nitro-6-cyano-6-(pent-3-yl)-6-(3,4-dimethoxyphenyl)hexan-3-ol.

(C) Similarly, proceeding as in parts (A-B) above but substituting the compounds prepared in Preparation 2(B) for 2-(3,4-dimethoxyphenyl)-1-nitroethane (4), the following compounds are prepared:

1-(3,4-dimethoxyphenyl)-2-nitro-6-cyano-6-(methyl)-6-(3,4,5-trimethoxyphenyl)hexan-3-ol;

1-(3,4-dimethoxyphenyl)-2-nitro-6-cyano-6-(ethyl)-6-(3,4,5-trimethoxyphenyl)hexan-3-ol;

1-(3,4-dimethoxyphenyl)-2-nitro-6-cyano-6-(prop-2-yl)-6-(3,4,5-trimethoxyphenyl)hexan-3-ol;

1-(3,4-dimethoxyphenyl)-2-nitro-6-cyano-6-(but-2-yl)-6-(3,4,5-trimethoxyphenyl)hexan-3-ol;

1-(3,4-dimethoxyphenyl)-2-nitro-6-cyano-6-(pent-3-yl)-6-(3,4,5-trimethoxyphenyl)hexan-3-ol;

1-(1,3-benzodioxol-2-yl)-2-nitro-6-cyano-6-(methyl)-6-(3,4,5-trimethoxyphenyl)hexan-3-ol;

1-(1,3-benzodioxol-2-yl)-2-nitro-6-cyano-6-(ethyl)-6-(3,4,5-trimethoxyphenyl)hexan-3-ol;
1-(1,3-benzodioxol-2-yl)-2-nitro-6-cyano-6-(prop-2-yl)-6-(3,4,5-trimethoxyphenyl)hexan-3-ol;
1-(1,3-benzodioxol-2-yl)-2-nitro-6-cyano-6-(but-2-yl)-6-(3,4,5-trimethoxyphenyl)hexan-3-ol;
1-(1,3-benzodioxol-2-yl)-2-nitro-6-cyano-6-(pent-3-yl)-6-(3,4,5-trimethoxyphenyl)hexan-3-ol;
1-(1,4-benzodioxan-2-yl)-2-nitro-6-cyano-6-(methyl)-6-(3,4,5-trimethoxyphenyl)hexan-3-ol;
1-(1,4-benzodioxan-2-yl)-2-nitro-6-cyano-6-(ethyl)-6-(3,4,5-trimethoxyphenyl)hexan-3-ol;
1-(1,4-benzodioxan-2-yl)-2-nitro-6-cyano-6-(prop-2-yl)-6-(3,4,5-trimethoxyphenyl)hexan-3-ol;
1-(1,4-benzodioxan-2-yl)-2-nitro-6-cyano-6-(but-2-yl)-6-(3,4,5-trimethoxyphenyl)hexan-3-ol;
1-(1,4-benzodioxan-2-yl)-2-nitro-6-cyano-6-(pent-3-yl)-6-(3,4,5-trimethoxyphenyl)hexan-3-ol;
1-(3,4-dimethoxyphenyl)-2-nitro-6-cyano-6-(methyl)-6-(2,3,4-trimethoxyphenyl)hexan-3-ol;
1-(3,4-dimethoxyphenyl)-2-nitro-6-cyano-6-(ethyl)-6-(2,3,4-trimethoxyphenyl)hexan-3-ol;
1-(3,4-dimethoxyphenyl)-2-nitro-6-cyano-6-(prop-2-yl)-6-(2,3,4-trimethoxyphenyl)hexan-3-ol;
1-(3,4-dimethoxyphenyl)-2-nitro-6-cyano-6-(but-2-yl)-6-(2,3,4-trimethoxyphenyl)hexan-3-ol;
1-(3,4-dimethoxyphenyl)-2-nitro-6-cyano-6-(pent-3-yl)-6-(2,3,4-trimethoxyphenyl)hexan-3-ol;
1-(1,3-benzodioxol-2-yl)-2-nitro-6-cyano-6-(methyl)-6-(2,3,4-trimethoxyphenyl)hexan-3-ol;
1-(1,3-benzodioxol-2-yl)-2-nitro-6-cyano-6-(ethyl)-6-(2,3,4-trimethoxyphenyl)hexan-3-ol;
1-(1,3-benzodioxol-2-yl)-2-nitro-6-cyano-6-(prop-2-yl)-6-(2,3,4-trimethoxyphenyl)hexan-3-ol;
1-(1,3-benzodioxol-2-yl)-2-nitro-6-cyano-6-(but-2-yl)-6-(2,3,4-trimethoxyphenyl)hexan-3-ol;
1-(1,3-benzodioxol-2-yl)-2-nitro-6-cyano-6-(pent-3-yl)-6-(2,3,4-trimethoxyphenyl)hexan-3-ol;
1-(1,4-benzodioxan-2-yl)-2-nitro-6-cyano-6-(methyl)-6-(2,3,4-trimethoxyphenyl)hexan-3-ol;
1-(1,4-benzodioxan-2-yl)-2-nitro-6-cyano-6-(ethyl)-6-(2,3,4-trimethoxyphenyl)hexan-3-ol;
1-(1,4-benzodioxan-2-yl)-2-nitro-6-cyano-6-(prop-2-yl)-6-(2,3,4-trimethoxyphenyl)hexan-3-ol;
1-(1,4-benzodioxan-2-yl)-2-nitro-6-cyano-6-(but-2-yl)-6-(2,3,4-trimethoxyphenyl)hexan-3-ol;
1-(1,4-benzodioxan-2-yl)-2-nitro-6-cyano-6-(pent-3-yl)-6-(2,3,4-trimethoxyphenyl)hexan-3-ol;
1-(3,4-dimethoxyphenyl)-2-nitro-6-cyano-6-(methyl)-6-(2,3,4,5-tetramethoxyphenyl)hexan-3-ol;
1-(3,4-dimethoxyphenyl)-2-nitro-6-cyano-6-(ethyl)-6-(2,3,4,5-tetramethoxyphenyl)hexan-3-ol;
1-(3,4-dimethoxyphenyl)-2-nitro-6-cyano-6-(prop-2-yl)-6-(2,3,4,5-tetramethoxyphenyl)hexan-3-ol;
1-(3,4-dimethoxyphenyl)-2-nitro-6-cyano-6-(but-2-yl)-6-(2,3,4,5-tetramethoxyphenyl)hexan-3-ol;
1-(3,4-dimethoxyphenyl)-2-nitro-6-cyano-6-(pent-3-yl)-6-(2,3,4,5-tetramethoxyphenyl)hexan-3-ol;
1-(1,3-benzodioxol-2-yl)-2-nitro-6-cyano-6-(methyl)-6-(2,3,4,5-tetramethoxyphenyl)hexan-3-ol;
1-(1,3-benzodioxol-2-yl)-2-nitro-6-cyano-6-(ethyl)-6-(2,3,4,5-tetramethoxyphenyl)hexan-3-ol;
1-(1,3-benzodioxol-2-yl)-2-nitro-6-cyano-6-(prop-2-yl)-6-(2,3,4,5-tetramethoxyphenyl)hexan-3-ol;
1-(1,3-benzodioxol-2-yl)-2-nitro-6-cyano-6-(but-2-yl)-6-(2,3,4,5-tetramethoxyphenyl)hexan-3-ol;
1-(1,3-benzodioxol-2-yl)-2-nitro-6-cyano-6-(pent-3-yl)-6-(2,3,4,5-tetramethoxyphenyl)hexan-3-ol;
1-(1,4-benzodioxan-2-yl)-2-nitro-6-cyano-6-(methyl)-6-(2,3,4,5-tetramethoxyphenyl)hexan-3-ol;
1-(1,4-benzodioxan-2-yl)-2-nitro-6-cyano-6-(ethyl)-6-(2,3,4,5-tetramethoxyphenyl)hexan-3-ol;
1-(1,4-benzodioxan-2-yl)-2-nitro-6-cyano-6-(prop-2-yl)-6-(2,3,4,5-tetramethoxyphenyl)hexan-3-ol;
1-(1,4-benzodioxan-2-yl)-2-nitro-6-cyano-6-(but-2-yl)-6-(2,3,4,5-tetramethoxyphenyl)hexan-3-ol;
1-(1,4-benzodioxan-2-yl)-2-nitro-6-cyano-6-(pent-3-yl)-6-(2,3,4,5-tetramethoxyphenyl)hexan-3-ol;
1-(3,4-dimethoxyphenyl)-2-nitro-6-cyano-6-(methyl)-6-(3,4-dimethoxy-2,5-diethoxyphenyl)hexan-3-ol;
1-(3,4-dimethoxyphenyl)-2-nitro-6-cyano-6-(ethyl)-6-(3,4-dimethoxy-2,5-diethoxyphenyl)hexan-3-ol;
1-(3,4-dimethoxyphenyl)-2-nitro-6-cyano-6-(but-2-yl)-6-(3,4-dimethoxy-2,5-diethoxyphenyl)hexan-3-ol;
1-(3,4-dimethoxyphenyl)-2-nitro-6-cyano-6-(pent-3-yl)-6-(3,4-dimethoxy-2,5-diethoxyphenyl)hexan-3-ol;
1-(1,3-benzodioxol-2-yl)-2-nitro-6-cyano-6-(methyl)-6-(3,4-dimethoxy-2,5-diethoxyphenyl)hexan-3-ol;
1-(1,3-benzodioxol-2-yl)-2-nitro-6-cyano-6-(ethyl)-6-(3,4-dimethoxy-2,5-diethoxyphenyl)hexan-3-ol;
1-(1,3-benzodioxol-2-yl)-2-nitro-6-cyano-6-(prop-2-yl)-6-(3,4-dimethoxy-2,5-diethoxyphenyl)hexan-3-ol;
1-(1,3-benzodioxol-2-yl)-2-nitro-6-cyano-6-(but-2-yl)-6-(3,4-dimethoxy-2,5-diethoxyphenyl)hexan-3-ol;
1-(1,3-benzodioxol-2-yl)-2-nitro-6-cyano-6-(pent-3-yl)-6-(3,4-dimethoxy-2,5-diethoxyphenyl)hexan-3-ol;
1-(1,4-benzodioxan-2-yl)-2-nitro-6-cyano-6-(methyl)-6-(3,4-dimethoxy-2,5-diethoxyphenyl)hexan-3-ol;
1-(1,4-benzodioxan-2-yl)-2-nitro-6-cyano-6-(ethyl)-6-(3,4-dimethoxy-2,5-diethoxyphenyl)hexan-3-ol;
1-(1,4-benzodioxan-2-yl)-2-nitro-6-cyano-6-(prop-2-yl)-6-(3,4-dimethoxy-2,5-diethoxyphenyl)hexan-3-ol;
1-(1,4-benzodioxan-2-yl)-2-nitro-6-cyano-6-(but-2-yl)-6-(3,4-dimethoxy-2,5-diethoxyphenyl)hexan-3-ol;
1-(1,4-benzodioxan-2-yl)-2-nitro-6-cyano-6-(pent-3-yl)-6-(3,4-dimethoxy-2,5-diethoxyphenyl)hexan-3-ol;
1-(3,4-dimethoxyphenyl)-2-nitro-6-cyano-6-(methyl)-6-(3,4-dimethoxy-2,5-dipentoxyphenyl)hexan-3-ol;
1-(3,4-dimethoxyphenyl)-2-nitro-6-cyano-6-(ethyl)-6-(3,4-dimethoxy-2,5-dipentoxyphenyl)hexan-3-ol;
1-(3,4-dimethoxyphenyl)-2-nitro-6-cyano-6-(prop-2-yl)-6-(3,4-dimethoxy-2,5-dipentoxyphenyl)hexan-3-ol;
1-(3,4-dimethoxyphenyl)-2-nitro-6-cyano-6-(but-2-yl)-6-(3,4-dimethoxy-2,5-dipentoxyphenyl)hexan-3-ol;
1-(3,4-dimethoxyphenyl)-2-nitro-6-cyano-6-(pent-3-yl)-6-(3,4-dimethoxy-2,5-dipentoxyphenyl)hexan-3-ol;
1-(1,3-benzodioxol-2-yl)-2-nitro-6-cyano-6-(methyl)-6-(3,4-dimethoxy-2,5-dipentoxyphenyl)hexan-3-ol;
1-(1,3-benzodioxol-2-yl)-2-nitro-6-cyano-6-(ethyl)-6-(3,4-dimethoxy-2,5-dipentoxyphenyl)hexan-3-ol;
1-(1,3-benzodioxol-2-yl)-2-nitro-6-cyano-6-(prop-2-yl)-6-(3,4-dimethoxy-2,5-dipentoxyphenyl)hexan-3-ol;
1-(1,3-benzodioxol-2-yl)-2-nitro-6-cyano-6-(but-2-yl)-6-(3,4-dimethoxy-2,5-dipentoxyphenyl)hexan-3-ol;
1-(1,3-benzodioxol-2-yl)-2-nitro-6-cyano-6-(pent-3-yl)-6-(3,4-dimethoxy-2,5-dipentoxyphenyl)hexan-3-ol;
1-(1,4-benzodioxan-2-yl)-2-nitro-6-cyano-6-(methyl)-6-(3,4-dimethoxy-2,5-dipentoxyphenyl)hexan-3-ol;
1-(1,4-benzodioxan-2-yl)-2-nitro-6-cyano-6-(ethyl)-6-(3,4-dimethoxy-2,5-dipentoxyphenyl)hexan-3-ol;
1-(1,4-benzodioxan-2-yl)-2-nitro-6-cyano-6-(prop-2-yl)-6-(3,4-dimethoxy-2,5-dipentoxyphenyl)hexan-3-ol;
1-(1,4-benzodioxan-2-yl)-2-nitro-6-cyano-6-(but-2-yl)-6-(3,4-dimethoxy-2,5-dipentoxyphenyl)hexan-3-ol; and
1-(1,4-benzodioxan-2-yl)-2-nitro-6-cyano-6-(pent-3-yl)-6-(3,4-dimethoxy-2,5-dipentoxyphenyl)hexan-3-ol.

PREPARATION 7

(Intermediates of Formula 9)

(A) A mixture of 1-(3,4-dimethoxyphenyl)-2-nitro-6-cyano-6-(i-propyl)-6-(3,4-dimethoxyphenyl)hexan-3-ol (8, 75 g, 0.154 mol), 4-dimethylaminopyridine ("DMAP," 1.5 g, Aldrich), and acetic anhydride (23 mL) in $CH_2Cl_2$ (700 mL) was heated at reflux for 40 minutes to yield 1-(3,4-dimethoxyphenyl)-2-nitro-3-acetoxy-6-cyano-6-(i-propyl)-6-(3,4-dimethoxyphenyl)-hexane (9), which was used in the next step without isolation.

(B) Similarly, proceeding as in part (A) above but substituting the compounds prepared in Preparation 6(B-C) for 1-(3,4-dimethoxyphenyl)-2-nitro-6-cyano-6-(i-propyl)-6-(3,4-dimethoxyphenyl)hexan-3-ol, the following compounds are prepared:

1-(3,4-dimethoxyphenyl)-2-nitro-3-acetoxy-6-cyano-6-(methyl)-6-(3,4-dimethoxyphenyl)hexane;
1-(3,4-dimethoxyphenyl)-2-nitro-3-acetoxy-6-cyano-6-(ethyl)-6-(3,4-dimethoxyphenyl)hexane;
1-(3,4-dimethoxyphenyl)-2-nitro-3-acetoxy-6-cyano-6-(but-2-yl)-6-(3,4-dimethoxyphenyl)hexane;
1-(3,4-dimethoxyphenyl)-2-nitro-3-acetoxy-6-cyano-6-(pent-3-yl)-6-(3,4-dimethoxyphenyl)hexane;
1-(1,3-benzodioxol-2-yl)-2-nitro-3-acetoxy-6-cyano-6-(methyl)-6-(3,4-dimethoxyphenyl)hexane;
1-(1,3-benzodioxol-2-yl)-2-nitro-3-acetoxy-6-cyano-6-(ethyl)-6-(3,4-dimethoxyphenyl)hexane;
1-(1,3-benzodioxol-2-yl)-2-nitro-3-acetoxy-6-cyano-6-(prop-2-yl)-6-(3,4-dimethoxyphenyl)hexane;
1-(1,3-benzodioxol-2-yl)-2-nitro-3-acetoxy-6-cyano-6-(but-2-yl)-6-(3,4-dimethoxyphenyl)hexane;
1-(1,3-benzodioxol-2-yl)-2-nitro-3-acetoxy-6-cyano-6-(pent-3-yl)-6-(3,4-dimethoxyphenyl)hexane;
1-(1,4-benzodioxan-2-yl)-2-nitro-3-acetoxy-6-cyano-6-(methyl)-6-(3,4-dimethoxyphenyl)hexane;
1-(1,4-benzodioxan-2-yl)-2-nitro-3-acetoxy-6-cyano-6-(ethyl)-6-(3,4-dimethoxyphenyl)hexane;
1-(1,4-benzodioxan-2-yl)-2-nitro-3-acetoxy-6-cyano-6-(prop-2-yl)-6-(3,4-dimethoxyphenyl)hexane;
1-(1,4-benzodioxan-2-yl)-2-nitro-3-acetoxy-6-cyano-6-(but-2-yl)-6-(3,4-dimethoxyphenyl)hexane;
1-(1,4-benzodioxan-2-yl)-2-nitro-3-acetoxy-6-cyano-6-(pent-3-yl)-6-(3,4-dimethoxyphenyl)hexane;
1-(3,4-dimethoxyphenyl)-2-nitro-3-acetoxy-6-cyano-6-(methyl)-6-(3,4,5-trimethoxyphenyl)hexane;
1-(3,4-dimethoxyphenyl)-2-nitro-3-acetoxy-6-cyano-6-(ethyl)-6-(3,4,5-trimethoxyphenyl)hexane;
1-(3,4-dimethoxyphenyl)-2-nitro-3-acetoxy-6-cyano-6-(prop-2-yl)-6-(3,4,5-trimethoxyphenyl)hexane;
1-(3,4-dimethoxyphenyl)-2-nitro-3-acetoxy-6-cyano-6-(but-2-yl)-6-(3,4,5-trimethoxyphenyl)hexane;
1-(3,4-dimethoxyphenyl)-2-nitro-3-acetoxy-6-cyano-6-(pent-3-yl)-6-(3,4,5-trimethoxyphenyl)hexane;
1-(1,3-benzodioxol-2-yl)-2-nitro-3-acetoxy-6-cyano-6-(methyl)-6-(3,4,5-trimethoxyphenyl)hexane;
1-(1,3-benzodioxol-2-yl)-2-nitro-3-acetoxy-6-cyano-6-(ethyl)-6-(3,4,5-trimethoxyphenyl)hexane;
1-(1,3-benzodioxol-2-yl)-2-nitro-3-acetoxy-6-cyano-6-(prop-2-yl)-6-(3,4,5-trimethoxyphenyl)hexane;
1-(1,3-benzodioxol-2-yl)-2-nitro-3-acetoxy-6-cyano-6-(but-2-yl)-6-(3,4,5-trimethoxyphenyl)hexane;
1-(1,3-benzodioxol-2-yl)-2-nitro-3-acetoxy-6-cyano-6-(pent-3-yl)-6-(3,4,5-trimethoxyphenyl)hexane;
1-(1,4-benzodioxan-2-yl)-2-nitro-3-acetoxy-6-cyano-6-(methyl)-6-(3,4,5-trimethoxyphenyl)hexane;
1-(1,4-benzodioxan-2-yl)-2-nitro-3-acetoxy-6-cyano-6-(ethyl)-6-(3,4,5-trimethoxyphenyl)hexane;
1-(1,4-benzodioxan-2-yl)-2-nitro-3-acetoxy-6-cyano-6-(prop-2-yl)-6-(3,4,5-trimethoxyphenyl)hexane;
1-(1,4-benzodioxan-2-yl)-2-nitro-3-acetoxy-6-cyano-6-(but-2-yl)-6-(3,4,5-trimethoxyphenyl)hexane;
1-(1,4-benzodioxan-2-yl)-2-nitro-3-acetoxy-6-cyano-6-(pent-3-yl)-6-(3,4,5-trimethoxyphenyl)hexane;
1-(3,4-dimethoxyphenyl)-2-nitro-3-acetoxy-6-cyano-6-(methyl)-6-(2,3,4-trimethoxyphenyl)hexane;
1-(3,4-dimethoxyphenyl)-2-nitro-3-acetoxy-6-cyano-6-(ethyl)-6-(2,3,4-trimethoxyphenyl)hexane;
1-(3,4-dimethoxyphenyl)-2-nitro-3-acetoxy-6-cyano-6-(prop-2-yl)-6-(2,3,4-trimethoxyphenyl)hexane;
1-(3,4-dimethoxyphenyl)-2-nitro-3-acetoxy-6-cyano-6-(but-2-yl)-6-(2,3,4-trimethoxyphenyl)hexane;
1-(3,4-dimethoxyphenyl)-2-nitro-3-acetoxy-6-cyano-6-(pent-3-yl)-6-(2,3,4-trimethoxyphenyl)hexane;
1-(1,3-benzodioxol-2-yl)-2-nitro-3-acetoxy-6-cyano-6-(methyl)-6-(2,3,4-trimethoxyphenyl)hexane;
1-(1,3-benzodioxol-2-yl)-2-nitro-3-acetoxy-6-cyano-6-(ethyl)-6-(2,3,4-trimethoxyphenyl)hexane;
1-(1,3-benzodioxol-2-yl)-2-nitro-3-acetoxy-6-cyano-6-(prop-2-yl)-6-(2,3,4-trimethoxyphenyl)hexane;
1-(1,3-benzodioxol-2-yl)-2-nitro-3-acetoxy-6-cyano-6-(but-2-yl)-6-(2,3,4-trimethoxyphenyl)hexane;
1-(1,3-benzodioxol-2-yl)-2-nitro-3-acetoxy-6-cyano-6-(pent-3-yl)-6-(2,3,4-trimethoxyphenyl)hexane;
1-(1,4-benzodioxan-2-yl)-2-nitro-3-acetoxy-6-cyano-6-(methyl)-6-(2,3,4-trimethoxyphenyl)hexane;
1-(1,4-benzodioxan-2-yl)-2-nitro-3-acetoxy-6-cyano-6-(ethyl)-6-(2,3,4-trimethoxyphenyl)hexane;
1-(1,4-benzodioxan-2-yl)-2-nitro-3-acetoxy-6-cyano-6-(prop-2-yl)-6-(2,3,4-trimethoxyphenyl)hexane;
1-(1,4-benzodioxan-2-yl)-2-nitro-3-acetoxy-6-cyano-6-(but-2-yl)-6-(2,3,4-trimethoxyphenyl)hexane;
1-(1,4-benzodioxan-2-yl)-2-nitro-3-acetoxy-6-cyano-6-(pent-3-yl)-6-(2,3,4-trimethoxyphenyl)hexane;
1-(3,4-dimethoxyphenyl)-2-nitro-3-acetoxy-6-cyano-6-(methyl)-6-(2,3,4,5-tetramethoxyphenyl)hexane;
1-(3,4-dimethoxyphenyl)-2-nitro-3-acetoxy-6-cyano-6-(ethyl)-6-(2,3,4,5-tetramethoxyphenyl)hexane;
1-(3,4-dimethoxyphenyl)-2-nitro-3-acetoxy-6-cyano-6-(prop-2-yl)-6-(2,3,4,5-tetramethoxyphenyl)hexane;
1-(3,4-dimethoxyphenyl)-2-nitro-3-acetoxy-6-cyano-6-(but-2-yl)-6-(2,3,4,5-tetramethoxyphenyl)hexane;
1-(3,4-dimethoxyphenyl)-2-nitro-3-acetoxy-6-cyano-6-(pent-3-yl)-6-(2,3,4,5-tetramethoxyphenyl)hexane;
1-(1,3-benzodioxol-2-yl)-2-nitro-3-acetoxy-6-cyano-6-(methyl)-6-(2,3,4,5-tetramethoxyphenyl)hexane;
1-(1,3-benzodioxol-2-yl)-2-nitro-3-acetoxy-6-cyano-6-(ethyl)-6-(2,3,4,5-tetramethoxyphenyl)hexane;
1-(1,3-benzodioxol-2-yl)-2-nitro-3-acetoxy-6-cyano-6-(prop-2-yl)-6-(2,3,4,5-tetramethoxyphenyl)hexane;
1-(1,3-benzodioxol-2-yl)-2-nitro-3-acetoxy-6-cyano-6-(but-2-yl)-6-(2,3,4,5-tetramethoxyphenyl)hexane;
1-(1,3-benzodioxol-2-yl)-2-nitro-3-acetoxy-6-cyano-6-(pent-3-yl)-6-(2,3,4,5-tetramethoxyphenyl)hexane;
1-(1,4-benzodioxan-2-yl)-2-nitro-3-acetoxy-6-cyano-6-(methyl)-6-(2,3,4,5-tetramethoxyphenyl)hexane;
1-(1,4-benzodioxan-2-yl)-2-nitro-3-acetoxy-6-cyano-6-(ethyl)-6-(2,3,4,5-tetramethoxyphenyl)hexane;
1-(1,4-benzodioxan-2-yl)-2-nitro-3-acetoxy-6-cyano-6-(prop-2-yl)-6-(2,3,4,5-tetramethoxyphenyl)hexane;
1-(1,4-benzodioxan-2-yl)-2-nitro-3-acetoxy-6-cyano-6-(but-2-yl)-6-(2,3,4,5-tetramethoxyphenyl)hexane;
1-(1,4-benzodioxan-2-yl)-2-nitro-3-acetoxy-6-cyano-6-(pent-3-yl)-6-(2,3,4,5-tetramethoxyphenyl)hexane;

1-(3,4-dimethoxyphenyl)-2-nitro-3-acetoxy-6-cyano-6-(methyl)-6-(3,4-dimethoxy-2,5-diethoxyphenyl)hexane;

1-(3,4-dimethoxyphenyl)-2-nitro-3-acetoxy-6-cyano-6-(ethyl)-6-(3,4-dimethoxy-2,5-diethoxyphenyl)hexane;

1-(3,4-dimethoxyphenyl)-2-nitro-3-acetoxy-6-cyano-6-(but-2-yl)-6-(3,4-dimethoxy-2,5-diethoxyphenyl)hexane;

1-(3,4-dimethoxyphenyl)-2-nitro-3-acetoxy-6-cyano-6-(pent-3-yl)-6-(3,4-dimethoxy-2,5-diethoxyphenyl)hexane;

1-(1,3-benzodioxol-2-yl)-2-nitro-3-acetoxy-6-cyano-6-(methyl)-6-(3,4-dimethoxy-2,5-diethoxyphenyl)hexane;

1-(1,3-benzodioxol-2-yl)-2-nitro-3-acetoxy-6-cyano-6-(ethyl)-6-(3,4-dimethoxy-2,5-diethoxyphenyl)hexane;

1-(1,3-benzodioxol-2-yl)-2-nitro-3-acetoxy-6-cyano-6-(prop-2-yl)-6-(3,4-dimethoxy-2,5-diethoxyphenyl)hexane;

1-(1,3-benzodioxol-2-yl)-2-nitro-3-acetoxy-6-cyano-6-(but-2-yl)-6-(3,4-dimethoxy-2,5-diethoxyphenyl)hexane;

1-(1,3-benzodioxol-2-yl)-2-nitro-3-acetoxy-6-cyano-6-(pent-3-yl)-6-(3,4-dimethoxy-2,5-diethoxyphenyl)hexane;

1-(1,4-benzodioxan-2-yl)-2-nitro-3-acetoxy-6-cyano-6-(methyl)-6-(3,4-dimethoxy-2,5-diethoxyphenyl)hexane;

1-(1,4-benzodioxan-2-yl)-2-nitro-3-acetoxy-6-cyano-6-(ethyl)-6-(3,4-dimethoxy-2,5-diethoxyphenyl)hexane;

1-(1,4-benzodioxan-2-yl)-2-nitro-3-acetoxy-6-cyano-6-(prop-2-yl)-6-(3,4-dimethoxy-2,5-diethoxyphenyl)hexane;

1-(1,4-benzodioxan-2-yl)-2-nitro-3-acetoxy-6-cyano-6-(but-2-yl)-6-(3,4-dimethoxy-2,5-diethoxyphenyl)hexane;

1-(1,4-benzodioxan-2-yl)-2-nitro-3-acetoxy-6-cyano-6-(pent-3-yl)-6-(3,4-dimethoxy-2,5-diethoxyphenyl)hexane;

1-(3,4-dimethoxyphenyl)-2-nitro-3-acetoxy-6-cyano-6-(methyl)-6-(3,4-dimethoxy-2,5-dipentoxyphenyl)hexane;

1-(3,4-dimethoxyphenyl)-2-nitro-3-acetoxy-6-cyano-6-(ethyl)-6-(3,4-dimethoxy-2,5-dipentoxyphenyl)hexane;

1-(3,4-dimethoxyphenyl)-2-nitro-3-acetoxy-6-cyano-6-(prop-2-yl)-6-(3,4-dimethoxy-2,5-dipentoxyphenyl)hexane;

1-(3,4-dimethoxyphenyl)-2-nitro-3-acetoxy-6-cyano-6-(but-2-yl)-6-(3,4-dimethoxy-2,5-dipentoxyphenyl)hexane;

1-(3,4-dimethoxyphenyl)-2-nitro-3-acetoxy-6-cyano-6-(pent-3-yl)-6-(3,4-dimethoxy-2,5-dipentoxyphenyl)hexane;

1-(1,3-benzodioxol-2-yl)-2-nitro-3-acetoxy-6-cyano-6-(methyl)-6-(3,4-dimethoxy-2,5-dipentoxyphenyl)hexane;

1-(1,3-benzodioxol-2-yl)-2-nitro-3-acetoxy-6-cyano-6-(ethyl)-6-(3,4-dimethoxy-2,5-dipentoxyphenyl)hexane;

1-(1,3-benzodioxol-2-yl)-2-nitro-3-acetoxy-6-cyano-6-(prop-2-yl)-6-(3,4-dimethoxy-2,5-dipentoxyphenyl)hexane;

1-(1,3-benzodioxol-2-yl)-2-nitro-3-acetoxy-6-cyano-6-(but-2-yl)-6-(3,4-dimethoxy-2,5-dipentoxyphenyl)hexane;

1-(1,3-benzodioxol-2-yl)-2-nitro-3-acetoxy-6-cyano-6-(pent-3-yl)-6-(3,4-dimethoxy-2,5-dipentoxyphenyl)hexane;

1-(1,4-benzodioxan-2-yl)-2-nitro-3-acetoxy-6-cyano-6-(methyl)-6-(3,4-dimethoxy-2,5-dipentoxyphenyl)hexane;

1-(1,4-benzodioxan-2-yl)-2-nitro-3-acetoxy-6-cyano-6-(ethyl)-6-(3,4-dimethoxy-2,5-dipentoxyphenyl)hexane;

1-(1,4-benzodioxan-2-yl)-2-nitro-3-acetoxy-6-cyano-6-(prop-2-yl)-6-(3,4-dimethoxy-2,5-dipentoxyphenyl)hexane;

1-(1,4-benzodioxan-2-yl)-2-nitro-3-acetoxy-6-cyano-6-(but-2-yl)-6-(3,4-dimethoxy-2,5-dipentoxyphenyl)hexane; and 1-(1,4-benzodioxan-2-yl)-2-nitro-3-acetoxy-6-cyano-6-(pent-3-yl)-6-(3,4-dimethoxy-2,5-dipentoxyphenyl)hexane.

PREPARATION 8

(Intermediates of Formula 10)

(A) The reaction mixture containing 1-(3,4-dimethoxyphenyl)-2-nitro-3-acetoxy-6-cyano-6-(i-propyl)-6-(3,4-dimethoxyphenyl)hexane (9) prepared in Preparation 7(A) was cooled to room temperature and diluted with isopropanol (350 mL). Solid NaBH$_4$ (15 g, 0.4 mol) was added over 15 minutes at 25° C. The mixture was then heated to reflux (about 40° C.) for 15 hours, then cooled to 5° C. A solution of 10% HCl (30 mL) was slowly added, followed by water (100 mL). The organic layer was extracted, washed with saturated aqueous NH$_4$Cl (200 mL), and saturated aqueous NaHCO$_3$ (200 mL). The organic layer was evaporated to yield 1-(3,4-dimethoxyphenyl)-2-nitro-6-cyano-6-(i-propyl)-6-(3,4-dimethoxyphenyl)hexane (10, 58.7 g, m.p. 107°–110° C., MS m/e 470(M+)) as a pale yellow solid.

(B) Similarly, proceeding as in part (A) above but substituting the compounds prepared in Preparation 7(B) for 1-(3,4-dimethoxyphenyl)-2-nitro-3-acetoxy-6-cyano-6-(i-propyl)-6-(3,4-dimethoxyphenyl)hexane, the following compounds are prepared:

1-(3,4-dimethoxyphenyl)-2-nitro-6-cyano-6-(methyl)-6-(3,4-dimethoxyphenyl)hexane;

1-(3,4-dimethoxyphenyl)-2-nitro-6-cyano-6-(ethyl)-6-(3,4-dimethoxyphenyl)hexane;

1-(3,4-dimethoxyphenyl)-2-nitro-6-cyano-6-(but-2-yl)-6-(3,4-dimethoxyphenyl)hexane;

1-(3,4-dimethoxyphenyl)-2-nitro-6-cyano-6-(pent-3-yl)-6-(3,4-dimethoxyphenyl)hexane;

1-(1,3-benzodioxol-2-yl)-2-nitro-6-cyano-6-(methyl)-6-(3,4-dimethoxyphenyl)hexane;

1-(1,3-benzodioxol-2-yl)-2-nitro-6-cyano-6-(ethyl)-6-(3,4-dimethoxyphenyl)hexane;

1-(1,3-benzodioxol-2-yl)-2-nitro-6-cyano-6-(prop-2-yl)-6-(3,4-dimethoxyphenyl)hexane;

1-(1,3-benzodioxol-2-yl)-2-nitro-6-cyano-6-(but-2-yl)-6-(3,4-dimethoxyphenyl)hexane;

1-(1,3-benzodioxol-2-yl)-2-nitro-6-cyano-6-(pent-3-yl)-6-(3,4-dimethoxyphenyl)hexane;

1-(1,4-benzodioxan-2-yl)-2-nitro-6-cyano-6-(methyl)-6-(3,4-dimethoxyphenyl)hexane;

1-(1,4-benzodioxan-2-yl)-2-nitro-6-cyano-6-(ethyl)-6-(3,4-dimethoxyphenyl)hexane;

1-(1,4-benzodioxan-2-yl)-2-nitro-6-cyano-6-(prop-2-yl)-6-(3,4-dimethoxyphenyl)hexane;

1-(1,4-benzodioxan-2-yl)-2-nitro-6-cyano-6-(but-2-yl)-6-(3,4-dimethoxyphenyl)hexane;

1-(1,4-benzodioxan-2-yl)-2-nitro-6-cyano-6-(pent-3-yl)-6-(3,4-dimethoxyphenyl)hexane;
1-(3,4-dimethoxyphenyl)-2-nitro-6-cyano-6-(methyl)-6-(3,4,5-trimethoxyphenyl)hexane;
1-(3,4-dimethoxyphenyl)-2-nitro-6-cyano-6-(ethyl)-6-(3,4,5-trimethoxyphenyl)hexane;
1-(3,4-dimethoxyphenyl)-2-nitro-6-cyano-6-(prop-2-yl)-6-(3,4,5-trimethoxyphenyl)hexane;
1-(3,4-dimethoxyphenyl)-2-nitro-6-cyano-6-(but-2-yl)-6-(3,4,5-trimethoxyphenyl)hexane;
1-(3,4-dimethoxyphenyl)-2-nitro-6-cyano-6-(pent-3-yl)-6-(3,4,5-trimethoxyphenyl)hexane;
1-(1,3-benzodioxol-2-yl)-2-nitro-6-cyano-6-(methyl)-6-(3,4,5-trimethoxyphenyl)hexane;
1-(1,3-benzodioxol-2-yl)-2-nitro-6-cyano-6-(ethyl)-6-(3,4,5-trimethoxyphenyl)hexane;
1-(1,3-benzodioxol-2-yl)-2-nitro-6-cyano-6-(prop-2-yl)-6-(3,4,5-trimethoxyphenyl)hexane;
1-(1,3-benzodioxol-2-yl)-2-nitro-6-cyano-6-(but-2-yl)-6-(3,4,5-trimethoxyphenyl)hexane;
1-(1,3-benzodioxol-2-yl)-2-nitro-6-cyano-6-(pent-3-yl)-6-(3,4,5-trimethoxyphenyl)hexane;
1-(1,4-benzodioxan-2-yl)-2-nitro-6-cyano-6-(methyl)-6-(3,4,5-trimethoxyphenyl)hexane;
1-(1,4-benzodioxan-2-yl)-2-nitro-6-cyano-6-(ethyl)-6-(3,4,5-trimethoxyphenyl)hexane;
1-(1,4-benzodioxan-2-yl)-2-nitro-6-cyano-6-(prop-2-yl)-6-(3,4,5-trimethoxyphenyl)hexane;
1-(1,4-benzodioxan-2-yl)-2-nitro-6-cyano-6-(but-2-yl)-6-(3,4,5-trimethoxyphenyl)hexane;
1-(1,4-benzodioxan-2-yl)-2-nitro-6-cyano-6-(pent-3-yl)-6-(3,4,5-trimethoxyphenyl)hexane;
1-(3,4-dimethoxyphenyl)-2-nitro-6-cyano-6-(methyl)-6-(2,3,4-trimethoxyphenyl)hexane;
1-(3,4-dimethoxyphenyl)-2-nitro-6-cyano-6-(ethyl)-6-(2,3,4-trimethoxyphenyl)hexane;
1-(3,4-dimethoxyphenyl)-2-nitro-6-cyano-6-(prop-2-yl)-6-(2,3,4-trimethoxyphenyl)hexane;
1-(3,4-dimethoxyphenyl)-2-nitro-6-cyano-6-(but-2-yl)-6-(2,3,4-trimethoxyphenyl)hexane;
1-(3,4-dimethoxyphenyl)-2-nitro-6-cyano-6-(pent-3-yl)-6-(2,3,4-trimethoxyphenyl)hexane;
1-(1,3-benzodioxol-2-yl)-2-nitro-6-cyano-6-(methyl)-6-(2,3,4-trimethoxyphenyl)hexane;
1-(1,3-benzodioxol-2-yl)-2-nitro-6-cyano-6-(ethyl)-6-(2,3,4-trimethoxyphenyl)hexane;
1-(1,3-benzodioxol-2-yl)-2-nitro-6-cyano-6-(prop-2-yl)-6-(2,3,4-trimethoxyphenyl)hexane;
1-(1,3-benzodioxol-2-yl)-2-nitro-6-cyano-6-(but-2-yl)-6-(2,3,4-trimethoxyphenyl)hexane;
1-(1,3-benzodioxol-2-yl)-2-nitro-6-cyano-6-(pent-3-yl)-6-(2,3,4-trimethoxyphenyl)hexane;
1-(1,4-benzodioxan-2-yl)-2-nitro-6-cyano-6-(methyl)-6-(2,3,4-trimethoxyphenyl)hexane;
1-(1,4-benzodioxan-2-yl)-2-nitro-6-cyano-6-(ethyl)-6-(2,3,4-trimethoxyphenyl)hexane;
1-(1,4-benzodioxan-2-yl)-2-nitro-6-cyano-6-(prop-2-yl)-6-(2,3,4-trimethoxyphenyl)hexane;
1-(1,4-benzodioxan-2-yl)-2-nitro-6-cyano-6-(but-2-yl)-6-(2,3,4-trimethoxyphenyl)hexane;
1-(1,4-benzodioxan-2-yl)-2-nitro-6-cyano-6-(pent-3-yl)-6-(2,3,4-trimethoxyphenyl)hexane;
1-(3,4-dimethoxyphenyl)-2-nitro-6-cyano-6-(methyl)-6-(2,3,4,5-tetramethoxyphenyl)hexane;
1-(3,4-dimethoxyphenyl)-2-nitro-6-cyano-6-(ethyl)-6-(2,3,4,5-tetramethoxyphenyl)hexane;
1-(3,4-dimethoxyphenyl)-2-nitro-6-cyano-6-(prop-2-yl)-6-(2,3,4,5-tetramethoxyphenyl)hexane;
1-(3,4-dimethoxyphenyl)-2-nitro-6-cyano-6-(but-2-yl)-6-(2,3,4,5-tetramethoxyphenyl)hexane;
1-(3,4-dimethoxyphenyl)-2-nitro-6-cyano-6-(pent-3-yl)-6-(2,3,4,5-tetramethoxyphenyl)hexane;
1-(1,3-benzodioxol-2-yl)-2-nitro-6-cyano-6-(methyl)-6-(2,3,4,5-tetramethoxyphenyl)hexane;
1-(1,3-benzodioxol-2-yl)-2-nitro-6-cyano-6-(ethyl)-6-(2,3,4,5-tetramethoxyphenyl)hexane;
1-(1,3-benzodioxol-2-yl)-2-nitro-6-cyano-6-(prop-2-yl)-6-(2,3,4,5-tetramethoxyphenyl)hexane;
1-(1,3-benzodioxol-2-yl)-2-nitro-6-cyano-6-(but-2-yl)-6-(2,3,4,5-tetramethoxyphenyl)hexane;
1-(1,3-benzodioxol-2-yl)-2-nitro-6-cyano-6-(pent-3-yl)-6-(2,3,4,5-tetramethoxyphenyl)hexane;
1-(1,4-benzodioxan-2-yl)-2-nitro-6-cyano-6-(methyl)-6-(2,3,4,5-tetramethoxyphenyl)hexane;
1-(1,4-benzodioxan-2-yl)-2-nitro-6-cyano-6-(ethyl)-6-(2,3,4,5-tetramethoxyphenyl)hexane;
1-(1,4-benzodioxan-2-yl)-2-nitro-6-cyano-6-(prop-2-yl)-6-(2,3,4,5-tetramethoxyphenyl)hexane;
1-(1,4-benzodioxan-2-yl)-2-nitro-6-cyano-6-(but-2-yl)-6-(2,3,4,5-tetramethoxyphenyl)hexane;
1-(1,4-benzodioxan-2-yl)-2-nitro-6-cyano-6-(pent-3-yl)-6-(2,3,4,5-tetramethoxyphenyl)hexane;
1-(3,4-dimethoxyphenyl)-2-nitro-6-cyano-6-(methyl)-6-(3,4-dimethoxy-2,5-diethoxyphenyl)hexane;
1-(3,4-dimethoxyphenyl)-2-nitro-6-cyano-6-(ethyl)-6-(3,4-dimethoxy-2,5-diethoxyphenyl)hexane;
1-(3,4-dimethoxyphenyl)-2-nitro-6-cyano-6-(but-2-yl)-6-(3,4-dimethoxy-2,5-diethoxyphenyl)hexane;
1-(3,4-dimethoxyphenyl)-2-nitro-6-cyano-6-(pent-3-yl)-6-(3,4-dimethoxy-2,5-diethoxyphenyl)hexane;
1-(1,3-benzodioxol-2-yl)-2-nitro-6-cyano-6-(methyl)-6-(3,4-dimethoxy-2,5-diethoxyphenyl)hexane;
1-(1,3-benzodioxol-2-yl)-2-nitro-6-cyano-6-(ethyl)-6-(3,4-dimethoxy-2,5-diethoxyphenyl)hexane;
1-(1,3-benzodioxol-2-yl)-2-nitro-6-cyano-6-(prop-2-yl)-6-(3,4-dimethoxy-2,5-diethoxyphenyl)hexane;
1-(1,3-benzodioxol-2-yl)-2-nitro-6-cyano-6-(but-2-yl)-6-(3,4-dimethoxy-2,5-diethoxyphenyl)hexane;
1-(1,3-benzodioxol-2-yl)-2-nitro-6-cyano-6-(pent-3-yl)-6-(3,4-dimethoxy-2,5-diethoxyphenyl)hexane;
1-(1,4-benzodioxan-2-yl)-2-nitro-6-cyano-6-(methyl)-6-(3,4-dimethoxy-2,5-diethoxyphenyl)hexane;
1-(1,4-benzodioxan-2-yl)-2-nitro-6-cyano-6-(ethyl)-6-(3,4-dimethoxy-2,5-diethoxyphenyl)hexane;
1-(1,4-benzodioxan-2-yl)-2-nitro-6-cyano-6-(prop-2-yl)-6-(3,4-dimethoxy-2,5-diethoxyphenyl)hexane;
1-(1,4-benzodioxan-B 2-yl)-2-nitro-6-cyano-6-(but-2-yl)-6-(3,4-dimethoxy-2,5-diethoxyphenyl)hexane;
1-(1,4-benzodioxan-2-yl)-2-nitro-6-cyano-6-(pent-3-yl)-6-(3,4-dimethoxy-2,5-diethoxyphenyl)hexane;
1-(3,4-dimethoxyphenyl)-2-nitro-6-cyano-6-(methyl)-6-(3,4-dimethoxy-2,5-dipentoxyphenyl)hexane;
1-(3,4-dimethoxyphenyl)-2-nitro-6-cyano-6-(ethyl)-6-(3,4-dimethoxy-2,5-dipentoxyphenyl)hexane;
1-(3,4-dimethoxyphenyl)-2-nitro-6-cyano-6-(prop-2-yl)-6-(3,4-dimethoxy-2,5-dipentoxyphenyl)hexane;
1-(3,4-dimethoxyphenyl)-2-nitro-6-cyano-6-(but-2-yl)-6-(3,4-dimethoxy-2,5-dipentoxyphenyl)hexane;
1-(3,4-dimethoxyphenyl)-2-nitro-6-cyano-6-(pent-3-yl)-6-(3,4-dimethoxy-2,5-dipentoxyphenyl)hexane;
1-(1,3-benzodioxol-2-yl)-2-nitro-6-cyano-6-(methyl)-6-(3,4-dimethoxy-2,5-dipentoxyphenyl)hexane;
1-(1,3-benzodioxol-2-yl)-2-nitro-6-cyano-6-(ethyl)-6-(3,4-dimethoxy-2,5-dipentoxyphenyl)hexane;
1-(1,3-benzodioxol-2-yl)-2-nitro-6-cyano-6-(prop-2-yl)-6-(3,4-dimethoxy-2,5-dipentoxyphenyl)hexane;

1-(1,3-benzodioxol-2-yl)-2-nitro-6-cyano-6-(but-2-yl)-6-(3,4-dimethoxy-2,5-dipentoxyphenyl)hexane;
1-(1,3-benzodioxol-2-yl)-2-nitro-6-cyano-6-(pent-3-yl)-6-(3,4-dimethoxy-2,5-dipentoxyphenyl)hexane;
1-(1,4-benzodioxan-2-yl)-2-nitro-6-cyano-6-(methyl)-6-(3,4-dimethoxy-2,5-dipentoxyphenyl)hexane;
1-(1,4-benzodioxan-2-yl)-2-nitro-6-cyano-6-(ethyl)-6-(3,4-dimethoxy-2,5-dipentoxyphenyl)hexane;
1-(1,4-benzodioxan-2-yl)-2-nitro-6-cyano-6-(prop-2-yl)-6-(3,4-dimethoxy-2,5-dipentoxyphenyl)hexane;
1-(1,4-benzodioxan-2-yl)-2-nitro-6-cyano-6-(but-2-yl)-6-(3,4-dimethoxy-2,5-dipentoxyphenyl)hexane; and
1-(1,4-benzodioxan-2-yl)-2-nitro-6-cyano-6-(pent-3-yl)-6-(3,4-dimethoxy-2,5-dipentoxyphenyl)hexane.

PREPARATION 9

(Intermediates of Formula 11)

(A) A mixture of 1-(3,4-dimethoxyphenyl)-2-nitro-6-cyano-6-(i-propyl)-6-(3,4-dimethoxyphenyl)hexane (10, 58.7 g, 0.125 mol) and methanol (950 mL) was added to a flask, and evacuated to remove oxygen. The catalyst, 5% Pd in carbon (50% water, 19 g, Engelhard Co.), was added under an $N_2$ atmosphere. After stirring for 10 minutes at room temperature, solid $HCO_2NH_4$ (65 g, Aldrich) was added, and the resulting mixture stirred for 1 hour. The mixture was then slowly heated to 50° C. for 48 hours, then cooled to room temperature and filtered through Celite (50 g). The solids were washed with methanol (50 mL), the filtrates concentrated in vacuo, and the resulting solid dissolved in $CH_2Cl_2$. The solution was extracted with saturated aqueous $NH_4Cl$ (500 mL) and saturated aqueous $NaHCO_3$ (300 mL), and the organic layer evaporated to yield 1-(3,4-dimethoxyphenyl)-2-amino-6-cyano-6-(i-propyl)-6-(3,4-dimethoxyphenyl)hexane (11, 52.3 g, MS m/e 440(M+)) as a pale yellow oil.

(B) Similarly, proceeding as in part (A) above but substituting the compounds prepared in Preparation 8(B) for 1-(3,4-dimethoxyphenyl)-2-nitro-6-cyano-6-(i-propyl)-6-(3,4-dimethoxyphenyl)hexane, the following compounds are prepared:

1-(3,4-dimethoxyphenyl)-2-amino-6-cyano-6-(methyl)-6-(3,4-dimethoxyphenyl)hexane;
1-(3,4-dimethoxyphenyl)-2-amino-6-cyano-6-(ethyl)-6-(3,4-dimethoxyphenyl)hexane;
1-(3,4-dimethoxyphenyl)-2-amino-6-cyano-6-(but-2-yl)-6-(3,4-dimethoxyphenyl)hexane;
1-(3,4-dimethoxyphenyl)-2-amino-6-cyano-6-(pent-3-yl)-6-(3,4-dimethoxyphenyl)hexane;
1-(1,3-benzodioxol-2-yl)-2-amino-6-cyano-6-(methyl)-6-(3,4-dimethoxyphenyl)hexane;
1-(1,3-benzodioxol-2-yl)-2-amino-6-cyano-6-(ethyl)-6-(3,4-dimethoxyphenyl)hexane;
1-(1,3-benzodioxol-2-yl)-2-amino-6-cyano-6-(prop-2-yl)-6-(3,4-dimethoxyphenyl)hexane;
1-(1,3-benzodioxol-2-yl)-2-amino-6-cyano-6-(but-2-yl)-6-(3,4-dimethoxyphenyl)hexane;
1-(1,3-benzodioxol-2-yl)-2-amino-6-cyano-6-(pent-3-yl)-6-(3,4-dimethoxyphenyl)hexane;
1-(1,4-benzodioxan-2-yl)-2-amino-6-cyano-6-(methyl)-6-(3,4-dimethoxyphenyl)hexane;
1-(1,4-benzodioxan-2-yl)-2-amino-6-cyano-6-(ethyl)-6-(3,4-dimethoxyphenyl)hexane;
1-(1,4-benzodioxan-2-yl)-2-amino-6-cyano-6-(prop-2-yl)-6-(3,4-dimethoxyphenyl)hexane;
1-(1,4-benzodioxan-2-yl)-2-amino-6-cyano-6-(but-2-yl)-6-(3,4-dimethoxyphenyl)hexane;
1-(1,4-benzodioxan-2-yl)-2-amino-6-cyano-6-(pent-3-yl)-6-(3,4-dimethoxyphenyl)hexane;
1-(3,4-dimethoxyphenyl)-2-amino-6-cyano-6-(methyl)-6-(3,4,5-trimethoxyphenyl)hexane;
1-(3,4-dimethoxyphenyl)-2-amino-6-cyano-6-(ethyl)-6-(3,4,5-trimethoxyphenyl)hexane;
1-(3,4-dimethoxyphenyl)-2-amino-6-cyano-6-(prop-2-yl)-6-(3,4,5-trimethoxyphenyl)hexane;
1-(3,4-dimethoxyphenyl)-2-amino-6-cyano-6-(but-2-yl)-6-(3,4,5-trimethoxyphenyl)hexane;
1-(3,4-dimethoxyphenyl)-2-amino-6-cyano-6-(pent-3-yl)-6-(3,4,5-trimethoxyphenyl)hexane;
1-(1,3-benzodioxol-2-yl)-2-amino-6-cyano-6-(methyl)-6-(3,4,5-trimethoxyphenyl)hexane;
1-(1,3-benzodioxol-2-yl)-2-amino-6-cyano-6-(ethyl)-6-(3,4,5-trimethoxyphenyl)hexane;
1-(1,3-benzodioxol-2-yl)-2-amino-6-cyano-6-(prop-2-yl)-6-(3,4,5-trimethoxyphenyl)hexane;
1-(1,3-benzodioxol-2-yl)-2-amino-6-cyano-6-(but-2-yl)-6-(3,4,5-trimethoxyphenyl)hexane;
1-(1,3-benzodioxol-2-yl)-2-amino-6-cyano-6-(pent-3-yl)-6-(3,4,5-trimethoxyphenyl)hexane;
1-(1,4-benzodioxan-2-yl)-2-amino-6-cyano-6-(methyl)-6-(3,4,5-trimethoxyphenyl)hexane;
1-(1,4-benzodioxan-2-yl)-2-amino-6-cyano-6-(ethyl)-6-(3,4,5-trimethoxyphenyl)hexane;
1-(1,4-benzodioxan-2-yl)-2-amino-6-cyano-6-(prop-2-yl)-6-(3,4,5-trimethoxyphenyl)hexane;
1-(1,4-benzodioxan-2-yl)-2-amino-6-cyano-6-(but-2-yl)-6-(3,4,5-trimethoxyphenyl)hexane;
1-(1,4-benzodioxan-2-yl)-2-amino-6-cyano-6-(pent-3-yl)-6-(3,4,5-trimethoxyphenyl)hexane;
1-(3,4-dimethoxyphenyl)-2-amino-6-cyano-6-(methyl)-6-(2,3,4-trimethoxyphenyl)hexane;
1-(3,4-dimethoxyphenyl)-2-amino-6-cyano-6-(ethyl)-6-(2,3,4-trimethoxyphenyl)hexane;
1-(3,4-dimethoxyphenyl)-2-amino-6-cyano-6-(prop-2-yl)-6-(2,3,4-trimethoxyphenyl)hexane;
1-(3,4-dimethoxyphenyl)-2-amino-6-cyano-6-(but-2-yl)-6-(2,3,4-trimethoxyphenyl)hexane;
1-(3,4-dimethoxyphenyl)-2-amino-6-cyano-6-(pent-3-yl)-6-(2,3,4-trimethoxyphenyl)hexane;
1-(1,3-benzodioxol-2-yl)-2-amino-6-cyano-6-(methyl)-6-(2,3,4-trimethoxyphenyl)hexane;
1-(1,3-benzodioxol-2-yl)-2-amino-6-cyano-6-(ethyl)-6-(2,3,4-trimethoxyphenyl)hexane;
1-(1,3-benzodioxol-2-yl)-2-amino-6-cyano-6-(prop-2-yl)-6-(2,3,4-trimethoxyphenyl)hexane;
1-(1,3-benzodioxol-2-yl)-2-amino-6-cyano-6-(but-2-yl)-6-(2,3,4-trimethoxyphenyl)hexane;
1-(1,3-benzodioxol-2-yl)-2-amino-6-cyano-6-(pent-3-yl)-6-(2,3,4-trimethoxyphenyl)hexane;
1-(1,4-benzodioxan-2-yl)-2-amino-6-cyano-6-(methyl)-6-(2,3,4-trimethoxyphenyl)hexane;
1-(1,4-benzodioxan-2-yl)-2-amino-6-cyano-6-(ethyl)-6-(2,3,4-trimethoxyphenyl)hexane;
1-(1,4-benzodioxan-2-yl)-2-amino-6-cyano-6-(prop-2-yl)-6-(2,3,4-trimethoxyphenyl)hexane;
1-(1,4-benzodioxan-2-yl)-2-amino-6-cyano-6-(but-2-yl)-6-(2,3,4-trimethoxyphenyl)hexane;
1-(1,4-benzodioxan-2-yl)-2-amino-6-cyano-6-(pent-3-yl)-6-(2,3,4-trimethoxyphenyl)hexane;
1-(3,4-dimethoxyphenyl)-2-amino-6-cyano-6-(methyl)-6-(2,3,4,5-tetramethoxyphenyl)hexane;
1-(3,4-dimethoxyphenyl)-2-amino-6-cyano-6-(ethyl)-6-(2,3,4,5-tetramethoxyphenyl)hexane;
1-(3,4-dimethoxyphenyl)-2-amino-6-cyano-6-(prop-2-yl)-6-(2,3,4,5-tetramethoxyphenyl)hexane;

1-(3,4-dimethoxyphenyl)-2-amino-6-cyano-6-(but-2-yl)-6-(2,3,4,5-tetramethoxyphenyl)hexane;
1-(3,4-dimethoxyphenyl)-2-amino-6-cyano-6-(pent-3-yl)-6-(2,3,4,5-tetramethoxyphenyl)hexane;
1-(1,3-benzodioxol-2-yl)-2-amino-6-cyano-6-(methyl)-6-(2,3,4,5-tetramethoxyphenyl)hexane;
1-(1,3-benzodioxol-2-yl)-2-amino-6-cyano-6-(ethyl)-6-(2,3,4,5-tetramethoxyphenyl)hexane;
1-(1,3-benzodioxol-2-yl)-2-amino-6-cyano-6-(prop-2-yl)-6-(2,3,4,5-tetramethoxyphenyl)hexane;
1-(1,3-benzodioxol-2-yl)-2-amino-6-cyano-6-(but-2-yl)-6-(2,3,4,5-tetramethoxyphenyl)hexane;
1-(1,3-benzodioxol-2-yl)-2-amino-6-cyano-6-(pent-3-yl)-6-(2,3,4,5-tetramethoxyphenyl)hexane;
1-(1,4-benzodioxan-2-yl)-2-amino-6-cyano-6-(methyl)-6-(2,3,4,5-tetramethoxyphenyl)hexane;
1-(1,4-benzodioxan-2-yl)-2-amino-6-cyano-6-(ethyl)-6-(2,3,4,5-tetramethoxyphenyl)hexane;
1-(1,4-benzodioxan-2-yl)-2-amino-6-cyano-6-(prop-2-yl)-6-(2,3,4,5-tetramethoxyphenyl)hexane;
1-(1,4-benzodioxan-2-yl)-2-amino-6-cyano-6-(but-2-yl)-6-(2,3,4,5-tetramethoxyphenyl)hexane;
1-(1,4-benzodioxan-2-yl)-2-amino-6-cyano-6-(pent-3-yl)-6-(2,3,4,5-tetramethoxyphenyl)hexane;
1-(3,4-dimethoxyphenyl)-2-amino-6-cyano-6-(methyl)-6-(3,4-dimethoxy-2,5-diethoxyphenyl)hexane;
1-(3,4-dimethoxyphenyl)-2-amino-6-cyano-6-(ethyl)-6-(3,4-dimethoxy-2,5-diethoxyphenyl)hexane;
1-(3,4-dimethoxyphenyl)-2-amino-6-cyano-6-(but-2-yl)-6-(3,4-dimethoxy-2,5-diethoxyphenyl)hexane;
1-(3,4-dimethoxyphenyl)-2-amino-6-cyano-6-(pent-3-yl)-6-(3,4-dimethoxy-2,5-diethoxyphenyl)hexane;
1-(1,3-benzodioxol-2-yl)-2-amino-6-cyano-6-(methyl)-6-(3,4-dimethoxy-2,5-diethoxyphenyl)hexane;
1-(1,3-benzodioxol-2-yl)-2-amino-6-cyano-6-(ethyl)-6-(3,4-dimethoxy-2,5-diethoxyphenyl)hexane;
1-(1,3-benzodioxol-2-yl)-2-amino-6-cyano-6-(prop-2-yl)-6-(3,4-dimethoxy-2,5-diethoxyphenyl)hexane;
1-(1,3-benzodioxol-2-yl)-2-amino-6-cyano-6-(but-2-yl)-6-(3,4-dimethoxy-2,5-diethoxyphenyl)hexane;
1-(1,3-benzodioxol-2-yl)-2-amino-6-cyano-6-(pent-3-yl)-6-(3,4-dimethoxy-2,5-diethoxyphenyl)hexane;
1-(1,4-benzodioxan-2-yl)-2-amino-6-cyano-6-(methyl)-6-(3,4-dimethoxy-2,5-diethoxyphenyl)hexane;
1-(1,4-benzodioxan-2-yl)-2-amino-6-cyano-6-(ethyl)-6-(3,4-dimethoxy-2,5-diethoxyphenyl)hexane;
1-(1,4-benzodioxan-2-yl)-2-amino-6-cyano-6-(prop-2-yl)-6-(3,4-dimethoxy-2,5-diethoxyphenyl)hexane;
1-(1,4-benzodioxan-2-yl)-2-amino-6-cyano-6-(but-2-yl)-6-(3,4-dimethoxy-2,5-diethoxyphenyl)hexane;
1-(1,4-benzodioxan-2-yl)-2-amino-6-cyano-6-(pent-3-yl)-6-(3,4-dimethoxy-2,5-diethoxyphenyl)hexane;
1-(3,4-dimethoxyphenyl)-2-amino-6-cyano-6-(methyl)-6-(3,4-dimethoxy-2,5-dipentoxyphenyl)hexane;
1-(3,4-dimethoxyphenyl)-2-amino-6-cyano-6-(ethyl)-6-(3,4-dimethoxy-2,5-dipentoxyphenyl)hexane;
1-(3,4-dimethoxyphenyl)-2-amino-6-cyano-6-(prop-2-yl)-6-(3,4-dimethoxy-2,5-dipentoxyphenyl)hexane;
1-(3,4-dimethoxyphenyl)-2-amino-6-cyano-6-(but-2-yl)-6-(3,4-dimethoxy-2,5-dipentoxyphenyl)hexane;
1-(3,4-dimethoxyphenyl)-2-amino-6-cyano-6-(pent-3-yl)-6-(3,4-dimethoxy-2,5-dipentoxyphenyl)hexane;
1-(1,3-benzodioxol-2-yl)-2-amino-6-cyano-6-(methyl)-6-(3,4-dimethoxy-2,5-dipentoxyphenyl)hexane;
1-(1,3-benzodioxol-2-yl)-2-amino-6-cyano-6-(ethyl)-6-(3,4-dimethoxy-2,5-dipentoxyphenyl)hexane;
1-(1,3-benzodioxol-2-yl)-2-amino-6-cyano-6-(prop-2-yl)-6-(3,4-dimethoxy-2,5-dipentoxyphenyl)hexane;
1-(1,3-benzodioxol-2-yl)-2-amino-6-cyano-6-(but-2-yl)-6-(3,4-dimethoxy-2,5-dipentoxyphenyl)hexane;
1-(1,3-benzodioxol-2-yl)-2-amino-6-cyano-6-(pent-3-yl)-6-(3,4-dimethoxy-2,5-dipentoxyphenyl)hexane;
1-(1,4-benzodioxan-2-yl)-2-amino-6-cyano-6-(methyl)-6-(3,4-dimethoxy-2,5-dipentoxyphenyl)hexane;
1-(1,4-benzodioxan-2-yl)-2-amino-6-cyano-6-(ethyl)-6-(3,4-dimethoxy-2,5-dipentoxyphenyl)hexane;
1-(1,4-benzodioxan-2-yl)-2-amino-6-cyano-6-(prop-2-yl)-6-(3,4-dimethoxy-2,5-dipentoxyphenyl)hexane;
1-(1,4-benzodioxan-2-yl)-2-amino-6-cyano-6-(but-2-yl)-6-(3,4-dimethoxy-2,5-dipentoxyphenyl)hexane; and
1-(1,4-benzodioxan-2-yl)-2-amino-6-cyano-6-(pent-3-yl)-6-(3,4-dimethoxy-2,5-dipentoxyphenyl)hexane.

PREPARATION 10

(Intermediates of Formula 13)

(A) L-3,4-dimethoxyphenylalaninol (12) was prepared by the method described by A. W. Schrecker and J. L. Hartwell, *J. Amer. Chem. Soc.*, 79, 3827 (1957). A solution of L-3,4-dimethoxyphenylalaninol (12, 23.3 g, 110 mmol) in THF (400 mL) was mixed with di-t-butyldicarbonate (24.0 g, 110 mmol) and the resulting solution heated at reflux for one hour. The mixture was then evaporated under reduced pressure and the residue filtered through silica gel using ethyl acetate. The filtrate was then evaporated to yield L-3-(3,4-dimethoxyphenyl)-2-(t-butoxycarbonylamino)propan-1-ol (13, 32.4 g, m.p. 92°–93° C., $[\alpha]_D^{25}=-19.6°$ (MeOH). Calculated for $C_{16}H_{25}NO_5$: C=61.72, H=8.09, N=4.50. Found: C=61.62, H=8.13, N=4.47.

(B) Similarly, proceeding as in part (A) above but substituting D-3,4-dimethoxyphenylalaninol, L-3,4,5-trimethoxyphenylalaninol, D-3,4,5-trimethoxyphenylalaninol, L-3,4-dimethoxy-2,5-diethoxyphenylalaninol, D-3,4-dimethoxy-2,5-diethoxyphenylalaninol, L-3,4-dimethoxy-2,5-dipentoxyphenylalaninol, or D-3,4-dimethoxy-2,5-dipentoxyphenylalinol, for L-3,4-dimethoxyphenylalaninol, the following compounds are prepared:
D-3-(3,4-dimethoxyphenyl)-2-(t-butoxycarbonylamino)-propan-1-ol;
L-3-(3,4,5-trimethoxyphenyl)-2-(t-butoxycarbonylamino)propan-1-ol;
D-3-(3,4,5-trimethoxyphenyl)-2-(t-butoxycarbonylamino)propan-1-ol;
L-3-(3,4-dimethoxy-2,5-diethoxyphenyl)-2-(t-butoxycarbonylamino)propan-1-ol;
D-3-(3,4-dimethoxy-2,5-diethoxyphenyl)-2-(t-butoxycarbonylamino)propan-1-ol;
L-3-(3,4-dimethoxy-2,5-dipentoxyphenyl)-2-(t-butoxycarbonylamino)propan-1-ol; and
D-3-(3,4-dimethoxy-2,5-dipentoxyphenyl)-2-(t-butoxycarbonylamino)propan-1-ol.

PREPARATION 11

(Intermediates of Formula 14)

(A) A solution of L-3-(3,4-dimethoxyphenyl)-2-(t-butoxycarbonylamino)propan-1-ol (13, 32.4 g, 104 mmol), p-toluenesulfonyl chloride (29.8 g, 156 mmol), and DMAP (0.63 g) in pyridine (100 mL) was stirred at room temperature for two days. The resulting mixture was then diluted with ether, washed with aqueous $CuSO_4$ and water, and the organic layer dried over $MgSO_4$ and evaporated. The residue was purified by medium pressure chromatography (30% ethyl acetate-hexane) to yield L-3-(3,4-dimethoxyphenyl)-2-(t-butoxycarbonylamino)-1-tosyloxypropane (14, m.p. 146°–148° C., $[\alpha]_D^{25} = -15.4°$ (CHCl$_3$)). Calculated for C$_{23}$H$_{31}$NO$_7$S: C=59.34, H=6.71, N=3.01. Found: C=59.37, H=6.73, N=2.98.

(B) Similarly, proceeding as in part (A) above but substituting the compounds prepared in Preparation 10(B) above for L-3-(3,4-dimethoxyphenyl)-2-(t-butoxycarbonylamino)propan-1-ol, the following compounds are prepared:

D-3-(3,4-dimethoxyphenyl)-2-(t-butoxycarbonylamino)-1-tosyloxypropane;
L-3-(3,4,5-trimethoxyphenyl)-2-(t-butoxycarbonylamino)-1-toxyloxypropane;
D-3-(3,4,5-trimethoxyphenyl)-2-(t-butoxycarbonylamino)-1-toxyloxypropane;
L-3-(3,4-dimethoxy-2,5-diethoxyphenyl)-2-(t-butoxycarbonylamino)-1-tosyloxypropane;
D-3-(3,4-dimethoxy-2,5-diethoxyphenyl)-2-(t-butoxycarbonylamino)-1-toxyloxypropane;
L-3-(3,4-dimethoxy-2,5-dipentoxyphenyl)-2-(t-butoxycarbonylamino)-1-tosyloxypropane; and
D-3-(3,4-dimethoxy-2,5-dipentoxyphenyl)-2-(t-butoxycarbonylamino)-1-tosyloxypropane.

PREPARATION 12

(Intermediates of Formula 15)

(A) Vinylmagnesium bromide (37.3 mL of 1.6M THF solution) was added to a −5° C. suspension of CuI (5.8 g, 29.8 mmol) in THF (75 mL). The mixture was cooled to −70° C. and a solution of L-3-(3,4-dimethoxyphenyl)-2-(t-butoxycarbonylamino)-1-tosyloxypropane (14, 4.6 g, 9.9 mmol) in THF (80 mL) was added slowly. The mixture was stirred at −70° C. for 30 minutes, then allowed to warm to 0° C. The resulting mixture was poured into aqueous NH$_4$Cl and extracted with ether. The organic layer was dried over MgSO$_4$, evaporated, and the residue purified by medium pressure chromatography to yield L-5-(3,4-dimethoxyphenyl)-4-(t-butoxycarbonylamino)pent-1-ene (15, 2.0 g, m.p. 91°–92° C., $[\alpha]_D^{25} = -20.9°$ (MeOH). Calculated for C$_{18}$H$_{27}$NO$_4$: C=67.26, H=8.47, N=4.36. Found: C=67.33, H=8.49, N=4.32.

(B) Similarly, proceeding as in part (A) above but substituting the compounds prepared in Preparation 11(B) above for L-3-(3,4-dimethoxyphenyl)-2-(t-butoxycarbonylamino)-1-tosyloxypropane, the following compounds are prepared:

D-5-(3,4-dimethoxyphenyl)-4-(t-butoxycarbonylamino)-pent-1-ene;
L-5-(3,4,5-trimethoxyphenyl)-4-(t-butoxycarbonylamino)pent-1-ene;
D-5-(3,4,5-trimethoxyphenyl)-4-(t-butoxycarbonylamino)pent-1-ene;
L-5-(3,4-dimethoxy-2,5-diethoxyphenyl)-4-(t-butoxycarbonylamino)pent-1-ene;
D-5-(3,4-dimethoxy-2,5-diethoxyphenyl)-4-(t-butoxycarbonylamino)pent-1-ene;
L-5-(3,4-dimethoxy-2,5-dipentoxyphenyl)-4-(t-butoxycarbonylamino)pent-1-ene; and
D-5-(3,4-dimethoxy-2,5-dipentoxyphenyl)-4-(t-butoxycarbonylamino)pent-1-ene.

PREPARATION 13

(Intermediates of Formula 16)

(A) A solution of L-5-(3,4-dimethoxyphenyl)-4-(t-butoxycarbonylamino)pent-1-ene (15, 1.6 g, 5 mmol) in THF (10 mL) was added to a 0° C. solution of disiamylborane (7.5 mmol) in THF (25 mL). The mixture was stirred at room temperature for one hour, cooled to 0° C., and 3N NaOH (1.7 mL) and 30% H$_2$O$_2$ (1.7 mL) added sequentially. The resulting solution was stirred at room temperature for 30 minutes, diluted with ether, and washed with water and brine. The ether was evaporated and the residue recrystallized from ether/hexane to yield D-5-(3,4-dimethoxyphenyl)-4-(t-butoxycarbonylamino)pentan-1-ol (16, 1.2 g, m.p. 73°–75° C., $[\alpha]_D^{25} = +0.89°$ (MeOH). Calculated for C$_{18}$H$_{29}$NO$_5$: C=63.69, H=8.61, N=4.13. Found: C=63.58, H=8.64, N=4.06.

(B) Similarly, proceeding as in part (A) above but substituting the compounds prepared in Preparation 12(B) for L-5-(3,4-dimethoxyphenyl)-4-(t-butoxycarbonylamino)-pent-1-ene, the following compounds are prepared:

L-5-(3,4-dimethoxyphenyl)-4-(t-butoxycarbonylamino)-pentan-1-ol;
L-5-(3,4,5-trimethoxyphenyl)-4-(t-butoxycarbonylamino)-pentan-1-ol;
D-5-(3,4,5-trimethoxyphenyl)-4-(t-butoxycarbonylamino)pentan-1-ol;
L-5-(3,4-dimethoxy-2,5-diethoxyphenyl)-4-(t-butoxycarbonylamino)pentan-1-ol;
D-5-(3,4-dimethoxy-2,5-diethoxyphenyl)-4-(t-butoxycarbonylamino)pentan-1-ol;
L-5-(3,4-dimethoxy-2,5-dipentoxyphenyl)-4-(t-butoxycarbonylamino)pentan-1-ol; and
D-5-(3,4-dimethoxy-2,5-dipentoxyphenyl)-4-(t-butoxycarbonylamino)pentan-1-ol.

PREPARATION 14

(Intermediates of Formula 17)

(A) A solution of D-5-(3,4-dimethoxyphenyl)-4-(t-butoxycarbonylamino)pentan-1-ol (16, 1.0 g, 2.98 mmol) and triethylamine (1.3 mL) in CH$_2$Cl$_2$ (15 mL) was cooled and methanesulfonyl chloride (0.26 mL, 3.3 mmol) was added. After 10 minutes, the mixture was added to water and the organic layer separated and dried over MgSO$_4$. The dichloromethane was evaporated and the resulting white solid was dissolved in acetone (10 mL). NaI (3 g) was added and the mixture was heated at reflux for 30 minutes. The mixture was then poured in water, extracted with ether, and the ether washed with aqueous NaHSO$_3$, water, and brine. The ether layer was then dried over MgSO$_4$ and evaporated to yield crude D-5-(3,4-dimethoxyphenyl)-4-(t-butoxycarbonylamino)-1-iodopentane (17) which was used at once.

(B) Similarly, proceeding as in part (A) above but substituting the compounds prepared in Preparation 13(B) for D-5-(3,4-dimethoxyphenyl)-4-(t-butoxycarbonylamino)-pentan-1-ol, the following compounds are prepared:

L-5-(3,4-dimethoxyphenyl)-4-(t-butoxycarbonylamino)-1-iodopentane;
L-5-(3,4,5-trimethoxyphenyl)-4-(t-butoxycarbonylamino)-1-iodopentane;
D-5-(3,4,5-trimethoxyphenyl)-4-(t-butoxycarbonylamino)-1-iodopentane;
L-5-(3,4-dimethoxy-2,5-diethoxyphenyl)-4-(t-butoxycarbonylamino)-1-iodopentane;
D-5-(3,4-dimethoxy-2,5-diethoxyphenyl)-4-(t-butoxycarbonylamino)-1-iodopentane;
L-5-(3,4-dimethoxy-2,5-dipentoxyphenyl)-4-(t-butoxycarbonylamino)-1-iodopentane; and D-5-(3,4-dimethoxy-2,5-dipentoxyphenyl)-4-(t-butoxycarbonylamino)-1-iodopentane.

PREPARATION 15

(Intermediates of Formula 18)

(A) A solution of 2-(3,4-dimethoxyphenyl)-2-isopropylacetonitrile (6a, 1.3 g, 6 mmol), in THF (5 mL) was added to −70° C. solution of lithium diisopropylamide (LDA, 6 mmol) in THF (20 mL). After 10 minutes at −70° C., a solution of crude L-5-(3,4-dimethoxyphenyl)-4-(t-butoxycarbonylamino)-1-iodopentane (17, ca. 3 mmol) in THF (5 mL) was added and the resulting mixture allowed to warm to 0° C. Aqueous HCl was added and the mixture extracted with ether. The organic layer was washed with water and brine, dried over MgSO4, evaporated, and the residue purified by medium pressure chromatography (30% ethyl acetate-hexane) to yield (2R)-1-(3,4-dimethoxyphenyl)-2-t-butoxycarbonylamino-6-cyano-6-(i-propyl)-6-(3,4-dimethoxyphenyl)hexane (18, 400 mg).

(B) Similarly, proceeding as in part (A) above but substituting the compounds prepared in Preparation 14(B) for D-5-(3,4-dimethoxyphenyl)-4-(t-butoxycarbonylamino)-1-iodopentane, the following compounds are prepared:

(2S)-1-(3,4-dimethoxyphenyl)-2-(t-butoxycarbonylamino)-6-cyano-6-(i-propyl)-6-(3,4-dimethoxyphenyl)hexane;

(2R)-1-(3,4,5-trimethoxyphenyl)-2-(t-butoxycarbonylamino)-6-cyano-6-(i-propyl)-6-(3,4-dimethoxyphenyl)hexane;

(2S)-1-(3,4,5-trimethoxyphenyl)-2-(t-butoxycarbonylamino)-6-cyano-6-(i-propyl)-6-(3,4-dimethoxyphenyl)hexane;

(2R)-1-(3,4-dimethoxy-2,5-diethoxyphenyl)-2-(t-butoxycarbonylamino)-6-cyano-6-(i-propyl)-6-(3,4-dimethoxyphenyl)hexane;

(2S)-1-(3,4-dimethoxy-2,5-diethoxyphenyl)-2-(t-butoxycarbonylamino)-6-cyano-6-(i-propyl)-6-(3,4-dimethoxyphenyl)hexane;

(2R)-1-(3,4-dimethoxy-2,5-dipentoxyphenyl)-2-(t-butoxycarbonylamino)-6-cyano-6-(i-propyl)-6-(3,4-dimethoxyphenyl)hexane; and (2S)-1-(3,4-dimethoxy-2,5-dipentoxyphenyl)-2-(t-butoxycarbonylamino)-6-cyano-6-(i-propyl)-6-(3,4-dimethoxyphenyl)hexane.

PREPARATION 16

(Intermediates of Formula 19)

(A) A solution of (2R)-1-(3,4-dimethoxyphenyl)-2-t-butoxycarbonylamino-6-cyano-6-(i-propyl)-6-(3,4-dimethoxyphenyl)hexane (18, 400 mg) in formic acid (5 mL) was heated at reflux for 15 minutes. The mixture was evaporated and the residue treated with formic-acetic anhydride (2 mL). Ether was added and the mixture washed with water, aqueous NaHCO3, and brine, and the solution dried over Na2SO4. The ether was evaporated and the residue purified by medium pressure chromatography using ethyl acetate. The first component to elute was (2R, 6S)-1-(3,4-dimethoxyphenyl)-2-formylamino-6-cyano-6-(i-propyl)-6-(3,4-dimethoxyphenyl)hexane (19A, 180 mg, $[\alpha]_D^{25} = -4.3°$ (MeOH)). The second component to elute was (2R, 6R)-1-(3,4-dimethoxyphenyl)-2-formylamino-6-cyano-6-(i-propyl)-6-(3,4-dimethoxyphenyl)hexane (19B, 40 mg, $[\alpha]_D^{25} = +2.3°$ (MeOH)).

(B) Similarly, proceeding as in part (A) above but substituting the compounds prepared in Preparation 15(B) for (2R)-1-(3,4-dimethoxyphenyl)-2-t-butoxycarbonylamino-6-cyano-6-(i-propyl)-6-(3,4-dimethoxyphenyl)hexane, the following compounds are prepared:

(2S, 6R)-1-(3,4-dimethoxyphenyl)-2-formylamino-6-cyano-6-(i-propyl)-6-(3,4-dimethoxyphenyl)hexane;

(2S, 6S)-1-(3,4-dimethoxyphenyl)-2-formylamino-6-cyano-6-(i-propyl)-6-(3,4-dimethoxyphenyl)hexane;

(2R, 6R)-1-(3,4,5-trimethoxyphenyl)-2-formylamino-6-cyano-6-(i-propyl)-6-(3,4-dimethoxyphenyl)hexane;

(2R, 6S)-1-(3,4,5-trimethoxyphenyl)-2-formylamino-B 6-cyano-6-(i-propyl)-6-(3,4-dimethoxyphenyl)hexane;

(2S, 6R)-1-(3,4,5-trimethoxyphenyl)-2-formylamino-6-cyano-6-(i-propyl)-6-(3,4-dimethoxyphenyl)hexane;

(2S, 6S)-1-(3,4,5-trimethoxyphenyl)-2-formylamino-6-cyano-6-(i-propyl)-6-(3,4-dimethoxyphenyl)hexane;

(2R, 6R)-1-(3,4-dimethoxy-2,5-diethoxyphenyl)-2-formylamino-6-cyano-6-(i-propyl)-6-(3,4-dimethoxyphenyl)-hexane;

(2R, 6S)-1-(3,4-dimethoxy-2,5-diethoxyphenyl)-2-formylamino-6-cyano-6-(i-propyl)-6-(3,4-dimethoxyphenyl)-hexane;

(2S, 6R)-1-(3,4-dimethoxy-2,5-diethoxyphenyl)-2-formylamino-6-cyano-6-(i-propyl)-6-(3,4-dimethoxyphenyl)-hexane;

(2S, 6S)-1-(3,4-dimethoxy-2,5-diethoxyphenyl)-2-formylamino-6-cyano-6-(i-propyl)-6-(3,4-dimethoxyphenyl)-hexane;

(2R, 6R)-1-(3,4-dimethoxy-2,5-dipentoxyphenyl)-2-formylamino-6-cyano-6-(i-propyl)-6-(3,4-dimethoxyphenyl)-hexane;

(2R, 6S)-1-(3,4-dimethoxy-2,5-dipentoxyphenyl)-2-formylamino-6-cyano-6-(i-propyl)-6-(3,4-dimethoxyphenyl)-hexane;

(2S, 6R)-1-(3,4-dimethoxy-2,5-dipentoxyphenyl)-2-formylamino-6-cyano-6-(i-propyl)-6-(3,4-dimethoxyphenyl)-hexane; and (2S, 6S)-1-(3,4-dimethoxy-2,5-dipentoxyphenyl)-2-formylamino-6-cyano-6-(i-propyl)-6-(3,4-dimethoxyphenyl)-hexane.

PREPARATION 17

(Intermediates of Formula 20)

(A) Phosphorous oxychloride (POCl3, 2.3 mL) was added to a solution of (2R, 6S)-1-(3,4-dimethoxyphenyl)-2-formylamino-6-cyano-6-(i-propyl)-6-(3,4-dimethoxyphenyl)-hexane (19A, 5.1 g, 11 mmol) in acetonitrile (75 mL) and the mixture stirred at room temperature for two hours. The resulting mixture was evaporated, and the residue dissolved in ether and extracted with cold aqueous NH4OH. The ether was evaporated, the residue was dissolved in ethanol (100 mL), and sodium borohydride (0.5 g) added. The mixture was stirred for one hour, then added to water, acidified with HCl, and extracted with ether. The organic layer was washed with brine, dried, and evaporated to a colorless oil to yield (3R, 4'S)-3-[4-(3,4-dimethoxyphenyl)-4-isopropyl-4-cyanobutyl]-6,7-dimethoxy-1,2,3,4-tetrahydroisoquinoline (20A).

(B) Similarly, proceeding as in part (A) above but substituting the compounds prepared in Preparation 16(B) for (2R, 6S)-1-(3,4-dimethoxyphenyl)-2-formylamino-6-cyano-6-(i-propyl)-6-(3,4-dimethoxyphenyl)hexane, the following compounds are prepared:

(3S, 4'S)-3-[4-(3,4-dimethoxyphenyl)-4-isopropyl-4-cyanobutyl]-6,7-dimethoxyphenyl-1,2,3,4-tetrahydroisoquinoline;

(3R, 4'R)-3-[4-(3,4-dimethoxyphenyl)-4-isopropyl-4-cyanobutyl]-6,7,8-trimethoxyphenyl-1,2,3,4-tetrahydroisoquinoline;
(3R, 4'S)-3-[4-(3,4-dimethoxyphenyl)-4-isopropyl-4-cyanobutyl]-6,7,8-trimethoxyphenyl-1,2,3,4-tetrahydroisoquinoline;
(3S, 4'R)-3-[4-(3,4-dimethoxyphenyl)-4-isopropyl-4-cyanobutyl]-6,7,8-trimethoxyphenyl-1,2,3,4-tetrahydroisoquinoline;
(3S, 4'S)-3-[4-(3,4-dimethoxyphenyl)-4-isopropyl-4-cyanobutyl]-6,7,8-trimethoxyphenyl-1,2,3,4-tetrahydroisoquinoline;
(3R, 4'R)-3-[4-(3,4-dimethoxyphenyl)-4-isopropyl-4-cyanobutyl]-6,7-dimethoxy-5,8-diethoxyphenyl-1,2,3,4-tetrahydroisoquinoline;
(3R, 4'S)-3-[4-(3,4-dimethoxyphenyl)-4-isopropyl-4-cyanobutyl]-6,7-dimethoxy-5,8-diethoxyphenyl-1,2,3,4-tetrahydroisoquinoline;
(3S, 4'R)-3-[4-(3,4-dimethoxyphenyl)-4-isopropyl-4-cyanobutyl]-6,7-dimethoxy-5,8-diethoxyphenyl-1,2,3,4-tetrahydroisoquinoline;
(3S, 4'S)-3-[4-(3,4-dimethoxyphenyl)-4-isopropyl-4-cyanobutyl]-6,7-dimethoxy-5,8-diethoxyphenyl-1,2,3,4-tetrahydroisoquinoline;
(3R, 4'R)-3-[4-(3,4-dimethoxyphenyl)-4-isopropyl-4-cyanobutyl]-6,7-dimethoxy-5,8-dipentoxyphenyl-1,2,3,4-tetrahydroisoquinoline;
(3R, 4'S)-3-[4-(3,4-dimethoxyphenyl)-4-isopropyl-4-cyanobutyl]-6,7-dimethoxy-5,8-dipentoxyphenyl-1,2,3,4-tetrahydroisoquinoline;
(3S, 4'R)-3-[4-(3,4-dimethoxyphenyl)-4-isopropyl-4-cyanobutyl]-6,7-dimethoxy-5,8-dipentoxyphenyl-1,2,3,4-tetrahydroisoquinoline; and
(3S, 4'S)-3-[4-(3,4-dimethoxyphenyl)-4-isopropyl-4-cyanobutyl]-6,7-dimethoxy-5,8-dipentoxyphenyl-1,2,3,4-tetrahydroisoquinoline.

PREPARATION 18

(Intermediates of Formula 21)

(A) A solution of 2-(3,4-dimethoxyphenyl)-2-isopropylacetonitrile (6a) in toluene is slowly added to sodium amide (1.5 eq) in toluene, and the resulting mixture warmed to 80°–90° C. for one hour. The mixture was then cooled to 15° C. and 1-bromo-3-chloropropane (2 eq) slowly added and stirred for two hours at room temperature. The mixture is then carefully poured into ice water, extracted with $CH_2Cl_2$, and vacuum distilled to yield 2-(3,4-dimethoxyphenyl)-2-isopropyl-2-(3-chloropropyl)acetonitrile (21, b.p. 160°–165°/0.05 mmHg).

(B) Similarly, proceeding as in part (A) above but substituting the compounds prepared in Preparation 3(B-C) for 2-(3,4-dimethoxyphenyl)-2-isopropylacetonitrile, the following compounds are prepared:
2-(3,4-dimethoxyphenyl)-2-methyl-2-(3-chloropropyl)acetonitrile;
2-(3,4-dimethoxyphenyl)-2-ethyl-2-(3-chloropropyl)acetonitrile;
2-(3,4-dimethoxyphenyl)-2-(but-2-yl)-2-(3-chloropropyl)acetonitrile;
2-(3,4-dimethoxyphenyl)-2-(pent-3-yl)-2-(3-chloropropyl)acetonitrile;
2-(1,3-benzodioxol-2-yl)-2-methyl-2-(3-chloropropyl)acetonitrile;
2-(1,3-benzodioxol-2-yl)-2-ethyl-2-(3-chloropropyl)acetonitrile;
2-(1,3-benzodioxol-2-yl)-2-isopropyl-2-(3-chloropropyl)acetonitrile;
2-(1,3-benzodioxol-2-yl)-2-(but-2-yl)-2-(3-chloropropyl)acetonitrile;
2-(1,3-benzodioxol-2-yl)-2-(pent-3-yl)-2-(3-chloropropyl)acetonitrile;
2-(1,4-benzodioxan-2-yl)-2-methyl-2-(3-chloropropyl)acetonitrile;
2-(1,4-benzodioxan-2-yl)-2-ethyl-2-(3-chloropropyl)acetonitrile;
2-(1,4-benzodioxan-2-yl)-2-isopropyl-2-(3-chloropropyl)acetonitrile;
2-(1,4-benzodioxan-2-yl)-2-(but-2-yl)-2-(3-chloropropyl)acetonitrile; and
2-(1,4-benzodioxan-2-yl)-2-(pent-3-yl)-2-(3-chloropropyl)acetonitrile.

PREPARATION 19

(Intermediates of Formula 22)

(A) A solution of 2-(3,4-dimethoxyphenyl)-2-isopropyl-2-(3-chloropropyl)acetonitrile (22, 21.4 g, 72 mmol), sodium iodide (30 g), and acetone (250 mL) was heated at reflux for 12 hours. The mixture was then filtered, the acetone evaporated, and the residue partitioned between ether and water. The organic layer was washed with aqueous $NaSO_3$ and brine, dried over $Na_2SO_4$, and evaporated to yield 2-(3,4-dimethoxyphenyl)-2-isopropyl-2-(3-iodopropyl)acetonitrile (22, 28 g) as a thick oil.

(B) Similarly, proceeding as in part (A) above but substituting the compounds prepared in Preparation 18(B) for 2-(3,4-dimethoxyphenyl)-2-isopropyl-2-(3-chloropropyl)acetonitrile, the following compounds are prepared:
2-(3,4-dimethoxyphenyl)-2-methyl-2-(3-iodopropyl)acetonitrile;
2-(3,4-dimethoxyphenyl)-2-ethyl-2-(3-iodopropyl)acetonitrile;
2-(3,4-dimethoxyphenyl)-2-(but-2-yl)-2-(3-iodopropyl)acetonitrile;
2-(3,4-dimethoxyphenyl)-2-(pent-3-yl)-2-(3-iodopropyl)acetonitrile;
2-(1,3-benzodioxol-2-yl)-2-methyl-2-(3-iodopropyl)acetonitrile;
2-(1,3-benzodioxol-2-yl)-2-ethyl-2-(3-iodopropyl)acetonitrile;
2-(1,3-benzodioxol-2-yl)-2-isopropyl-2-(3-iodopropyl)acetonitrile;
2-(1,3-benzodioxol-2-yl)-2-(but-2-yl)-2-(3-iodopropyl)acetonitrile;
2-(1,3-benzodioxol-2-yl)-2-(pent-3-yl)-2-(3-iodopropyl)acetonitrile;
2-(1,4-benzodioxan-2-yl)-2-methyl-2-(3-iodopropyl)acetonitrile;
2-(1,4-benzodioxan-2-yl)-2-ethyl-2-(3-iodopropyl)acetonitrile;
2-(1,4-benzodioxan-2-yl)-2-isopropyl-2-(3-iodopropyl)acetonitrile;
2-(1,4-benzodioxan-2-yl)-2-(but-2-yl)-2-(3-iodopropyl)acetonitrile; and
2-(1,4-benzodioxan-2-yl)-2-(pent-3-yl)-2-(3-iodopropyl)acetonitrile.

PREPARATION 20

(Intermediates of Formula 23)

(A) A 1.6M solution of n-butyllithium in hexane (91.8 mL, 147 mmol) was added to a −20° C. solution of diisopropylamine (21 mL, 150 mmol) in THF (480 mL). Hexamethylphosphoramide (56 mL) was added and the mixture maintained at −20° C. while a solution of 3-(3,4-dimethoxyphenyl)propionic acid (15.1 g, 72 mmol) in THF (75 mL) was added. The resulting solution was stirred at room temperature for one hour, and then cooled to −50° C. A solution of 2-(3,4-dimethoxyphenyl)-2-isopropyl-2-(3-iodopropyl)acetonitrile (22, 27.9 g, 72 mmol) was added, and the mixture allowed to warm to room temperature while stirring for 12 hours. The resulting mixture was added to water, acidified with HCl, and extracted three times with ether. The organic layer was washed with aqueous $Na_2SO_3$ and brine, dried over $Na_2SO_4$, and evaporated to yield 1-(3,4-dimethoxyphenyl)-2-carboxy-6-cyano-6-(i-propyl)-6-(3,4-dimethoxyphenyl)hexane (23, 31 g) as a thick oil.

(B) Similarly, proceeding as in part (A) above but substituting the compounds prepared in Preparation 19(B) for 2-(3,4-dimethoxyphenyl)-2-isopropyl-2-(3-iodopropyl)acetonitrile, the following compounds are prepared:

1-(3,4-dimethoxyphenyl)-2-carboxy-6-(3,4-dimethoxyphenyl)-6-methyl-6-cyanohexane;

1-(3,4-dimethoxyphenyl)-2-carboxy-6-(3,4-dimethoxyphenyl)-6-ethyl-6-cyanohexane;

1-(3,4-dimethoxyphenyl)-2-carboxy-6-(3,4-dimethoxyphenyl)-6-(but-2-yl)-6-cyanohexane;

1-(3,4-dimethoxyphenyl)-2-carboxy-6-(3,4-dimethoxyphenyl)-6-(pent-3-yl)-6-cyanohexane;

1-(3,4-dimethoxyphenyl)-2-carboxy-6-(1,3-benzodioxol-2-yl)-6-methyl-6-cyanohexane;

1-(3,4-dimethoxyphenyl)-2-carboxy-6-(1,3-benzodioxol-2-yl)-6-ethyl-6-cyanohexane;

1-(3,4-dimethoxyphenyl)-2-carboxy-6-(1,3-benzodioxol-2-yl)-6-isopropyl-6-cyanohexane;

1-(3,4-dimethoxyphenyl)-2-carboxy-6-(1,3-benzodioxol-2-yl)-6-(but-2-yl)-6-cyanohexane;

1-(3,4-dimethoxyphenyl)-2-carboxy-6-(1,3-benzodioxol-2-yl)-6-(pent-3-yl)-6-cyanohexane;

1-(3,4-dimethoxyphenyl)-2-carboxy-6-(1,4-benzodioxan-2-yl)-6-methyl-6-cyanohexane;

1-(3,4-dimethoxyphenyl)-2-carboxy-6-(1,4-benzodioxan-2-yl)-6-ethyl-6-cyanohexane;

1-(3,4-dimethoxyphenyl)-2-carboxy-6-(1,4-benzodioxan-2-yl)-6-isopropyl-6-cyanohexane;

1-(3,4-dimethoxyphenyl)-2-carboxy-6-(1,4-benzodioxan-2-yl)-6-(but-2-yl)-6-cyanohexane; and 1-(3,4-dimethoxyphenyl)-2-carboxy-6-(1,4-benzodioxan-2-yl)-6-(pent-3-yl)-6-cyanohexane.

PREPARATION 21

(Intermediates of Formula 19 via Scheme III)

(A) A mixture of 1-(3,4-dimethoxyphenyl)-2-carboxy-6-cyano-6-(i-propyl)-6-(3,4-dimethoxyphenyl)hexane (24, 16.6 g, 35 mmol), triethylamine (5.9 mL), diphenylphosphoryl azide (7.6 mL, 35 mmol), and toluene (200 mL) was heated to reflux temperature and maintained at reflux for 15 minutes. The solvents were removed under reduced pressure and the residue dissolved in dimethoxyethane (DME, 200 mL). The solution was cooled in an ice bath and $NaBH_4$ (1.6 g) slowly added. The solution was stirred for one hour, concentrated en vacuo, and partitioned between aqueous HCl (5%) and ethyl acetate. The organic layer was washed with water and brine, dried over $Na_2SO_4$, and evaporated to yield 1-(3,4-dimethoxyphenyl)-2-formylamino-6-cyano-6-(i-propyl)-6-(3,4-dimethoxyphenyl)hexane (19, 20.6 g) as a diastereomeric mixture of thick oils.

(B) Similarly, proceeding as in part (A) above but substituting the compounds prepared in Preparation 20(B) for 1-(3,4-dimethoxyphenyl)-2-carboxy-6-cyano-6-(i-propyl)-6-(3,4-dimethoxyphenyl)hexane, the following compounds are prepared:

1-(3,4-dimethoxyphenyl)-2-formylamino-6-(3,4-dimethoxyphenyl)-6-methyl-6-cyanohexane;

1-(3,4-dimethoxyphenyl)-2-formylamino-6-(3,4-dimethoxyphenyl)-6-ethyl-6-cyanohexane;

1-(3,4-dimethoxyphenyl)-2-formylamino-6-(3,4-dimethoxyphenyl)-6-(but-2-yl)-6-cyanohexane;

1-(3,4-dimethoxyphenyl)-2-formylamino-6-(3,4-dimethoxyphenyl)-6-(pent-3-yl)-6-cyanohexane;

1-(3,4-dimethoxyphenyl)-2-formylamino-6-(1,3-benzodioxol-2-yl)-6-methyl-6-cyanohexane;

1-(3,4-dimethoxyphenyl)-2-formylamino-6-(1,3-benzodioxol-2-yl)-6-ethyl-6-cyanohexane;

1-(3,4-dimethoxyphenyl)-2-formylamino-6-(1,3-benzodioxol-2-yl)-6-isopropyl-6-cyanohexane;

1-(3,4-dimethoxyphenyl)-2-formylamino-6-(1,3-benzodioxol-2-yl)-6-(but-2-yl)-6-cyanohexane;

1-(3,4-dimethoxyphenyl)-2-formylamino-6-(1,3-benzodioxol-2-yl)-6-(pent-3-yl)-6-cyanohexane;

1-(3,4-dimethoxyphenyl)-2-formylamino-6-(1,4-benzodioxan-2-yl)-6-methyl-6-cyanohexane;

1-(3,4-dimethoxyphenyl)-2-formylamino-6-(1,4-benzodioxan-2-yl)-6-ethyl-6-cyanohexane;

1-(3,4-dimethoxyphenyl)-2-formylamino-6-(1,4-benzodioxan-2-yl)-6-isopropyl-6-cyanohexane;

1-(3,4-dimethoxyphenyl)-2-formylamino-6-(1,4-benzodioxan-2-yl)-6-(but-2-yl)-6-cyanohexane; and 1-(3,4-dimethoxyphenyl)-2-formylamino-6-(1,4-benzodioxan-2-yl)-6-(pent-3-yl)-6-cyanohexane.

EXAMPLE 1

(Compounds of Formula 1 via Scheme I)

(A) A mixture of 1-(3,4-dimethoxyphenyl)-2-amino-6-cyano-6-(i-propyl)-6-(3,4-dimethoxyphenyl)hexane (11, 52.3 g, 0.12 mol), paraformaldehyde (27 g, Aldrich) and formic acid (97%, 380 mL) was heated at 85°–95° C. for 4–5 hours. Most of the formic acid was removed by vacuum distillation, and the residue cooled to room temperature and diluted with ethyl acetate (700 mL) and water (300 mL). Saturated brine (300 mL) was carefully added, and the resulting mixture extracted with brine (300 mL). The organic layer was then separated and concentrated to about 100 mL. The resulting mixture was applied to a silica gel column (300 g silica gel) and eluted with ethyl acetate. After 500 mL of eluate was collected, the remainder was eluted with acetone. The product fractions were collected and evaporated to yield racemic 3-[4-(3,4-dimethoxyphenyl)-4-isopropyl-4-cyanobutyl]-6,7-dimethoxy-N-methyl-1,2,3,4-tetrahydroisoquinoline (1, 53.7 g, MS m/e 466(M+)) as a thick oil.

(B) Similarly, proceeding as in part (A) above but substituting the compounds prepared in Preparation 9(B) for 1-(3,4-dimethoxyphenyl)-2-amino-6-cyano-6-(i-propyl)-6-(3,4-dimethoxyphenyl)hexane, the following compounds are prepared:

3-[4-(3,4-dimethoxyphenyl)-4-methyl-4-cyanobutyl]-6,7-dimethoxy-N-methyl-1,2,3,4-tetrahydroisoquinoline;

3-[4-(3,4-dimethoxyphenyl)-4-ethyl-4-cyanobutyl]-6,7-dimethoxy-N-methyl-1,2,3,4-tetrahydroisoquinoline;

3-[4-(3,4-dimethoxyphenyl)-4-(but-2-yl)-4-cyanobutyl]-6,7-dimethoxy-N-methyl-1,2,3,4-tetrahydroisoquinoline;

3-[4-(3,4-dimethoxyphenyl)-4-(pent-3-yl)-4-cyanobutyl]-6,7-dimethoxy-N-methyl-1,2,3,4-tetrahydroisoquinoline;

3-[4-(1,3-benzodioxol-2-yl)-4-methyl-4-cyanobutyl]-6,7-dimethoxy-N-methyl-1,2,3,4-tetrahydroisoquinoline;

3-[4-(1,3-benzodioxol-2-yl)-4-ethyl-4-cyanobutyl]-6,7-dimethoxy-N-methyl-1,2,3,4-tetrahydroisoquinoline;

3-[4-(1,3-benzodioxol-2-yl)-4-(prop-2-yl)-4-cyanobutyl]-6,7-dimethoxy-N-methyl-1,2,3,4-tetrahydroisoquinoline;

3-[4-(1,3-benzodioxol-2-yl)-4-(but-2-yl)-4-cyanobutyl]-6,7-dimethoxy-N-methyl-1,2,3,4-tetrahydroisoquinoline;

3-[4-(1,3-benzodioxol-2-yl)-4-(pent-3-yl)-4-cyanobutyl]-6,7-dimethoxy-N-methyl-1,2,3,4-tetrahydroisoquinoline;

3-[4-(1,4-benzodioxan-2-yl)-4-methyl-4-cyanobutyl]-6,7-dimethoxy-N-methyl-1,2,3,4-tetrahydroisoquinoline;

3-[4-(1,4-benzodioxan-2-yl)-4-ethyl-4-cyanobutyl]-6,7-dimethoxy-N-methyl-1,2,3,4-tetrahydroisoquinoline;

3-[4-(1,4-benzodioxan-2-yl)-4-(prop-2-yl)-4-cyanobutyl]-6,7-dimethoxy-N-methyl-1,2,3,4-tetrahydroisoquinoline;

3-[4-(1,4-benzodioxan-2-yl)-4-(but-2-yl)-4-cyanobutyl]-6,7-dimethoxy-N-methyl-1,2,3,4-tetrahydroisoquinoline;

3-[4-(1,4-benzodioxan-2-yl)-4-(pent-3-yl)-4-cyanobutyl]-6,7-dimethoxy-N-methyl-1,2,3,4-tetrahydroisoquinoline;

3-[4-(3,4-dimethoxyphenyl)-4-methyl-4-cyanobutyl]-6,7,8-trimethoxy-N-methyl-1,2,3,4-tetrahydroisoquinoline;

3-[4-(3,4-dimethoxyphenyl)-4-ethyl-4-cyanobutyl]-6,7,8-trimethoxy-N-methyl-1,2,3,4-tetrahydroisoquinoline;

3-[4-(3,4-dimethoxyphenyl)-4-(but-2-yl)-4-cyanobutyl]-6,7,8-trimethoxy-N-methyl-1,2,3,4-tetrahydroisoquinoline;

3-[4-(3,4-dimethoxyphenyl)-4-(pent-3-yl)-4-cyanobutyl]-6,7,8-trimethoxy-N-methyl-1,2,3,4-tetrahydroisoquinoline;

3-[4-(1,3-benzodioxol-2-yl)-4-methyl-4-cyanobutyl]-6,7,8-trimethoxy-N-methyl-1,2,3,4-tetrahydroisoquinoline;

3-[4-(1,3-benzodioxol-2-yl)-4-ethyl-4-cyanobutyl]-6,7,8-trimethoxy-N-methyl-1,2,3,4-tetrahydroisoquinoline;

3-[4-(1,3-benzodioxol-2-yl)-4-(prop-2-yl)-4-cyanobutyl]-6,7,8-trimethoxy-N-methyl-1,2,3,4-tetrahydroisoquinoline;

3-[4-(1,3-benzodioxol-2-yl)-4-(but-2-yl)-4-cyanobutyl]-6,7,8-trimethoxy-N-methyl-1,2,3,4-tetrahydroisoquinoline;

3-[4-(1,3-benzodioxol-2-yl)-4-(pent-3-yl)-4-cyanobutyl]-6,7,8-trimethoxy-N-methyl-1,2,3,4-tetrahydroisoquinoline;

3-[4-(1,4-benzodioxan-2-yl)-4-methyl-4-cyanobutyl]-6,7,8-trimethoxy-N-methyl-1,2,3,4-tetrahydroisoquinoline;

3-[4-(1,4-benzodioxan-2-yl)-4-ethyl-4-cyanobutyl]-6,7,8-trimethoxy-N-methyl-1,2,3,4-tetrahydroisoquinoline;

3-[4-(1,4-benzodioxan-2-yl)-4-(prop-2-yl)-4-cyanobutyl]-6,7,8-trimethoxy-N-methyl-1,2,3,4-tetrahydroisoquinoline;

3-[4-(1,4-benzodioxan-2-yl)-4-(but-2-yl)-4-cyanobutyl]-6,7,8-trimethoxy-N-methyl-1,2,3,4-tetrahydroisoquinoline;

3-[4-(1,4-benzodioxan-2-yl)-4-(pent-3-yl)-4-cyanobutyl]-6,7,8-trimethoxy-N-methyl-1,2,3,4-tetrahydroisoquinoline;

3-[4-(3,4-dimethoxyphenyl)-4-methyl-4-cyanobutyl]-5,6,7-trimethoxy-N-methyl-1,2,3,4-tetrahydroisoquinoline;

3-[4-(3,4-dimethoxyphenyl)-4-ethyl-4-cyanobutyl]-5,6,7-trimethoxy-N-methyl-1,2,3,4-tetrahydroisoquinoline;

3-[4-(3,4-dimethoxyphenyl)-4-(but-2-yl)-4-cyanobutyl]-5,6,7-trimethoxy-N-methyl-1,2,3,4-tetrahydroisoquinoline;

3-[4-(3,4-dimethoxyphenyl)-4-(pent-3-yl)-4-cyanobutyl]-5,6,7-trimethoxy-N-methyl-1,2,3,4-tetrahydroisoquinoline;

3-[4-(1,3-benzodioxol-2-yl)-4-methyl-4-cyanobutyl]-5,6,7-trimethoxy-N-methyl-1,2,3,4-tetrahydroisoquinoline;

3-[4-(1,3-benzodioxol-2-yl)-4-ethyl-4-cyanobutyl]-5,6,7-trimethoxy-N-methyl-1,2,3,4-tetrahydroisoquinoline;

3-[4-(1,3-benzodioxol-2-yl)-4-(prop-2-yl)-4-cyanobutyl]-5,6,7-trimethoxy-N-methyl-1,2,3,4-tetrahydroisoquinoline;

3-[4-(1,3-benzodioxol-2-yl)-4-(but-2-yl)-4-cyanobutyl]-5,6,7-trimethoxy-N-methyl-1,2,3,4-tetrahydroisoquinoline;

3-[4-(1,3-benzodioxol-2-yl)-4-(pent-3-yl)-4-cyanobutyl]-5,6,7-trimethoxy-N-methyl-1,2,3,4-tetrahydroisoquinoline;

3-[4-(1,4-benzodioxan-2-yl)-4-methyl-4-cyanobutyl]-5,6,7-trimethoxy-N-methyl-1,2,3,4-tetrahydroisoquinoline;

3-[4-(1,4-benzodioxan-2-yl)-4-ethyl-4-cyanobutyl]-5,6,7-trimethoxy-N-methyl-1,2,3,4-tetrahydroisoquinoline;

3-[4-(1,4-benzodioxan-2-yl)-4-(prop-2-yl)-4-cyanobutyl]-5,6,7-trimethoxy-N-methyl-1,2,3,4-tetrahydroisoquinoline;

3-[4-(1,4-benzodioxan-2-yl)-4-(but-2-yl)-4-cyanobutyl]-5,6,7-trimethoxy-N-methyl-1,2,3,4-tetrahydroisoquinoline;

3-[4-(1,4-benzodioxan-2-yl)-4-(pent-3-yl)-4-cyanobutyl]-5,6,7-trimethoxy-N-methyl-1,2,3,4-tetrahydroisoquinoline;

3-[4-(3,4-dimethoxyphenyl)-4-methyl-4-cyanobutyl]-5,6,7,8-tetramethoxy-N-methyl-1,2,3,4-tetrahydroisoquinoline;

3-[4-(3,4-dimethoxyphenyl)-4-ethyl-4-cyanobutyl]-5,6,7,8-tetramethoxy-N-methyl-1,2,3,4-tetrahydroisoquinoline;

3-[4-(3,4-dimethoxyphenyl)-4-(but-2-yl)-4-cyanobutyl]-5,6,7,8-tetramethoxy-N-methyl-1,2,3,4-tetrahydroisoquinoline;

3-[4-(3,4-dimethoxyphenyl)-4-(pent-3-yl)-4-cyanobutyl]-5,6,7,8-tetramethoxy-N-methyl-1,2,3,4-tetrahydroisoquinoline;

3-[4-(1,3-benzodioxol-2-yl)-4-methyl-4-cyanobutyl]-5,6,7,8-tetramethoxy-N-methyl-1,2,3,4-tetrahydroisoquinoline;

3-[4-(1,3-benzodioxol-2-yl)-4-ethyl-4-cyanobutyl]-5,6,7,8-tetramethoxy-N-methyl-1,2,3,4-tetrahydroisoquinoline;

3-[4-(1,3-benzodioxol-2-yl)-4-(prop-2-yl)-4-cyanobutyl]-5,6,7,8-tetramethoxy-N-methyl-1,2,3,4-tetrahydroisoquinoline;

3-[4-(1,3-benzodioxol-2-yl)-4-(but-2-yl)-4-cyanobutyl]-5,6,7,8-tetramethoxy-N-methyl-1,2,3,4-tetrahydroisoquinoline;

3-[4-(1,3-benzodioxol-2-yl)-4-(pent-3-yl)-4-cyanobutyl]-5,6,7,8-tetramethoxy-N-methyl-1,2,3,4-tetrahydroisoquinoline;

3-[4-(1,4-benzodioxan-2-yl)-4-methyl-4-cyanobutyl]-5,6,7,8-tetramethoxy-N-methyl-1,2,3,4-tetrahydroisoquinoline;

3-[4-(1,4-benzodioxan-2-yl)-4-ethyl-4-cyanobutyl]-5,6,7,8-tetramethoxy-N-methyl-1,2,3,4-tetrahydroisoquinoline;

3-[4-(1,4-benzodioxan-2-yl)-4-(prop-2-yl)-4-cyanobutyl]-5,6,7,8-tetramethoxy-N-methyl-1,2,3,4-tetrahydroisoquinoline;

3-[4-(1,4-benzodioxan-2-yl)-4-(but-2-yl)-4-cyanobutyl]-5,6,7,8-tetramethoxy-N-methyl-1,2,3,4-tetrahydroisoquinoline;

3-[4-(1,4-benzodioxan-2-yl)-4-(pent-3-yl)-4-cyanobutyl]-5,6,7,8-tetramethoxy-N-methyl-1,2,3,4-tetrahydroisoquinoline;

3-[4-(3,4-dimethoxyphenyl)-4-methyl-4-cyanobutyl]-6,7-dimethoxy-5,8-diethoxy-N-methyl-1,2,3,4-tetrahydroisoquinoline;

3-[4-(3,4-dimethoxyphenyl)-4-ethyl-4-cyanobutyl]-6,7-dimethoxy-5,8-diethoxy-N-methyl-1,2,3,4-tetrahydroisoquinoline;

3-[4-(3,4-dimethoxyphenyl)-4-(but-2-yl)-4-cyanobutyl]-6,7-dimethoxy-5,8-diethoxy-N-methyl-1,2,3,4-tetrahydroisoquinoline;

3-[4-(3,4-dimethoxyphenyl)-4-(pent-3-yl)-4-cyanobutyl]-6,7-dimethoxy-5,8-diethoxy-N-methyl-1,2,3,4-tetrahydroisoquinoline;

3-[4-(1,3-benzodioxol-2-yl)-4-methyl-4-cyanobutyl]-6,7-dimethoxy-5,8-diethoxy-N-methyl-1,2,3,4-tetrahydroisoquinoline;

3-[4-(1,3-benzodioxol-2-yl)-4-ethyl-4-cyanobutyl]-6,7-dimethoxy-5,8-diethoxy-N-methyl-1,2,3,4-tetrahydroisoquinoline;

3-[4-(1,3-benzodioxol-2-yl)-4-(prop-2-yl)-4-cyanobutyl]-6,7-dimethoxy-5,8-diethoxy-N-methyl-1,2,3,4-tetrahydroisoquinoline;

3-[4-(1,3-benzodioxol-2-yl)-4-(but-2-yl)-4-cyanobutyl]-6,7-dimethoxy-5,8-diethoxy-N-methyl-1,2,3,4-tetrahydroisoquinoline;

3-[4-(1,3-benzodioxol-2-yl)-4-(pent-3-yl)-4-cyanobutyl]-6,7-dimethoxy-5,8-diethoxy-N-methyl-1,2,3,4-tetrahydroisoquinoline;

3-[4-(1,4-benzodioxan-2-yl)-4-methyl-4-cyanobutyl]-6,7-dimethoxy-5,8-diethoxy-N-methyl-1,2,3,4-tetrahydroisoquinoline;

3-[4-(1,4-benzodioxan-2-yl)-4-ethyl-4-cyanobutyl]-6,7-dimethoxy-5,8-diethoxy-N-methyl-1,2,3,4-tetrahydroisoquinoline;

3-[4-(1,4-benzodioxan-2-yl)-4-(prop-2-yl)-4-cyanobutyl]-6,7-dimethoxy-5,8-diethoxy-N-methyl-1,2,3,4-tetrahydroisoquinoline;

3-[4-(1,4-benzodioxan-2-yl)-4-(but-2-yl)-4-cyanobutyl]-6,7-dimethoxy-5,8-diethoxy-N-methyl-1,2,3,4-tetrahydroisoquinoline;

3-[4-(1,4-benzodioxan-2-yl)-4-(pent-3-yl)-4-cyanobutyl]-6,7-dimethoxy-5,8-diethoxy-N-methyl-1,2,3,4-tetrahydroisoquinoline;

3-[4-(3,4-dimethoxyphenyl)-4-methyl-4-cyanobutyl]-6,7-dimethoxy-5,8-dipentoxy-N-methyl-1,2,3,4-tetrahydroisoquinoline;

3-[4-(3,4-dimethoxyphenyl)-4-ethyl-4-cyanobutyl]-6,7-dimethoxy-5,8-dipentoxy-N-methyl-1,2,3,4-tetrahydroisoquinoline;

3-[4-(3,4-dimethoxyphenyl)-4-(but-2-yl)-4-cyanobutyl]-6,7-dimethoxy-5,8-dipentoxy-N-methyl-1,2,3,4-tetrahydroisoquinoline;

3-[4-(3,4-dimethoxyphenyl)-4-(pent-3-yl)-4-cyanobutyl]-6,7-dimethoxy-5,8-dipentoxy-N-methyl-1,2,3,4-tetrahydroisoquinoline;

3-[4-(1,3-benzodioxol-2-yl)-4-methyl-4-cyanobutyl]-6,7-dimethoxy-5,8-dipentoxy-N-methyl-1,2,3,4-tetrahydroisoquinoline;

3-[4-(1,3-benzodioxol-2-yl)-4-ethyl-4-cyanobutyl]-6,7-dimethoxy-5,8-dipentoxy-N-methyl-1,2,3,4-tetrahydroisoquinoline;

3-[4-(1,3-benzodioxol-2-yl)-4-(prop-2-yl)-4-cyanobutyl]-6,7-dimethoxy-5,8-dipentoxy-N-methyl-1,2,3,4-tetrahydroisoquinoline;

3-[4-(1,3-benzodioxol-2-yl)-4-(but-2-yl)-4-cyanobutyl]-6,7-dimethoxy-5,8-dipentoxy-N-methyl-1,2,3,4-tetrahydroisoquinoline;

3-[4-(1,3-benzodioxol-2-yl)-4-(pent-3-yl)-4-cyanobutyl]-6,7-dimethoxy-5,8-dipentoxy-N-methyl-1,2,3,4-tetrahydroisoquinoline;

3-[4-(1,4-benzodioxan-2-yl)-4-methyl-4-cyanobutyl]-6,7-dimethoxy-5,8-dipentoxy-N-methyl-1,2,3,4-tetrahydroisoquinoline;

3-[4-(1,4-benzodioxan-2-yl)-4-ethyl-4-cyanobutyl]-6,7-dimethoxy-5,8-dipentoxy-N-methyl-1,2,3,4-tetrahydroisoquinoline;

3-[4-(1,4-benzodioxan-2-yl)-4-(prop-2-yl)-4-cyanobutyl]-6,7-dimethoxy-5,8-dipentoxy-N-methyl-1,2,3,4-tetrahydroisoquinoline;

3-[4-(1,4-benzodioxan-2-yl)-4-(but-2-yl)-4-cyanobutyl]-6,7-dimethoxy-5,8-dipentoxy-N-methyl-1,2,3,4-tetrahydroisoquinoline; and 3-[4-(1,4-benzodioxan-2-yl)-4-(pent-3-yl)-4-cyanobutyl]-6,7-dimethoxy-5,8-dipentoxy-N-methyl-1,2,3,4-tetrahydroisoquinoline.

EXAMPLE 2

(Compounds of Formula 1 via Scheme 2)

(A) A mixture of (3R, 4'S)-3-[4-(3,4-dimethoxyphenyl)-4-isopropyl-4-cyanobutyl]-6,7-dimethoxy-1,2,3,4-tetrahydroisoquinoline (20A, ca. 5 g), formalin (20 mL) and formic acid (25 mL) was stirred for one hour at 100° C., cooled to room temperature, and added to water. The resulting mixture was basified with NH$_4$OH and extracted three times with ether. The organic extract was washed with brine, dried over MgSO$_4$, and evaporated to yield crude (3R, 4'S)-3-[4-(3,4-dimethoxyphenyl)-4-isopropyl-4-cyanobutyl]-6,7-dimethoxy-N-methyl-1,2,3,4-tetrahydroisoquinoline ((−)-1A).

The crude free base was dissolved in ethanol, acidified with HCl, and ether added until crystallization began to yield (3R, 4'S)-3-[4-(3,4-dimethoxyphenyl)-4-isopropyl-4-cyanobutyl]-6,7-dimethoxy-N-methyl-1,2,3,4-tetrahydroisoquinoline·HCl ((−)-1A·HCl, m.p. 110°–113° C., $[\alpha]_D^{25} = -24.4°$ (MeOH)). Calculated for $C_{28}H_{39}ClN_2O_4 \cdot 0.5H_2O$: C=65.74, H=7.78, N=5.48. Found: C=65.69, H=7.89, N=5.46.

(B) Similarly, proceeding as in part (A) above but substituting the compounds prepared in Preparation 17(B) for (3R, 4'S)-3-[4-(3,4-dimethoxyphenyl)-4-isopropyl-4-cyanobutyl]-6,7-dimethoxy-1,2,3,4-tetrahydroisoquinoline, the following compounds are prepared:

(3S, 4'S)-3-[4-(3,4-dimethoxyphenyl)-4-isopropyl-4-cyanobutyl]-6,7-dimethoxyphenyl-N-methyl-1,2,3,4-tetrahydroisoquinoline·HCl;

(3R, 4'S)-3-[4-(3,4-dimethoxyphenyl)-4-isopropyl-4-cyanobutyl]-6,7,8-trimethoxyphenyl-N-methyl-1,2,3,4-tetrahydroisoquinoline·HCl;

(3R, 4'S)-3-[4-(3,4-dimethoxyphenyl)-4-isopropyl-4-cyanobutyl]-6,7,8-trimethoxyphenyl-N-methyl-1,2,3,4-tetrahydroisoquinoline·HCl;

(3S, 4'R)-3-[4-(3,4-dimethoxyphenyl)-4-isopropyl-4-cyanobutyl]-6,7,8-trimethoxyphenyl-N-methyl-1,2,3,4-tetrahydroisoquinoline·HCl;

(3S, 4'S)-3-[4-(3,4-dimethoxyphenyl)-4-isopropyl-4-cyanobutyl]-6,7,8-trimethoxyphenyl-N-methyl-1,2,3,4-tetrahydroisoquinoline·HCl;

(3R, 4'R)-3-[4-(3,4-dimethoxyphenyl)-4-isopropyl-4-cyanobutyl]-6,7-dimethoxy-5,8-diethoxyphenyl-N-methyl-1,2,3,4-tetrahydroisoquinoline·HCl;

(3R, 4'S)-3-[4-(3,4-dimethoxyphenyl)-4-isopropyl-4-cyanobutyl]-6,7-dimethoxy-5,8-diethoxyphenyl-N-methyl-1,2,3,4-tetrahydroisoquinoline·HCl;

(3S, 4'R)-3-[4-(3,4-dimethoxyphenyl)-4-isopropyl-4-cyanobutyl]-6,7-dimethoxy-5,8-diethoxyphenyl-N-methyl-1,2,3,4-tetrahydroisoquinoline·HCl;

3S, 4'S)-3-[4-(3,4-dimethoxyphenyl)-4-isopropyl-4-cyanobutyl]-6,7-dimethoxy-5,8-diethoxyphenyl-N-methyl-1,2,3,4-tetrahydroisoquinoline·HCl;

(3R, 4'R)-3-[4-(3,4-dimethoxyphenyl)-4-isopropyl-4-cyanobutyl]-6,7-dimethoxy-5,8-dipentoxyphenyl-N-methyl-1,2,3,4-tetrahydroisoquinoline·HCl;

(3R, 4'S)-3-[4-(3,4-dimethoxyphenyl)-4-isopropyl-4-cyanobutyl]-6,7-dimethoxy-5,8-dipentoxyphenyl-N-methyl-1,2,3,4-tetrahydroisoquinoline·HCl;

(3S, 4'R)-3-[4-(3,4-dimethoxyphenyl)-4-isopropyl-4-cyanobutyl]-6,7-dimethoxy-5,8-dipentoxyphenyl-N-methyl-1,2,3,4-tetrahydroisoquinoline·HCl; and (3S, 4'S)-3-[4-(3,4-dimethoxyphenyl)-4-isopropyl-4-cyanobutyl]-6,7-dimethoxy-5,8-dipentoxyphenyl-N-methyl-1,2,3,4-tetrahydroisoquinoline·HCl.

EXAMPLE 3

(Compounds of Formula 1 via Scheme 2)

(A) A mixture of (3R, 4'S)-3-[4-(3,4-dimethoxyphenyl)-4-isopropyl-4-cyanobutyl]-6,7-dimethoxy-1,2,3,4-tetrahydroisoquinoline (20A, ca. 5 g), LDA (1 eq) and propyltosylate (1.5 eq) in THF (200 mL) was stirred for one hour at 70° C., cooled to room temperature, and added to water. The resulting mixture was acidified with HCl and extracted three times with ether. The organic extract was washed with aqueous NaHCO$_3$ and brine, dried over MgSO$_4$, and evaporated to yield crude (3R, 4'S)-3-[4-(3,4-dimethoxyphenyl)-4-isopropyl-4-cyanobutyl]-6,7-dimethoxy-N-propyl-1,2,3,4-tetrahydroisoquinoline ((−)-1A).

(B) Similarly, proceeding as in part (A) above but substituting ethyltosylate, isopropyltosylate, butyltosylate, or 2-pentyltosylate, the following compounds are prepared:

(3R, 4'S)-3-[4-(3,4-dimethoxyphenyl)-4-isopropyl-4-cyanobutyl]-6,7-dimethoxy-N-ethyl-1,2,3,4-tetrahydroisoquinoline;

(3R, 4'S)-3-[4-(3,4-dimethoxyphenyl)-4-isopropyl-4-cyanobutyl]-6,7-dimethoxy-N-(2-propyl)-1,2,3,4-tetrahydroisoquinoline;

(3R, 4'S)-3-[4-(3,4-dimethoxyphenyl)-4-isopropyl-4-cyanobutyl]-6,7-dimethoxy-N-butyl-1,2,3,4-tetrahydroisoquinoline; and (3R, 4'S)-3-[4-(3,4-dimethoxyphenyl)-4-isopropyl-4-cyanobutyl]-6,7-dimethoxy-N-pent-2-yl-1,2,3,4-tetrahydroisoquinoline.

(C) Similarly, proceeding as in parts (A-B) above but substituting the compounds prepared in Preparation 17(B) for (3R, 4'S)-3-[4-(3,4-dimethoxyphenyl)-4-isopropyl-4-cyanobutyl]-6,7-dimethoxy-1,2,3,4-tetrahydroisoquinoline, the following N-alkyl compounds are prepared:

(3S, 4'S)-3-[4-(3,4-dimethoxyphenyl)-4-isopropyl-4-cyanobutyl]-6,7-dimethoxyphenyl-N-ethyl-1,2,3,4-tetrahydroisoquinoline;

(3R, 4'R)-3-[4-(3,4-dimethoxyphenyl)-4-isopropyl-4-cyanobutyl]-6,7,8-trimethoxyphenyl-N-ethyl-1,2,3,4-tetrahydroisoquinoline;

(3R, 4'S)-3-[4-(3,4-dimethoxyphenyl)-4-isopropyl-4-cyanobutyl]-6,7,8-trimethoxyphenyl-N-ethyl-1,2,3,4-tetrahydroisoquinoline;

(3S, 4'R)-3-[4-(3,4-dimethoxyphenyl)-4-isopropyl-4-cyanobutyl]-6,7,8-trimethoxyphenyl-N-ethyl-1,2,3,4-tetrahydroisoquinoline;

(3S, 4'S)-3-[4-(3,4-dimethoxyphenyl)-4-isopropyl-4-cyanobutyl]-6,7,8-trimethoxyphenyl-N-ethyl-1,2,3,4-tetrahydroisoquinoline;

(3R, 4'R)-3-[4-(3,4-dimethoxyphenyl)-4-isopropyl-4-cyanobutyl]-6,7-dimethoxy-5,8-diethoxyphenyl-N-ethyl-1,2,3,4-tetrahydroisoquinoline;

(3R, 4'S)-3-[4-(3,4-dimethoxyphenyl)-4-isopropyl-4-cyanobutyl]-6,7-dimethoxy-5,8-diethoxyphenyl-N-ethyl-1,2,3,4-tetrahydroisoquinoline;

(3S, 4'R)-3-[4-(3,4-dimethoxyphenyl)-4-isopropyl-4-cyanobutyl]-6,7-dimethoxy-5,8-diethoxyphenyl-N-ethyl-1,2,3,4-tetrahydroisoquinoline;

(3S, 4'S)-3-[4-(3,4-dimethoxyphenyl)-4-isopropyl-4-cyanobutyl]-6,7-dimethoxy-5,8-diethoxyphenyl-N-ethyl-1,2,3,4-tetrahydroisoquinoline;

(3R, 4'R)-3-[4-(3,4-dimethoxyphenyl)-4-isopropyl-4-cyanobutyl]-6,7-dimethoxy-5,8-dipentoxyphenyl-N-ethyl-1,2,3,4-tetrahydroisoquinoline;

(3R, 4'S)-3-[4-(3,4-dimethoxyphenyl)-4-isopropyl-4-cyanobutyl]-6,7-dimethoxy-5,8-dipentoxyphenyl-N-ethyl-1,2,3,4-tetrahydroisoquinoline;

(3S, 4'R)-3-[4-(3,4-dimethoxyphenyl)-4-isopropyl-4-cyanobutyl]-6,7-dimethoxy-5,8-dipentoxyphenyl-N-ethyl-1,2,3,4-tetrahydroisoquinoline;

(3S, 4'S)-3-[4-(3,4-dimethoxyphenyl)-4-isopropyl-4-cyanobutyl]-6,7-dimethoxy-5,8-dipentoxyphenyl-N-ethyl-1,2,3,4-tetrahydroisoquinoline;

(3S, 4'S)-3-[4-(3,4-dimethoxyphenyl)-4-isopropyl-4-cyanobutyl]-6,7-dimethoxyphenyl-(N-prop-2-yl)-1,2,3,4-tetrahydroisoquinoline;

(3R, 4'R)-3-[4-(3,4-dimethoxyphenyl)-4-isopropyl-4-cyanobutyl]-6,7,8-trimethoxyphenyl-(N-prop-2-yl)-1,2,3,4-tetrahydroisoquinoline;

(3R, 4'S)-3-[4-(3,4-dimethoxyphenyl)-4-isopropyl-4-cyanobutyl]-6,7,8-trimethoxyphenyl-(N-prop-2-yl)-1,2,3,4-tetrahydroisoquinoline;

(3S, 4'R)-3-[4-(3,4-dimethoxyphenyl)-4-isopropyl-4-cyanobutyl]-6,7,8-trimethoxyphenyl-(N-prop-2-yl)-1,2,3,4-tetrahydroisoquinoline;

(3S, 4'S)-3-[4-(3,4-dimethoxyphenyl)-4-isopropyl-4-cyanobutyl]-6,7,8-trimethoxyphenyl-(N-prop-2-yl)-1,2,3,4-tetrahydroisoquinoline;

(3R, 4'R)-3-[4-(3,4-dimethoxyphenyl)-4-isopropyl-4-cyanobutyl]-6,7-dimethoxy-5,8-diethoxyphenyl-(N-prop-2-yl)-1,2,3,4-tetrahydroisoquinoline;
(3R, 4'S)-3-[4-(3,4-dimethoxyphenyl)-4-isopropyl-4-cyanobutyl]-6,7-dimethoxy-5,8-diethoxyphenyl-(N-prop-2-yl)-1,2,3,4-tetrahydroisoquinoline;
(3S, 4'R)-3-[4-(3,4-dimethoxyphenyl)-4-isopropyl-4-cyanobutyl]-6,7-dimethoxy-5,8-diethoxyphenyl-(N-prop-2-yl)-1,2,3,4-tetrahydroisoquinoline;
(3S, 4'S)-3-[4-(3,4-dimethoxyphenyl)-4-isopropyl-4-cyanobutyl]-6,7-dimethoxy-5,8-diethoxyphenyl-(N-prop-2-yl)-1,2,3,4-tetrahydroisoquinoline;
(3R, 4'R)-3-[4-(3,4-dimethoxyphenyl)-4-isopropyl-4-cyanobutyl]-6,7-dimethoxy-5,8-dipentoxyphenyl-(N-prop-2-yl)-1,2,3,4-tetrahydroisoquinoline;
(3R, 4'S)-3-[4-(3,4-dimethoxyphenyl)-4-isopropyl-4-cyanobutyl]-6,7-dimethoxy-5,8-dipentoxyphenyl-(N-prop-2-yl)-1,2,3,4-tetrahydroisoquinoline;
(3S, 4'R)-3-[4-(3,4-dimethoxyphenyl)-4-isopropyl-4-cyanobutyl]-6,7-dimethoxy-5,8-dipentoxyphenyl-(N-prop-2-yl)-1,2,3,4-tetrahydroisoquinoline;
(3S, 4'S)-3-[4-(3,4-dimethoxyphenyl)-4-isopropyl-4-cyanobutyl]-6,7-dimethoxy-5,8-dipentoxyphenyl-(N-prop-2-yl)-1,2,3,4-tetrahydroisoquinoline;
(3S, 4'S)-3-[4-(3,4-dimethoxyphenyl)-4-isopropyl-4-cyanobutyl]-6,7-dimethoxyphenyl-N-butyl-1,2,3,4-tetrahydroisoquinoline;
(3R, 4'R)-3-[4-(3,4-dimethoxyphenyl)-4-isopropyl-4-cyanobutyl]-6,7,8-trimethoxyphenyl-N-butyl-1,2,3,4-tetrahydroisoquinoline;
(3R, 4'S)-3-[4-(3,4-dimethoxyphenyl)-4-isopropyl-4-cyanobutyl]-6,7,8-trimethoxyphenyl-N-butyl-1,2,3,4-tetrahydroisoquinoline;
(3S, 4'R)-3-[4-(3,4-dimethoxyphenyl)-4-isopropyl-4-cyanobutyl]-6,7,8-trimethoxyphenyl-N-butyl-1,2,3,4-tetrahydroisoquinoline;
(3S, 4'S)-3-[4-(3,4-dimethoxyphenyl)-4-isopropyl-4-cyanobutyl]-6,7,8-trimethoxyphenyl-N-butyl-1,2,3,4-tetrahydroisoquinoline;
(3R, 4'R)-3-[4-(3,4-dimethoxyphenyl)-4-isopropyl-4-cyanobutyl]-6,7-dimethoxy-5,8-diethoxyphenyl-N-butyl-1,2,3,4-tetrahydroisoquinoline;
(3R, 4'S)-3-[4-(3,4-dimethoxyphenyl)-4-isopropyl-4-cyanobutyl]-6,7-dimethoxy-5,8-diethoxyphenyl-N-butyl-1,2,3,4-tetrahydroisoquinoline;
(3S, 4'R)-3-[4-(3,4-dimethoxyphenyl)-4-isopropyl-4-cyanobutyl]-6,7-dimethoxy-5,8-diethoxyphenyl-N-butyl-1,2,3,4-tetrahydroisoquinoline;
(3S, 4'S)-3-[4-(3,4-dimethoxyphenyl)-4-isopropyl-4-cyanobutyl]-6,7-dimethoxy-5,8-diethoxyphenyl-N-butyl-1,2,3,4-tetrahydroisoquinoline;
(3R, 4'R)-3-[4-(3,4-dimethoxyphenyl)-4-isopropyl-4-cyanobutyl]-6,7-dimethoxy-5,8-dipentoxyphenyl-N-butyl-1,2,3,4-tetrahydroisoquinoline;
(3R, 4'S)-3-[4-(3,4-dimethoxyphenyl)-4-isopropyl-4-cyanobutyl]-6,7-dimethoxy-5,8-dipentoxyphenyl-N-butyl-1,2,3,4-tetrahydroisoquinoline;
(3S, 4'R)-3-[4-(3,4-dimethoxyphenyl)-4-isopropyl-4-cyanobutyl]-6,7-dimethoxy-5,8-dipentoxyphenyl-N-butyl-1,2,3,4-tetrahydroisoquinoline;
(3S, 4'S)-3-[4-(3,4-dimethoxyphenyl)-4-isopropyl-4-cyanobutyl-6,7-dimethoxy-5,8-dipentoxyphenyl-N-butyl-1,2,3,4-tetrahydroisoquinoline;
(3S, 4'S)-3-[4-(3,4-dimethoxyphenyl)-4-isopropyl-4-cyanobutyl]-6,7-dimethoxyphenyl-(N-pent-2-yl)-1,2,3,4-tetrahydroisoquinoline;
(3R, 4'R)-3-[4-(3,4-dimethoxyphenyl)-4-isopropyl-4-cyanobutyl]-6,7,8-trimethoxyphenyl-(N-pent-2-yl)-1,2,3,4-tetrahydroisoquinoline;
(3R, 4'S)-3-[4-(3,4-dimethoxyphenyl)-4-isopropyl-4-cyanobutyl]-6,7,8-trimethoxyphenyl-(N-pent-2-yl)-1,2,3,4-tetrahydroisoquinoline;
(3S, 4'R)-3-[4-(3,4-dimethoxyphenyl)-4-isopropyl-4-cyanobutyl]-6,7,8-trimethoxyphenyl-(N-pent-2-yl)-1,2,3,4-tetrahydroisoquinoline;
(3S, 4'S)-3-[4-(3,4-dimethoxyphenyl)-4-isopropyl-4-cyanobutyl]-6,7,8-trimethoxyphenyl-(N-pent-2-yl)-1,2,3,4-tetrahydroisoquinoline;
(3R, 4'R)-3-[4-(3,4-dimethoxyphenyl)-4-isopropyl-4-cyanobutyl]-6,7-dimethoxy-5,8-diethoxyphenyl-(N-pent-2-yl)-1,2,3,4-tetrahydroisoquinoline;
(3R, 4'S)-3-[4-(3,4-dimethoxyphenyl)-4-isopropyl-4-cyanobutyl]-6,7-dimethoxy-5,8-diethoxyphenyl-(N-pent-2-yl)-1,2,3,4-tetrahydroisoquinoline;
(3S, 4'R)-3-[4-(3,4-dimethoxyphenyl)-4-isopropyl-4-cyanobutyl]-6,7-dimethoxy-5,8-diethoxyphenyl-(N-pent-2-yl)-1,2,3,4-tetrahydroisoquinoline;
(3S, 4'S)-3-[4-(3,4-dimethoxyphenyl)-4-isopropyl-4-cyanobutyl]-6,7-dimethoxy-5,8-diethoxyphenyl-(N-pent-2-yl)-1,2,3,4-tetrahydroisoquinoline;
(3R,4'R)-3-[4-(3,4-dimethoxyphenyl)-4-isopropyl-4-cyanobutyl]-6,7-dimethoxy-5,8-dipentoxyphenyl-(N-pent-2-yl)-1,2,3,4-tetrahydroisoquinoline;
(3R,4'S)-3-[4-(3,4-dimethoxyphenyl)-4-isopropyl-4-cyanobutyl]-6,7-dimethoxy-5,8-dipentoxyphenyl-(N-pent-2-yl)-1,2,3,4-tetrahydroisoquinoline;
(3S,4'R)-3-[4-(3,4-dimethoxyphenyl)-4-isopropyl-4-cyanobutyl]-6,7-dimethoxy-5,8-dipentoxyphenyl-(N-pent-2-yl)-1,2,3,4-tetrahydroisoquinoline; and
(3S,4'S)-3-[4-(3,4-dimethoxyphenyl)-4-isopropyl-4-cyanobutyl]-6,7-dimethoxy-5,8-dipentoxyphenyl-(N-pent-2-yl)-1,2,3,4-tetrahydroisoquinoline.

EXAMPLE 4

(Salts of Compounds of Formula 1)

(A) The free base, 3-[4-(3,4-dimethoxyphenyl)-4-isopropyl-4-cyanobutyl]-6,7-dimethoxy-N-methyl-1,2,3,4-tetrahydroisoquinoline (1, 15 g, 0.032 mol) was dissolved in isopropanol (70 mL) at 70° C., and 6M HCl in isopropanol (5.6 mL) slowly added. After cooling to room temperature, ether (40 mL) was added until the solution became cloudy (saturated), and the resulting mixture stirred overnight. The resulting solid was collected, washed thoroughly with ether-isopropanol (1:1, 50 mL), and dried in vacuo at 50° C. to yield 3-[4-(3,4-dimethoxyphenyl)-4-isopropyl-4-cyanobutyl]-6,7-dimethoxy-N-methyl-1,2,3,4-tetrahydroisoquinoline·HCl (1·HCl, 13.7 g, m.p. 115°–120° C.) as a white powder.

(B) Similarly, proceeding as in part (A) above, but substituting the compounds prepared in Example 1(B), the corresponding hydrochloride salts are prepared.

(C) Similarly, proceeding as in parts (A-B) above, but substituting hydrobromic acid, sulfuric acid, nitric acid, phosphoric acid, acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, or p-toluenesulfonic acid for hydrochloric acid, the corresponding salts are prepared.

EXAMPLE 5

(Formulations)

The following example illustrates the preparation of representative pharmaceutical formulations containing an active compound of formula 1, e.g., 3-[4-(3,4-dimethoxyphenyl)-4-cyano-4-isopropylbutyl]-6,7-dimethoxy-N-methyl-1,2,3,4-tetrahydroisoquinoline (1).

| I.V. Formulation | |
|---|---|
| Active compound | 0.01 g |
| Propylene glycol | 20.0 g |
| Polyethylene glycol 400 | 20.0 g |
| Tween 80 | 1.0 g |
| 0.9% Saline solution qs | 100.0 mL |

The active compound is dissolved in propylene glycol, polyethylene glycol 400 and Tween 80. A sufficient quantity of 0.9% saline solution is then added with stirring to provide 100 mL of the I.V. solution which is filtered through a 0.2 micron membrane filter and packaged under sterile conditions.

| TABLET FORMULATION | parts by weight |
|---|---|
| Active compound | 25.0 |
| Magnesium stearate | 0.2 |
| Pregelatinized starch | 74.8 |

The above ingredients are dry-blended and loaded into #0 capsules containing about 100 mg active compound per capsule.

EXAMPLE 6

(Spontaneously Hypertensive Rat Assay)

Twenty-four previously trained adult male spontaneously hypertensive rats are distributed into 6 groups (4 animals per group) with approximately equal mean systolic blood pressures. The 6 groups are then studied concurrently in a 2-day compound screening procedure.

Test compounds are randomly assigned to each group. Five groups receive potential antihypertensive agents and 1 control group receives vehicle only (water and Tween).

At approximately 17 hours prior to the first day of dosing food is removed from the rat cages. On the morning of Day 1, a group of 4 rats is orally dosed (by gavage) with 12.5 mg/kg or 25 mg/kg of a compound of formula 1 dissolved/suspended in water (using 2-3 drops Tween 80) with a homogenizer at concentrations such that 0.1 mL of solution is administered per 10 g of body weight. At 4½ hours post dose, food is put back in the cages and the rats are allowed to eat for 2½ hours, after which food is again removed. On the morning of Day 2, rats are orally dosed as described above. Immediately after dosing, the rats are put in restrainers and placed in a heated chamber (30±1.0° C.) for four hours. Normal feeding resumes at the end of the study on Day 2.

Systolic blood pressure (i.e., pressure at the appearance of the first pulse) is recorded using photoelectric transducers. The coccygeal arteries of 3 rats (in a horizontal group) are simultaneously occluded by pump-inflated tail cuffs that are automatically inflated to 300 mmHg and then deflated. A pressure curve and tail pulses are simultaneously monitored on an MFE recorder. Four consecutive (at 30 second intervals) traces are recorded for each rat in a given horizontal group at one, two, three and four hours post compound administration. Subsequent horizontal groups are automatically tested in the same manner.

The mean systolic blood pressure (SBP) of each rat at each observation time is calculated. The SBP of the animals in each dose group is compared to the SBP of the animals in the control group (vehicle only) at each observation time using a one-way analysis of variance test. Data exhibiting $p \leq 0.05$ at any observation time is considered to indicate a compound exhibiting significant antihypertensive activity. Compounds significantly decreasing blood pressure 20 mmHg or more from control values at all four observation times are considered worthy of further examination. In these instances heart rates were calculated and tested for significant change from control heart rate values using the two-tailed test. Pressures are read at hours 1, 2, 3 and 4 after dosing on both days 1 and 2. The compounds of the invention exhibit positive antihypertensive activity in this test.

EXAMPLE 7

(Canine Echocardiography Assay)

A group of mongrel dogs, 18 to 25 kg, is chosen for the clarity of images that can be obtained from them via ultrasonic two-dimensional echocardiography (2DE). Animals from this group are used in two different models employing 2DE. In the first model the dogs are anesthetized; in the second they are conscious and nonsedated throughout the test drug administration.

In both models a small branch of femoral artery is cannulated, via an arterial cutdown, with a length of water-filled tubing connected to a pressure transducer. In the conscious model, the femoral cutdown site is anesthetized with a local subcutaneous injection of 2% Lidocaine. This transducer provides a means to monitor blood pressure. Blood pressure and ECG are recorded on a two channel chart recorder.

An ultrasound realtime scanner, connected to a 3 MgHz endfire transducer, placed in a right parasternal approach on the fourth of fifth intercostal space, produces the 2DE images. Images include a long axis view of the left ventricle defined as simultaneously imaging the apex, mitral valve, and a round left atrium. Additionally, short axis views at the high papillary muscle level are obtained. All images are recorded on video tape for later analysis. Analysis is accomplished using a computerized graphics program interfaced with the videorecorder and a bit pad.

In the first model the dogs are anesthetized with sodium pentobarbital. They are placed on their right sides on a support that allows access, via a cutout to the right parasternal area. Doses of 50, 100, 200, and 500 μg/kg of a compound of the invention are administered intravenously over the course of the experiment day. The compound is dissolved in 2:1 distilled water-dimethyl acetamide. Control values are obtained for each dose and further measurements are taken at 3, 5, 10, 15, and 30 minutes after administration of each dose.

In the second model the dogs are trained to stand quietly for several hours in a sling. The right parasternal area is accessed via a buttoned-down panel in the sling. Doses of 5.0 and 5.5 mg/kg of a compound of the invention are administered intravenously, dissolved in 7:1 distilled water-ethanol, as are doses of 1.5 and 1.0 mg/kg of a compound of the invention dissolved in 3:1 distilled water-dimethyl acetamide. Additionally, doses of 5, 2, 1, and 0.75 mg/kg of a compound of the invention are administered orally, with the compound in a gelatin capsule. Control values are obtained prior to each dose. During the intravenous studies additional measurements are obtained at intervals of 5, 10, 15, 30, 45, and 60 minutes after the administration of each dose. During the oral studies additional measurements are obtained at intervals of 10, 20, 30, 45, 60, 75, 90. 105, 120, and 180 minutes after the administration of each dose. The compounds of the invention demonstrate positive activity in this assay.

EXAMPLE 8

(Anesthetized Dog Assay)

Mongrel dogs ranging in weight from 14 to 21 kg are anesthetized with pentobarbital sodium (35 mg/kg, i.v.), intubated and the chest opened at the left fifth intercostal space. The animals are instrumented to measure the following parameters: systolic, diastolic and mean blood pressure, heart rate, left ventricular pressure, left ventricular dp/dt max, pulmonary capillary wedge pressure, central venous pressure, cardiac output, systemic vascular resistance, contractile force, and coronary blood flow.

Left ventricular pressure is measured using a Millar micro-tip catheter. Electronic differentiation of this signal provides dp/dt maximum. Systolic, diastolic and mean blood pressure, and central venous pressure are evaluated using fluid-filled Statham pressure transducers. Cardiac output and pulmonary capillary wedge pressure are measured using a Swan-Ganz catheter connected to a Statham water-filled pressure transducer and a Gould Cardiac Index Computer. Contractile force is determined via a Walton-Brodie Strain gauge arch sewn to the left ventricle. Systemic vascular resistance is calculated using cardiac output and blood pressure measurements. Epicardial coronary blood flow is measured with an electromagnetic flow probe (Carolina Medical Electronics, Co.). Myocardial blood flow is evaluated using radioactive-labelled microspheres (5: $^{85}Sr$, $^{141}Ce$, $^{51}Cr$, $^{113}Sn$, $^{46}Sc$). This data is counted with a Packard model 3500 gamma counter and a Canberra Model Multichannel Analyzer, and analyzed with the aid of Syntex-developed software run on a HP1000 Computer.

A compound of the invention is prepared for administration in a vehicle of dimethylacetamide and saline (for intravenous use) or dimethylacetamide and water (for intraduodenal use). Appropriate controls are also examined.

One group of animals is given a compound of the invention intravenously at the following doses: 25, 50, 100, 200 and 500 μg/kg. The above-named parameters are monitored for at least 30 minutes after each dose.

The second group of animals is given a compound of the invention intraduodenally at a dose of 5 mg/kg. The above mentioned parameters are monitored for 3 to 4 hours after drug administration.

In a third group of animals, a compound of the invention is administered intracoronary to determine the direct local effects of the compound. All of the above-mentioned parameters are monitored for 10-15 minutes after drug administration except myocardial blood flow (microsphere method). The doses administered are 1, 2, 5, 10, and 20 mg/kg.

In a fourth group of animals, a compound of the invention is administered intravenously after pretreatment with d-, l-, or dl-propranolol (0.5 mg/kg, i.v.). All parameters are monitored for one hour after drug administration.

The data is summarized with mean values ± the standard error from the mean. When indicated, statistics are done with paired or unpaired Student's t-test. The compounds of the invention exhibit positive activity in this assay.

EXAMPLE 9

(Rat Aortic Strip Assay)

Four male Sprague-Dawley rats (250–300 g per rat, obtained from Bantin & Kingman) were sacrificed by cervical dislocation. The thoracic aortas were quickly removed and the adventitial connective tissue carefully removed. The aortas were cut into helical strips 2–3 cm wide and 3 cm long. The strips were mounted vertically in tissue baths containing 10 mL modified Krebs solution at 37° C., and allowed to equilibrate with a gas mixture of 95% $O_2$ and 5% $CO_2$.

An initial tension of 1 g was applied to the strips. The systems were allowed to equilibrate for one hour, during which period the strips were washed six times. The strips were then contracted with either $BaCl_2$ ($10^{-3}M$) or phenylephrine ($10^{-7}M$), and were allowed to reach a steady response. The strips were then subjected to stepwise increasing concentrations of compounds of the invention and the responses recorded using Statham UC-2 transducers and a Beckman R611 Dynograph recorder. The compounds of the invention demonstrated high activity as calcium channel blockers in this assay.

EXAMPLE 10

(Calcium Blockade Tissue Selectivity)

Four male New Zealand White rabbits (2.5–3.5 Kg per rabbit, Elkhorn) were sacrificed using pentobarbital sodium (50 mg/Kg, i.v. via the ear vein) and quickly decapitated. The brains were quickly removed and placed in a dish of modified Krebs buffer aerated with 95% $O_2$/5% $CO_2$. The basilar arteries were dissected out and placed in a separate aerated dish of buffer. A section of central ear artery (30 mm) from each rabbit was removed from the middle of the ear and placed in an aerated buffer dish. The basilar and ear arteries were carefully cleaned and cut into cross-sectional rings. Basilar artery rings were about 3 mm long; ear artery rings were about 2 mm long. The rings were mounted in holders in tissue baths containing 10 mL modified Krebs solution at 37° C., and allowed to equilibrate with a gas mixture of 95% $O_2$ and 5% $CO_2$.

An initial tension of 0.5 g was applied to the rings. The systems were allowed to equilibrate for one hour, during which period the rings were washed six times. The rings were then contracted with KCl sufficient to evoke a 1 g contraction, and were allowed to reach a steady response. The rings were then subjected to stepwise increasing concentrations of compounds of the invention and the responses recorded using Statham UC-2 transducers and a Beckman R611 Dynograph recorder. The compounds of the invention demonstrated high activity and good selectivity as calcium channel blockers in this assay.

What is claimed is:

1. A compound of the formula

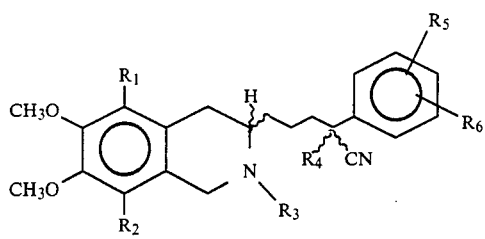

or a pharmaceutically acceptable acid addition salt thereof, wherein $R_1$ and $R_2$ are each independently —H or lower alkoxy;

$R_3$ and $R_4$ are each independently lower alkyl; and $R_5$ and $R_6$ are each —OCH$_3$, or together form —OCH$_2$O— or —OCH$_2$CH$_2$O—.

2. The compound of claim 1 wherein $R_4$ is isopropyl.

3. The compound of claim 2 wherein $R_3$ is methyl.

4. The compound of claim 3 wherein $R_1$ and $R_2$ are each —H.

5. The compound of claim 4 wherein $R_5$ and $R_6$ are each —OCH$_3$.

6. The compound of claim 5 which is 3-[4-(3,4-dimethoxyphenyl)-4-isopropyl-4-cyanobutyl]-6,7-dimethoxy-N-methyl-1,2,3,4-tetrahydroisoquinoline.

7. The compound of claim 5 wherein the stereochemistry at $C_3$ is S.

8. The compound of claim 7 which is (3S,4'S) 3-[4-(3,4-dimethoxyphenyl)-4-isopropyl-4-cyanobutyl]-6,7-dimethoxy-N-methyl-1,2,3,4-tetrahydroisoquinoline.

9. A pharmaceutical composition for treating angina, hypertension or congestive heart failure, comprising a pharmaceutically acceptable carrier; and an effective amount of a compound of formula 1,

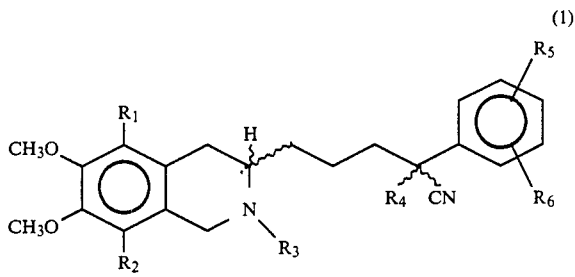

wherein $R_1$ and $R_2$ are each independently —H or lower alkoxy;

$R_3$ and $R_4$ are each independently lower alkyl; and $R_5$ and $R_6$ are each —OCH$_3$, or together form —OCH$_2$O— or —OCH$_2$CH$_2$O—.

10. The composition of claim 9 wherein said compound of formula 1 is (racemic) 3-[4-(3,4-dimethoxyphenyl)-4-cyano-4-isopropylbutyl]-6,7-dimethoxy-N-methyl-1,2,3,4-tetrahydroisoquinoline.

* * * * *